(12) United States Patent
Falkenberg et al.

(10) Patent No.: US 6,406,689 B1
(45) Date of Patent: *Jun. 18, 2002

(54) COMPOSITIONS AND METHODS FOR TREATMENT OF TUMORS AND METASTATIC DISEASES

(75) Inventors: Frank W. Falkenberg, Am Berge 8b, D-58456 Witten; Oliver C. Krup, Herten, both of (DE)

(73) Assignee: Frank W. Falkenberg, Witten (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/261,816

(22) Filed: Mar. 3, 1999

Related U.S. Application Data

(63) Continuation-in-part of application No. 08/538,730, filed on Oct. 3, 1995.

(51) Int. Cl.$^7$ .................. A01N 63/00; A61K 39/00; A61K 39/39; C12N 5/06; C01F 7/02
(52) U.S. Cl. .............. 424/93.1; 424/184.1; 424/277.1; 423/625; 435/325; 514/965; 514/963
(58) Field of Search ................ 424/93.1, 184.1, 424/277.1; 435/325; 423/625

(56) References Cited

U.S. PATENT DOCUMENTS

| | | |
|---|---|---|
| 4,863,740 A | 9/1989 | Kissel et al. |
| 4,877,611 A | 10/1989 | Cantrell |
| 4,931,275 A | 6/1990 | Shinitzky et al. |
| 5,273,745 A | 12/1993 | Schirrmacher |
| 5,409,698 A | 4/1995 | Anderson et al. |
| 5,563,250 A | 10/1996 | Hylarides et al. |
| 5,582,831 A | 12/1996 | Shinitzky |
| 5,861,159 A | 1/1999 | Pardoll et al. ............ 424/184.1 |
| 5,942,253 A | 8/1999 | Gombotz et al. ............ 424/501 |
| 6,120,807 A | 9/2000 | Gombotz et al. ............ 424/501 |
| 6,193,970 B1 | 2/2001 | Pardoll et al. ............ 424/184.1 |
| 6,218,166 B1 | 4/2001 | Ravindranath et al. .. 435/240.2 |
| 6,274,175 B1 | 4/2001 | Gombotz et al. ............ 424/501 |
| 6,277,368 B1 | 8/2001 | Hiserodt et al. ......... 424/93.21 |

OTHER PUBLICATIONS

Martin et al. Cancer Research. 46:2189–2192, Apr. 1986.*
Falkenberg et al. *Cytokine–Depot–Tumor–Vaccines: The Basic Principle*, Cancer Research Institute, International Symposium, Oct. 1998.
Ostrand–Rosenberg et al., *Cell–based Vaccines for the Stimulation of Immunity to Metastatic Cancers*, Immunological Reviews, vol. 170, p. 101–114, 1999.
Goto and Akama, *Histopathological Studies of Reactions in Mice Injected with Aluminum–Adsorbed Tetanus Toxoid*, Microbiol. Immunol., vol. 26 (12), pp. 1121–1132, 1982.
Sanda et al., *Demonstration of a Rational Strategy for Human Prostate Cancer Gene Therapy*, The Journal of Urology, vol. 151, pp. 622–628, 1994.
Blankenstein and Qin, *Cancer Vaccines in Gene Therapy*, Gene Therapy (Editorial), vol. 3., 1995–96.
Hargest and Williamson, *Prophylactic Gene Therapy for Cancer*, Gene Therapy, vol. 3, pp. 97–102, 1996.
Jaffee et al., *Enhanced Immune Priming with Spatial Distribution of Paracrine Cytokine Vaccines*, Journal of Immunotherapy, vol. 19, No. 3, pp. 176–183, 1996.
Jafee and Pardoll, *Considerations for the Clinical Development of Cytokine Gene–Transduced Tumor Cell Vaccines*, John Hopkins University School of Medicine, pp. 143–153, 1997.
Jankovic et al., *Adsorption to Aluminum Hydroxide Promotes the Activity of IL–12 as an Adjuvant for Antibody as Well as Type 1 Cytokine Responses to HIV–1 gp120*, The Journal of Immunology, 1997.
Simons et al., *Bioactivity of Autologous Irradiated Renal Cell Carcinoma Vaccines Generated by Ex Vivo Granulocyte–Macrophage Colony–Stimulating Factor Gene Transfer*, Cancer Research, 57(8), pp. 1537–1546, 1997.
Falkenberg et al., *Cytokine–Depot–Tumor–Vaccines: The Basic Principle*, Cancer Research Institute International Symposium, New York, NY, Oct. 1998.
Pardoll, *Cancer Vaccines*, Nature Medicine Vaccine Supplement, vol. 4, No. 5, pp. 525–531, 1998.
Soiffer et al., *Vaccination With Irradiated Autologous Melanoma Cells Engineered To Secrete Human Granulocyte–Macrophage Colony–Stimulating Factor Generates Potent Antitumor Immunity In Patients With Metastatic Melanoma*, Proc. Natl. Acad. Sci., vol. 95, pp. 13141–13146, 1998.
Herbert et al., *The Dictionary of Immunology*, Academic Press, pp. 1–148, 1985.
Smith, *Interleukin–2: Inception, Impact, and Implications*, Science, vol. 240, pp. 1169–1176, May 1988.

(List continued on next page.)

*Primary Examiner*—Geetha P. Bansal
(74) *Attorney, Agent, or Firm*—Workman, Nydegger & Seeley

(57) ABSTRACT

Compositions and methods are provided which can be utilized in active immunization as a prophylactic treatment or a therapeutic treatment for tumors. The compositions are employed as injectable tumor vaccines or as preparations for intratumoral administration and are capable of stimulating immune responses to specific tumor antigens. The tumor vaccines are composed of an antigenic cellular material including a plurality of inactivated tumor cells or tumor cell portions, a depot material, and an immunostimulant adsorbed to the depot material. The depot material with absorbed immunostimulant is mixed with the tumor cells or tumor cell portions to form the vaccine compositions. The preparations for intratumoral administration include the depot material adsorbed immunostimulant without the antigenic cellular material. The immunostimulant adsorbed to the depot material permits release of biologically active quantities of the immunostimulant over a period of time rather than all at once.

9 Claims, 16 Drawing Sheets

OTHER PUBLICATIONS

Kato, *Characteristics of Natural and Recombinant Human Interleukin 2*, Interleukin 2, pp. 37–66, 1988.

Paul, *Vaccines, Fundamental Immunology*, 2nd ed. (Chapter 36), pp. 1007–1009, 1989.

Cryz, *Immunotherapy and Vaccines*, Principles and Definitions, pp. 3–12, 1991.

Bennett et al., *A Comparison of Commercially Available Adjuvants for use in Research*, Journal of Immunological Methods, 153, pp. 31–32, 1992.

Anderson et al., *Depot Characteristics and Biodistribution of Interleukin–2 Liposomes: Importance of Route of Administration*, Journal of Immunotherapy, vol. 12, No. 1, pp. 19–31, 1992.

Phillips, *Production of Reagent Antibodies, Analytical Techniques in Immunochemistry*, pp. 307–314, 1992.

Le, *Hypothesis Testing, Fundamentals of Biostatistical Inference*, Chpt. 3, pp. 152–155, 1992.

Press et al., *Statistical Description of Data, Numerical Recipes in Fortran*, Chpt. 14, pp. 603–649, 1992.

Ferencik, *Biosynthesis of Antibodies, Handbook of Immunochemistry*, pp. 114–117, 1993.

Livingston, *Conference Overview*, Specific Immunotherapy of Cancer with Vaccines, Annals of the New York Academy of Sciences, vol. 690, pp. 1–5, 1993.

Hellstrom and Hellstrom, *Tumor Immunology: An Overview*, Specific Immunotherapy of Cancer with Vaccines, Annals of the New York Academy of Sciences, vol. 690, pp. 24–33, 1993.

Sogn et al., *Cancer Vaccines: The Perspective of the Cancer Immunology Branch, NCI*, Specific Immunotherapy of Cancer with Vaccines, Annals of the New York Academy of Sciences, vol. 690, pp. 322–330, 1993.

Bash, *Active Specific Immunotherapy of Murine Colon Adenocarcinoma with Recombinant Vaccinia/Interleukin–2–Infected Tumor Cell Vaccines$^{\alpha}$*, Specific Immunotherapy of Cancer with Vaccines, Annals of the New York Academy of Sciences, vol. 690, pp. 331–333, 1993.

Lord et al., *Transfection of TGF–β Producing Tumors with IL–2 Elicits Tumor Rejection$^{\alpha}$*, Specific Immunotherapy of Cancer with Vaccines, Annals of the New York Academy of Sciences, vol. 690, pp. 346–348, 1993.

McAdam et al., *Coexpression of IL–2 and γ–IFN Enhances Tumor Immunity$^{\alpha}$*, Specific Immunotherapy of Cancer with Vaccines, Annals of the New York Academy of Sciences, vol. 690, pp. 349–351, 1993.

Dranoff et al., *Vaccination with Irradiated Tumor Cells Engineered to Secrete Murine Granulocyte–Macrophage Colony–Stimulating Factor Stimulates Potent, Specific, and Long–lasting Anti–tumor Immunity*, Proc. Natl. Acad. Sci., vol. 90, pp. 3539–3543, Apr. 1993.

Dohlsten et al., *Monoclonal Antibody–Superantigen Fusion Proteins: Tumor–Specific Agents for T–Cell–based Tumor Therapy*, Proc. Natl. Acad. Sci., vol. 91, pp. 8945–8949, Sep. 1994.

Sabzevari et al., *A Recombinant Antibody–Interleukin 2 Fusion Protein Suppresses Growth of Hepatic Human Neuroblastoma Metastases in Severe Combined Immunodeficiency Mice*, Proc. Natl. Acad, Sci., vol. 91, pp. 9626–9630, Sep. 1994.

Falkenberg, *A Tumor Vaccine Consisting of Cytokine Containing Liposomes Covalently Coupled to Tumor Cells—An Alternative to Gene Transfected Tumor Cells?*, Cancer Vaccines, Structural Basis for Vaccine Development, Cancer Research Institute Symposium, Oct. 1994.

Lotze, *Introduction*, Annals of the New York Academy of Sciences, vol. 795, pp. xiii–xix, 1996.

Herrman and Abdi, *Both IL–2 and IL–4 Synergize with IL–12 to Induce a CTL Response, a Response Completely Blocked by TGF–β*, Annals of the New York Academy of Sciences, vol. 795, pp. 168–179, 1996.

Bennett and Perussia, *Effects of IL–12 on Human Natural Killer Differentiation*, Annals of the New York Academy of Sciences, vol. 795, pp. 181–188, 1996.

Tahara et al., *Murine Models of Cancer Cytokine Gene Therapy Using Interleukin–12$^{\alpha}$*, Annals of the New York Academy of Sciences, vol. 795, pp. 275–283 1996.

Wigginton et al., *Evaluation of the Antitumor Activity of the Interleukin–12/Pulse Interleukin–2 Combination$^{\alpha}$*, Annals of the New York Academy of Sciences, vol. 795, pp. 434–439, 1996.

Georgiades and Fleischmann, Jr., *Oral Application of Cytokines*, Biotherapy, vol. 8, pp. 205–212, 1996.

Burke and Balkwill, *Cytokines in Animal Models of Cancer*, Biotherapy, vol. 8, pp. 229–241, 1996.

Van der Meide and Schellekens, *Cytokines and the Immune Response*, Biotherapy, vol. 8, pp. 243–249, 1996.

Falkenberg, *Cancer Vaccines*, Cancer Research Institute International Symposium, Oct. 1996.

Edmondson and Druce, *5 Probability and Hypothesis Testing*, Advanced Biology Statistics, pp. 60–63, 1996.

Allison, *The Role of Cytokines in the Action of Immunological Adjuvants*, Vaccine Design: The Role of Cytokine Networks, Plenum Press, pp. 1–9, 1997.

Cox et al., *Development of an Influenza–Iscom™ Vaccine*, Vaccine Design: The Role of Cytokine Networks, Plenum Press, pp. 33–49, 1997.

Snippe et al., *Adjuvant Directed Immune Specificity at the Epitope Level: Implications for Vaccine Development a Model Study Using Semiliki Forest Virus Infection of Mice*, Vaccine Design: The Role of Cytokine Networks, Plenum Press, pp. 155–166. 1997.

Tagliabue and Boraschi, *Interleukin 1 and Its Synthetic Peptide 163–171 as Vaccine Adjuvants*, Vaccine Design: The Role of Cytokine Networks, Plenum Press, pp. 167–173, 1997.

Gursel and Gregoriadis, *The Immunological Co–Adjuvant Action of Liposomal Interleukin–15*, Vaccine Design: The Role of Cytokine Networks, Plenum Press, pp. 175–180, 1997.

Shurin et al., *Antitumor Activities of IL–12 and Mechanisms of Action*, Chem. Immunol., vol. 68, pp. 153–174, 1997.

Janovic et al., *Adsorption to Aluminum Hydroxide Promotes the Activity of IL–12 as an Adjuvant for Antibody as Well as Type 1 Cytokine Responses to HIV–1 gp120*, The Journal of Immunology, 159:2409–2417, 1997.

Weir and Stewart, *Immunity, Immunology*, Chpt. 1, pp. 3–15, 1997.

Weir and Stewart, *Antigens and Antigen Recognition, Immunology*, Chpt. 3, pp. 33–85, 1997.

Weir and Stewart, *Acquired Immunity, Immunology*, Chpt. 4, pp. 86–146, 1997.

Weir and Stewart, *Malignant Disease, Immunology*, pp. 258–266, 1997.

Leffell, *An Overview of the Immune System: The Molecular Basis for Immune Responses*, Handbook of Human Immunology, Chpt. 1, pp. 1–45, 1997.

Detrick and Hooks, *Cytokines in Human Immunology*, Handbook of Human Immunology, Chpt. 7, pp. 233–266, 1997.

Hünig and Schimpl, *The IL–2 Deficiency Syndrome*, Contemporary Immunology: Cytokine Knockouts, Chpt. 1, pp. 1–19, 1998.

Luftig, *Immunoprophylaxis*, Microbiology and Immunology, pp. 228–229, 1998.

Oppenheim, *Foreword*, The Cytokine Handbook, 3rd ed., pp. xviii–xxii, 1998.

Vilcek, *The Cytokines: An Overview*, The Cytokine Handbook, 3rd ed., Chpt. 1, pp. 1–20, 1998.

Duff, *Molecular Genetics of Cytokines*, The Cytokine Handbook, 3rd ed., Chpt. 2, pp. 21–33, 1998.

Gaffen et al., *Interleukin–2 and the Interleukin–2 Receptor*, The Cytokine Handbook, 3rd ed., Chpt. 4, pp. 73–103, 1998.

Wadhwa and Thorpe, *Assays for Cytokines*, The Cytokine Handbook, 3rd ed., Chpt. 31, pp. 855–884, 1998.

Tsai et al, *Induction of Antitumor Immunity by Interleukin–2 Gene–Transduced Mouse Mammary Tumor Cells Versus Transduced Mammary Stromal Fibroblasts*, Journal of the National Cancer Institute, vol. 85, No. 7, pp. 546–553, 1993.

Waldmann, *The IL–2/IL–2 Receptor System: A Target for Rational Immune Intervention*, Immunology Today, vol. 14 No. 6, pp 264–270, 1993.

Colombo and Forni, *Cytokine Gene Transfer in Tumor Inhibition and Tumor Therapy: Where Are we Now?*, Immunology Today, vol. 15 No. 2, pp. 48–51, 1994.

Kaplan, *Autocrine Secretion and the Physiological Concentration of Cytokines*, Immunology Today, vol. 17 No. 7, pp. 303–304, 1996.

Qin and Blankenstein, *Influence of Local Cytokines on Tumor Metastasis: Using Cytokine Gene–Transfected Tumor Cells As Experimental Models*, Attempts to Understand Metastasis Formation III, Therapeutic Approaches for Metastasis Treatment, pp. 55–64, 1996.

Soiffer et al., *Vaccination With Irradiated Autologous Melanoma Cells Engineered to Secrete Human Granulocyte–Macrophage Colony–Stimulating Factor Generates Potent Antitumor Immunity in Patients With Metastatic Melanoma*, Proc. Natl. Acad. Sci., vol. 95, pp. 13141–13146, Oct. 1998.

Peters et al., *Preparation of Immunotherapeutic Autologous Tumor Cell Vaccines From Solid Tumors*, Cancer Research, vol. 39, pp 1353–1360, 1979.

Cassel et al., *A Phase II Study on the Postsurgical Management of Stage II Malignant Melanoma With a Newcastle Disease Virus Oncolysate*, Cancer, vol. 52, pp. 856–860, 1983.

Tallberg and Tykka, *Specific Active Immunotherapy in Advanced Renal Cell Carcinoma: Clinical Longterm Follow–up Study*, World J. Urology, vol. 3, pp. 234–244, 1986.

Schirmacher et al., *Successful Application of Non–Oncogenic Viruses for Antimetastatic Cancer Immunotherapy*, Cancer Review, vol. 5, pp. 19–49, 1986.

Forni et al., *Interleukin 2 Activated Tumor Inhibition in Vivo Depends on the Systemic Involvement of Host Immunoreactivity*, The Journal of Immunology, vol. 138 No. 11, pp. 4033–4041, 1987.

Karasuyama and Melchers, *Establishment of Mouse Cell Lines Which Constitutively Secrete Large Quantities of Interleukin 2, 3, 4, or 5, Using Modified cDNA Expression Vectors*, Eur. J. Immunol., vol. 18, pp. 97–104, 1988.

Clayman, *Immunization*, The American Medical Association Encyclopedia of Medicine, pp. 573–576, 1989.

Clayman, *Immunization*, The American Medical Association Encyclopedia of Medicine, p. 1034, 1989.

Ley et al.,*A Novel Approach to the Induction of Specific Cytolytic T Cells In Vivo*, Res. Immunol., vol. 141, pp 855–863, 1990.

Schirrmacher et al., *Specific Eradication of Micrometastases by Transfer of Tumour–Immune T Cells From Major–Histocompatibility–Complex Congenic Mice*, Cancer Immunology Immunotherapy, vol. 32, pp. 373–381, 1991.

Malik et al., *Cells Secreting Tumour Necrosis Factor Show Enhanced Metastasis in Nude Mice*, Eur. J. Cancer, vol. 26, No. 10, pp. 1031–1034, 1990.

Schirrmacher, *Immunity and Metastasis: In situ Activation of Protective T Cells by Virus Modified Cancer Vaccines*, Cancer Surveys, vol. 13, pp. 129–154, 1992.

Pardoll, *New Stratagies for Active Immunotherapy With Genetically Engineered Tumor Cells*, Current Opinion in Immunology, vol. 4, pp. 619–623, 1992.

Sobol et al., *Cytokine Gene Therapy: Active Tumor Immunotherapy With Transduced Fibroblasts*, Proceedings of the American Association for Cancer Research, vol. 33, No. 2957, p. 495, 1992.

Bomford et al. *The Control of the Antibody Isotype Response to Recombinant Human Immunodeficiency Virus gp 120 Antigen by Adjuvants*, Aids Research and Human Retroviruses, vol. 8, No. 10, pp. 1765–1771, 1992.

Ohe et al., *Combination Effect of Vaccination With IL2 and IL4 cDNA Transfected Cells on the Induction of a Therapeutic Immune Response Against Lewis Lung Carcinoma Cells*, Intl. J. Cancer, vol. 53, pp. 432–437, 1993.

Anderson et al., *Cytokines in Liposomes: Preliminary Studies With IL–1, IL–2, IL–6, GM–CSF and Interferon–γ*, Cytokine, vol. 6, No. 1, pp. 92–101, 1994.

Ohira et al., *Gene Therapy for Lewis Lung Carcinoma With Tumor Necrosis Factor and Interleukin 2 cNDAs Co–transfected Subline*, Gene Therapy, vol. 1, pp. 269–275, 1994.

Ostrand–Rosenberg, *Tumor Immunotherapy: The Tumor Cell as an Antigen–Presenting Cell*, Current Opinion in Immunology, vol. 6, pp. 722–727, 1994.

Kedar et al., *Delivery of Cytokines by Liposomes. I. Preparation and Characterization of Interleukin–2 Encapsulated in Long–Circulating Sterically Stabilized Lipsomes*, Journal of Immunotherapy, vol. 16, pp. 47–59, 1994.

Wahl et al., *Generation of Therapeutic Lymphocytes After In Vivo Tumor Transfection With an Allogeneic Class I Major Histocompatibility Complex Gene*, Journal of Immunotherapy, vol. 17, pp. 1–11, 1995.

Gombotz and Pettit, *Biodegradable Polymers for Protein and Peptide Drug Delivery*, Bioconjugate Chem., Reviews, vol. 6, pp. 332–351, 1995.

Falkenberg and Reimer, *Liposome Encapsulated Cytokines Covalently Coupled to Tumor Cells: An Alternative to Gene–Transfected Tumor Cells as Vaccines?*, Vaccine Research, vol. 4, No. 2, pp. 105–111, 1995.

Souberbielle et al., *Comparison of IL–2– and IL–4–Transfected B16–F10 Cells With a Novel Oil–Microemulsion Adjuvant for B16–FG10 Whole Cell Tumour Vaccine*, Gene Therapy, vol. 3, pp. 853–858, 1996.

Simons et al., *Bioactivity of Autologous Irradiated Renal Cell Carcinoma Vaccines Generated by ex Vivo Granulocyte–Macrophage Colony–Stimulating Factor Gene Transfer, Cancer Research*, vol. 57, pp. 1537–1546, 1997.

Cox and Coulter, *Adjuvants—A Classification and Review of Their Modes of Action, Vaccine*, vol. 15, No. 3, pp. 248–256, 1997.

Thorpe, *Interleukin–2, Cytokines*, Academic Press, pp. 19–33, 1998.

Thorpe, *Summary Tables, Cytokines*, Academic Press, pp. 526–527, 1998.

Falkenberg et al., *Cytokine–Depot–Tumor–Vaccines: The Proper Cytokine Dose—A Question of Life and Death, Cancer Research Institute*, International Symposium, Oct. 1998.

Falkenberg and Krup, *Vaccination Against the Mouse B16 Melanoma: Irradiated Tumor Cells Mixed with Liposome–Encapsulated IL–2 as an Alternative to IL–2 Gene Transfected Tumor Cells, Skin Cancer and UV Irradiation*, pp. 1242–1249, 1997.

Dorigo et al., *Combination of Transforming Growth Factor β Antisense and Interleukin–2 Gene Therapy in the Murine Ovarian Teratoma Model, Gynecologic Oncology*, vol. 71(2), pp. 204–210, 1998.

Fakhrai et al., *Construction and Characterization of Retroviral Vectors for Interleukin–2 Gene Therapy, Journal of Immunotherapy*, vol. 20(6), pp. 437–448, 1997.

Shawler et al., *Comparison of Gene Therapy With Interleukin–2 Gene Modified Fibroblasts and Tumor Cells in the Murine CT–26 Model of Colorectal Carcinoma, Journal of Immunotherapy*, vol. 17(4), pp. 201–208, 1995.

Fakhrai et al., *Cytokine Gene Therapy With Interleukin–2–Transduced Fibroblasts: Effects of IL–2 Dose on Anti–Tumor Immunity, Human Gene Therapy*, vol. 6(5), pp. 591–601, 1995.

Sobol et al., *Interleukin–2 Gene Therapy in a Patient With Glioblastoma, Gene Therapy*, vol. 2(2), pp. 164–167, 1955.

Sobol et al., *Injection of Colon Carcinoma Patients With Autologous Irradiated Tumor Cells and Fibroblasts Genetically Modified to Secrete Interleukin–2 (Il–2): A Phase I Study, Human Gene Therapy*, vol. 6(2), pp. 195–204, 1995.

\* cited by examiner

COMPOSITIONS AND METHODS FOR TREATMENT OF TUMORS AND METASTATIC DISEASES

RELATED APPLICATION

The present application is a continuation-in-part of U.S. application Ser. No. 08/538,730 filed on Oct. 3, 1995.

BACKGROUND OF THE INVENTION

1. The Field of the Invention

The present invention is directed generally to methods and compositions for active specific immunotherapy of tumors. More specifically the present invention is related to methods and compositions for treating tumors with vaccines and with preparations for intratumoral injections and to methods for preparing tumor vaccines and preparations for intratumoral injections that are capable of stimulating immune responses to specific tumor antigens.

2. The Relevant Technology

Basic terminology and general principles in immunology. The foundation of immunology theory rests on the basic idea of self/non-self discrimination, a process that is accomplished by means of recognition mechanisms. Because these recognition mechanisms are used for defeating undesirable microorganisms and for eliminating potentially harmful substances, they are in fact a preeminent part of an individual's defense mechanisms.

Some of these defense mechanisms do not rely on the triggering effect of prior exposure for effecting their protective activity. These are part of the innate or natural immune mechanisms that include physical barriers like the skin, and certain substances, cells and enzymes that are active before exposure to foreign agents. In contrast, the defense mechanisms collectively known as acquired or adaptive immunity can recognize foreign structures and subsequent exposure to such foreign structures leads to a more efficient and effective immune response. See, for example, Donald M. Weir, and John Stewart, *Immunology*, chapter 1, 8th ed., Churchill Livingstone, New York, 1997. (This book will hereinafter be referred to as "*Immunology*").

A molecule that elicits a specific immune response when introduced into the host tissues is an antigen. Note that the definition of an antigen is arbitrary because specific responsiveness is a property of the host tissues, not of the injected substance. A response to stimulation by antigen is the production of an antibody, a protein that is capable of specific combination with antigen. See, for example, *Immunology*, chapter 3; *The Dictionary of Immunology*, edited by W. John Herbert, Peter C. Wilkinson, and David I. Scott, page 10, Academic Press, London, 1995. (This book will hereinafter be referred to as "*Dictionary of Immunology*"). The response of the host to an antigen on the first encounter is termed the primary immune response. *Dictionary of Immunology*, at p. 132.

The self/non-self discrimination idea in immunology should not be confused with the external/internal dichotomy. It is worth emphasizing in this respect that the physiological reaction that develops through an antibody response is triggered by a foreign agent, whether this agent is harmful or not. In addition, the foreign agent does not necessarily have to be external, for immune responses can also be generated against internal antigens. Sources of such internal antigens include antigens released from disintegrating tissues and antigens that are produced during replicative cycles. Immunity is achieved when the necessary antigen is present and induced antibodies can neutralize the foreign agent. See, for example, *Immunology* at pp. 86–87. Humoral immunity depends on the appearance in the blood of proteins such as those known as antibodies.

For self-non-self discrimination, especially in the context of tumor immunology, cellular immunity is much more important than antibodies. Cellular immunity, also known as cellular cytotoxic immunity or cell-mediated immunity, was originally used to describe localized reactions to organisms mediated by a type of lymphocytes, the T-lymphocytes, and by phagocytes rather than by antibody. It is currently used to describe any response in which antibody plays a subordinate role. It is acknowledged that cell-mediated immunity depends mainly on the development of T-cells that are specifically responsive to the inducing agent, and furthermore cell-mediated immunity is generally active against intracellular organisms. See, *Immunology*, pp. 86–87.

Adjuvants. The natural ability of an antigen to induce an immune response can be modified, and in particular enhanced, by altering or by mixing it with another substance. The procedure or the substance used to enhance immune responses is called an adjuvant. At least three classes of adjuvants have been used for a long time; these are mineral oil emulsions, aluminum compounds, and surface active materials such as saponin, lysolecithin, retinal, Quil A®, some liposomes, and pluronic polymer formulations. See, for example, *Fundamental Immunology*, edited by William E. Paul, at p. 1008, Raven Press, New York (this book will hereinafter be referred to as "*Fundamental Immunology*"). Aluminum adjuvants used alone or in combination include aluminum hydroxide gel, aluminum phosphate, aluminum sulphate, and alums comprising ammonium alum (such as $(NH_4)_2SO_4 \cdot Al_2(SO_4)_3$) and potassium alum. Aluminum hydroxide (hereinafter "AL") is one of the older adjuvants and it is considered so safe that it has been applied in bacterial and viral vaccines administered to billions of people around the world. Calcium phosphate gel (hereinafter "CP") has similar properties and is also used in vaccines. Both substances are available in pharmaceutical qualities in most countries worldwide. Techniques for preparing adjuvant-antigen preparations for injection are well known in the art. See, for example, Terry M. Phillips, *Analytical Techniques in Immunochemistry*, pp. 307–10, Marcel Dekker, New York, 1992.

Other adjuvants include complete Freund's adjuvant (a water-in-oil emulsion in which killed, dried, mycobacteria—usually M tuberculosis—are suspended in the oil phase); incomplete Freund's adjuvant (analogous to the complete Freund's adjuvant with no mycobacteria); ISCOM (or immune stimulating complex, comprising lipophilic particles formed by the spontaneous association of cholesterol, phospholipid and the saponin Quil A®); lipopolysaccharide (complex molecules consisting of a lipid core—lipid A—with a polysaccharide side chain that are components of certain bacilli, Lipid A is incorporated into the outer membrane of the bacterium and the polysaccharide projects extracellularly. Their adjuvant potency is associated with lipid A; they are also mitogenic for murine B lymphocytes); and mycobacterial adjuvants (whole, heat killed, dried, mycobacteria—such as *M. tuberculosis, M. avium, M. phlei*, and *M. smegmatis*) that, when suspended in mineral oil and emulsifier, have adjuvant activity with respect to any antigen given with them. Extracts of some mycobacteria, e.g., mycobacterial peptidoglycolipids have similar adjuvant activities. See, for example, *Dictionary of Immunology* at pp. 3, 7, 46, 94, 97, 105, and 116; R. B. Luftig, *Microbiology and Immunology*, pp. 228–29, Lippincott-Raven Publishers, Philadelphia 1998. Microbial adjuvants include *Corynebacterium parvum* and *Bordetella pertussis*. See, for example, *Handbook of Immunology* at 115–16. Use of controlled-release preparations and materials with adjuvant activity and possible sites of action have been described in *Fundamental Immunology* at pp. 1007–09.

Mineral carriers such as aluminum hydroxide, potassium ammonium sulphate, and potassium aluminum sulphate adsorb the antigen on their surface. These common adjuvants have been used at a 0.1% concentration with up to 1 mg protein antigen in 1 ml administered to animals at doses of 0.2–0.5 ml/(kg body weight). See Miroslav Ferencik, *Handbook of Immunochemistry*, p. 115, Chapman & Hall 1993 (this book will hereinafter be referred to as "Handbook of Immunochemistry"). Although Freund's adjuvant is toxic and not used for immunization of human beings, mineral adjuvants such as aluminum hydroxide are common in human medicine. Id. at 116. In addition to alum, other adjuvants in the group of inert carriers include bentonite, latex, and acrylic particles. See *Fundamental Immunology* at 1008.

Combinations of adjuvants can also have adjuvant properties. For example, it has been shown that the combination of saponin and muramyl dipeptide in a squalene in water emulsion is superior to alum as an adjuvant for inducing certain responses in mice. R. Bomford, M. Stapleton, S. Wilson, A. McKnight, and T. Andronova, The control of the antibody isotype responses to recombinant human immunodeficiency virus gp120 antigen by adjuvants, *AIDS Res. Hum. Retroviruses* Vol. 8(1992) pp. 1765 et seq. These adjuvants are complemented by new adjuvants that have been developed during the last fifteen years. See, for example, Anthony C. Allison, The Role of cytokines in the Action of Immunological Adjuvants, in Vaccine Design. *The Role of cytokine Networks*, edited by Gregory Gregoriadis and Brenda McCormack, NATO ASI Series A: Life Sciences Vol 293, pp. 1–9, Plenum Press, New York 1997 (this book will hereinafter be referred to as "Vaccine Design"); *Immunology* at p. 116; H. Snippe, I. M. Fernandez and C. A. Kraaijeveld, Adjuvant Directed Immune Specificity at the Epitope Level. Implicationsfor Vaccine Development. A Model Study Using Semliki Forest Virus Infection of Mice, in *Vaccine Design* at pp. 155–73.

An adjuvant can be administered prior to, simultaneously with, or following the administration of the antigen. Antibody production enhancement caused by adjuvants is not fully understood. However, adjuvant properties that may exist either alone or in various combinations and which permit a substance or formulation to be described as adjuvant active have been defined. See, for example, J. C. Cox and A. R. Coulter, Adjuvants—A classification and review of their modes of action, *Vaccine* Vol. 15(1981) pp. 248 et seq.; John Cox, Alan Coulter, Rod Macfarlan, Lorraine Beezum, John Bates, Tuen-Yee Wong and Debbie Drane, Development of an Influenza-ISCOM™ Vaccine, in *Vaccine Design* at pp. 33–49. One of these properties is depot generation, whereby the vaccine is retained near the dose site to give short term trickle release or a longer term pulsed release. Id. at 34. The term "depot" will hereinafter be used to refer to an adjuvant or to the combination of an adjuvant and at least one immunostimulating substance that is administered with antigenic material for enhancing the immune response.

Lymphocytes and cytokines. The immune system in the higher animals comprises a collection of organs and cell types, and all these cells develop from stem cells in tissues such as the bone marrow. One of these types of cells in particular, the white blood cells or leucocytes, are produced through two main pathways of differentiation. More specifically, the lymphoid lineage is the differentiation pathway that leads to the production of T-lymphocytes (also known as T cells) and B-lymphocytes, collectively lymphocytes. These are cells that are found, inter alia, at sites where immune responses are taking place. More specifically, a lymphocyte is an antigen-receptor carrying cell that recognizes the antigen, effectively embodying a mediator cell of specific immunity. See, for example, *Immunology* at pp. 8–9, *Dictionary of Immunology* at pp. 107, 147.

In addition to cells, many secreted molecules, known as cytokines, play a role in the different phases and aspects of immune responses. Cytokines are usually glycoproteins made and secreted by cells and they act as cellular mediators with effects on the same or other cells' characteristics such as growth, differentiation, and activation. More generally, cytokines are defined as regulatory peptides that can be produced by virtually every nucleated cell type in the body. See, for example, Joost J. Oppenheim, Foreword, in *The Cytokine Handbook*, edited by Angus Thomson, pp. xviii–xxii, Academic Press, Norfolk, UK 1998 (this book will hereinafter be referred to as "*Cytokine Handbook*"); Barbara Detrick and John J. Hooks, *Cytokines in Human Immunology*, in *Handbook of Human Immunology*, edited by Mary S. Leffell, Albert D. Donnenberg, and Noel R. Rose, pp. 233–66, CRC Press, Boca Raton, Florida 1997 (this book will hereinafter be referred to as "*Human Immunology Handbook*"). The term interleukin (hereinafter abbreviated as "IL") is part of the designations of a number of cytokines. See, for example, Jan Vilcek, The Cytokines: An Overview, in *Cytokine Handbook*, pp. 1–33.

It is currently suspected that some cytokines such as the Colony Stimulating Factors ("CSF"), might have some properties that relate to long-range effects in addition to the shortrange effects that are acknowledged as more typical of cytokines. Nevertheless, the main function of most cytokines appears to be paracrine, this term referring to the signaling to or attracting of other lymphocytes in proximity. Some cytokines, and in particular IL-2, also have an autocrine function, this term referring to self stimulation that is derived from the cytokine binding to receptors on the same cell that previously secreted the cytokine.

The name interleukin is given to certain cytokines that act as intercellular signals. Nevertheless, it is accepted that there is no logic to the interleukin designation and there is no logic to the order in which the interleukins are numbered either. For example, cytokines such as certain interferon or tumor necrosis factor could also be designated with the term interleukin. *Dictionary of Immunology*, at p. 96. As of 1996, the interleukin series had reached 18. *Cytokine Handbook*, at p. 3.

The cytokines that are produced by lymphocytes are termed lymphokines and their release is often stimulated following contact with antigens. Cytokines such as IL-2 and IL-4 are lymphokines. IL-2's major function is in the regulation of the immune response. See, for example, *Immunology*, at pp. 86–146. Background material on IL-2 can be found in, for example, Kendall A. Smith, Interleukin-2: Inception, Impact, and Implications, Science Vol. 240 (1988), pp. 1169–76; Sarah L. Gaffen, Mark A. Goldsmith, and Warner C. Greene, Interleukin-2 and the Interleukin-2 Receptor, in *Cytokine Handbook* at pp. 73–103; Christopher J. Secombes, The Phylogeny of Cytokines, in Cytokine Handbook at pp. 965–71; Interleukin-2, edited by Kendall A. Smith, Academic Press, San Diego, Calif. 1988 (this book will hereinafter be referred to as "Interleukin-2"); Robin Thorpe, Interlekin-2 in *Cytokines*, edited by Anthony Mire-Sluis and Robin Thorpe, pp. 19–33, 526–27, Academic Press, San Diego, Calif. 1998 (this book will hereinafter be referred to as "*Cytokines*"). Background material on other interleukins can be found in, for example, *Cytokine Handbook* at pp. 35–72, 105–499, and background material on other cytokines can be found in, for example, *Cytokine Handbook* at pp. 491–823, 885–993, and in *Cytokines* at pp. 1–18, 35–546. It is acknowledged that no short definition can encompass all the essential properties of cytokines, which are better defined by a set of characteristic features. See, for example, *Cytokine Handbook* at p. 4. Despite the existence of these characteristic features, individual cytokines, and in particular individual interleukins, fall into different families when they are classified according to features such as structure, receptors, and stimulatory and inhibitory actions. Furthermore, a plurality of synergistic and antagonistic interactions among cytokines have been reported. See, for example, *Cytokine Handbook* at pp. 6–14.

Methods for the measurement and detection of cytokines are described in, for example, Meenu Wadha and Robin Thorpe, *Assays for Cytokines*, in *Cytokine Handbook* at pp. 855–84. IL-2, formerly known as T cell growth factor, is an immunostimulant. More precisely, by the application of IL-2 the immune system can be stimulated to become active against tumor cells. Production and characteristics of natural and recombinant human IL-2 have been described by K. Kato, Characteristics of Natural and Recombinant Human Interleukin 2, in *Interleukin-2* at pp. 37–66 and references therein. It is known that recombinant human IL-2 reacts in the same manner in human beings as it does in mice.

Immunomodulators, of ten contained in adjuvants, induce the production of cytokines, thus enhancing immune responses. Examples are muramyl peptides, lipopolysaccharides and derivatives, and certain cationic detergents. See, for example, Anthony C. Allison, The Role of Cytokines in the Action of Immunological Adjuvants, in Vaccine Design at pp. 1–9. Interleukin active domains or the corresponding synthetic peptides could in fact be potent adjuvants, as shown for a region of an IL-1. See, for example, Aldo Tagliabue and Diana Boraschi, Interleukin 1 and Its Synthetic Peptide 163–171 as Vaccine Adjuvants, in Vaccine Design at pp. 167–73.

Immunization and Immunology. Specific immunity is generally understood as a developed non-susceptibility to re-infection by a pathogen, thus implying survival after prior exposure to the same pathogen. In other words, specific immunity results from the recognition of antigen/cell that leads to the production of specific antibody and/or the stimulation T-lymphocytes that subsequently specifically react with the recognized antigen/cell. See, for example, *Dictionary of Immunology* at 147.

It follows from the foregoing Concise overview of basic terminology and concepts in immunology that acquiring immunity to threatening agents is a desirable goal in an organism's overall defense strategy. Immunization provides the line of defense that relies on acquired immunity. The mechanism of this form of immunity involves the contact between the antigens of the invading agent and the immune system cells, including lymphocytes, followed by an immune response that is specific to the foreign agent.

Immunization is the process by which specific immunity is induced as a preventive measure in the fight against many diseases. Immunization is a general term, and the term vaccination is used when patients are immunized. In general, immunization can be used as a preventive or as a therapeutic treatment. The preventive use of immunization is a prophylactic treatment, whereas the use of immunization while the disease is in progress is immunotherapy. Immunization provides two types of acquired immunity, active and passive. Immunotherapy is the treatment of a disease by immunization, active or passive, or by the use of agents that modify the actions of lymphocytes. In particular, immunotherapy refers to the stimulation of the immune system and conventionally uses a form of immunostimulant, a substance that causes a general, non-specific, stimulation of the immune system. The *American Medical Association Encyclopedia of Medicine*, p. 576 (this encyclopedia will hereinafter be referred to as "AMA Encyclopedia of Medicine").

Passive immunization involves the transfer of pre-formed antibodies that provide immediate, short lived, protection against specific disease-causing cells. Passive vaccination typically involves the administration of either serum of an immune individual into another individual that might be infected, or antibodies that are purified from such toxin-immune sera. Active immunization primes the body to make its own antibodies against disease causing agents/cells and confers longer lasting immunity. This priming can be accomplished by overt clinical infection, inapparent infection or deliberate artificial immunization. Whereas low levels of antibody are characteristically produced slowly during the primary immune response, priming of the tissues in which the predominant cells are lymphocytes or lymphoid tissues allows a secondary immune response to be evoked on or subsequent challenge. When the secondary immune response takes place, there is a very rapid production of large amounts of antibody over a few days followed by a slow exponential fall. This pattern is common to a plurality of immune response mechanisms. See, for example, *Dictionary of Immunology*, at pp. 142.

Vaccination is a form of deliberate artificial immunization whereby antigenic material, or vaccine, is administered. The administered antigens can be in the form of killed or weakened cells that sensitize the immune system such that if disease causing cells with the same antigen later enter the body, they are quickly destroyed. See, for example, *Immunology*, at pp. 87–88; *AMA Encyclopedia of Medicine* at 573–574 and 1034; S. J. Cryz, Jr., in *Immunotherapy and Vaccines*, edited by Stanley J. Cryz, pp. 3–11, VCH, Weinheim, Germany 1991. For an overview of the immune system from a molecular perspective, see, for example, Mary S. Leffell, An Overview of the Immune System: The Molecular Basis for Immune Responses, in *Human Immunology* Handbook pp. 1–45.

In general, the following materials are used for vaccination: live bacteria or viruses (dangerous, e.g., variola vacciniae against smallpox); killed bacteria or viruses (sometimes with dangerous side effects); weakened viruses (e.g., for vaccination against poliomyelitis); attenuated bacteria or viruses (similar to weakened viruses); viruses that affect animals and make them sick or kill them but that are harmless to humans or just make them slightly sick, such as the vaccinia cowpox virus; parts of bacteria such as antigens and membrane fractions, also known as cellular vaccines, which are much safer but sometimes not as effective (e.g., Bordetella pertussis), and if bacteria are pathogenic due to the toxins that they release, then toxoids or inactivated toxins can be used in vaccination (e.g., Diphtheria toxin and tetanus toxin (from clostridium tetani)).

Sometimes the antibodies and cells that are induced against an animal virus also react with a similar human virus. The immune response is then termed cross-reactive. For example, the immune response induced against cowpox virus, which is genetically similar to the human pathogenic smallpox virus, is cross-reactive.

When any biological activity of the antigenic material to be administered is destroyed prior to its administration, the antigenic material is incapable of replication, the vaccine that contains such material is called an inactivated vaccine, and the destructive process is called inactivation. For example, irradiation of cells with an appropriate dose of X-rays of fers one way of inactivating the disease-causing aspects of the irradiated cells while they retain their antigenicity and morphology. The cells so irradiated are thus capable of promoting an immune response, but they are not capable of causing disease. In contrast, a live vaccine that contains organisms or viruses that have been cultured or otherwise treated under conditions in which they lose virulence but retain the capacity to stimulate an immune response is called an attenuated vaccine and the process that renders the antigenic material under such conditions is called attenuation. Attenuation reduces the ability to cause disease, but it does not significantly alter antigenicity. See, for example, *Dictionary of Immunology*, at pp. 17, 93.

Immunology and cancer prevention and therapy. Historical records reveal that strategies for acquiring immunity against threatening agents have been pursued for a long time, although with varying degrees of understanding of the mechanisms involved. In particular, records of certain forms of immunization have been traced back to the sixth century in China, where at least immunization against smallpox was practiced at about AD 590 and it has been reported that this form of immunization was also practiced in India in ancient times. See, for example, *Immunology* at 4–5. With an ever increasing understanding derived from the intense use of modern clinical and biochemical research tools, immunization is actively pursued; acquiring immunity against certain threatening agents is viewed nowadays as one of the potentially more successful means for defeating such agents. See, for example, Philip Livingston, Conference Overview, in Specific Immunotherapy of Cancer With Vaccines, edited by Jean-Claude Bystryn, Soldano Ferrone, and Philip Livingston, Annals of the New York Academy of Sciences Vol. 690, pp. 1–5, New York 1993 (this publication will hereinafter be referred to as "*Immunotherapy of Cancer With Vaccines*"). One of the agents against which the effect of immunological preventive and therapeutic techniques have been incessantly studied is cancer. See, for example, Ingegerd Hellstrom and Karl Erik Hellström, *Tumor Immunology*: An Overview, in Immunotherapy of Cancer With Vaccines, at pp. 24–33.

A lesson learned from the use of vaccines against infectious diseases is that vaccines do not prevent infection; instead, they limit it. Once the vaccine has primed the immune system, natural systems and local immunity cure infection at the site of entry. If circulating tumor cells can be eliminated by the appropriate antibodies or by immune system cells, local treatment may cure cancer much like vaccination leads to the defeat of infectious diseases.

One of the problems presented by the treatment of human cancers with vaccines, however, is that the immunogenicity of tumor antigens is relatively low. Immunogenicity is the potential of an antigen to stimulate an immune response. In general, tumor antigens are not sufficiently immunogenic to induce more than occasional immune responses. *Immunotherapy of Cancer With Vaccines*, at p. 4. This fact notwithstanding, a tumor's low immunogenicity in standard immunization experiments does not necessarily mean that it lacks molecules that can, under appropriate conditions, be recognized as antigenically foreign. Concisely put, antigenicity is the capacity of a substance to act as an antigen and consequently, immunogenicity and antigenicity are separate characteristics. This difference is illustrated by the fact that antigenic tumors of ten escape immunologic control. Id. at pp. 26–27. In the context of this specification, "immunogenicity" is used to characterize tumor cells or proteins that are used for inducing immune responses and "antigens" describes materials used for testing, demonstrating or measuring immune responses. For an overview on immunity to tumors and tumor antigens see, for example, *Immunology* at 258–66.

The low immunogenicity of tumor antigens can be concisely and generally explained as follows. In contrast to bacteria or viruses, which invade the organism from the outside world, tumors are derived from the organism's own cells by mechanisms only partially understood today. Consequently, they bear surface structure, which is derived from the organism's repertoire of "self antigens" and they are tolerated by the host's defense systems. When such tumors have been growing in an organism for a long time (perhaps years or even decades) they develop an increasing number of foreign characteristics. This is due to the many cellular divisions that they undergo which in turn leads to a rather chaotic genetic organization. Tumors might therefore be eventually very different from the host's cells. However, due to their slow growth and other unknown factors, the host's immune system gets accustomed to the more and more foreign-looking tumor cells and it does not react to them. "Tumor-specific antigens" are a rarity. Only a few such antigens are known, among them the idiotypes of antibodies in the membranes of B lymphoma cells. Most of the tumor antigens are self-antigens or altered self-antigens, or antigens that belong to the repertoire of self-structures. In addition, tumors might expose antigens that have been expressed only during embryonal or fetal development and that might, therefore, be "unknown" to the immune system. These types of antigens include onco-fetal antigens and carcino-embryonal antigens, such as alpha fetoprotein (AFP) or carcino embryonic antigen (CEA). Tumor cells might also be weak antigens because they miss some of the normal antigenic structures that are needed to recognize a cell as foreign, such as the MHC antigens.

Active specific immunotherapy approaches to the treatment of tumors have been widely investigated during recent years. Numerous studies involving the vaccination of patients with their own inactivated tumor cells have been reported. These studies have demonstrated that inclusion of an adjuvant is necessary to stimulate the patient's immune system against the autologous, or derived from self, tumor cells. For example, methods utilizing the particulate adjuvant, Bacillus Calmette-Guerin (BCG) cells, administered systemically or mixed with the patient's own tumor cells have been shown to induce tumor-specific immunity in laboratory animals. Peters, L. C., Brandhorst, J. S., Hanna Jr., M. G., Preparation of Immuno-Therapeutic Autologous Tumor Cell Vaccines from Solid Tumors; Cancer Res. 39: 1353–1360 (1979).

This approach has been investigated with different tumor types. The administration of inactivated tumor cells in a mixture including a bacterial adjuvant resulted in significantly improved survival rates in patients with metastasized renal cell carcinoma. Tallberg, T., Tykkä, H., Specific Active Immunotherapy in Advanced Renal Cell Carcinoma: A Clinical Long-Term Follow-Up Study; World J Urology 3: 234–44 (1986). A statistically significant increase in patient survival rates was also achieved with the use of Newcastle Disease Virus (NDV) as an adjuvant in clinical trials for the treatment of malignant melanoma. Cassel, W. A., Murray, D. R., Phillip, H. S., A Phase II Study on The Post Surgical Management of Stage II Malignant Melanoma With a Newcastle Disease Virus Oncolysate, Cancer 52: 856–60 (1983). A similar protocol employed in animal tumor models demonstrated that administration of a vaccine prepared by irradiating ESb tumor cells infected with the apathogenic NDV induced permanent T-cell immunity towards antigens of the introduced tumor type. Schirrrnacher, V., Ahlert, T., Heicappel, R., Appelhans, B., Von Hoegen, P., Successful Application of Non-Oncogenic Viruses for Antimetastatic Cancer Immunotherapy; Cancer Reviews 5: 19–49 (1986); Schirrmacher, V., Immunity and Metastasis: In Situ Activation of Protective T Cells by Virus-Modified Cancer Vaccines; Cancer Survey 13: 139–154 (1992). Moreover, the immunity was transferable to other animals by adoptive transfer of lymphocytes. Schirrmacher, V. Von Hoegen, P. Griesbach, A., Zangemeister-Wittke, U., Specific Eradication of Micrometastasis by Transfer of Tumor-Immune T-Cells From MHC-Congenic Mice; Cancer Immunol. and Immunother. 32: 373–81 (1991).

NDV, however, is not a conventional adjuvant. During incubation with tumor cells the fowl-pathogenic and human apathogenic virus binds to the tumor cells and the virus membrane gets integrated into the tumor cells membrane which by this gets a certain degree of xenogenization. In addition, the virus membrane contains components (hemagglutinins) to which human (and animal) cells (lymphocytes) can bind. It is anticipated that the immune system is stimulated by the xenogenization of the tumor cell membranes altered by the interaction of the virus membrane. In addition, lymphocytes can bind to the hemagglutinin moiety the tumor cells have acquired from the virus and become stimulated upon binding. This might also render the otherwise non-immunogenic parts of the tumor cells more immunogenic.

Regarding the use of adjuvants in cancer treatment, one may think of using a substance with well-known adjuvant properties such as aluminum hydroxide. This substance is used in bacterial and viral vaccines for inducing humoral immunity, which is antibody-based immunity. However, it is acknowledged that the induction of humoral immunity responses is or can be counterproductive—depending on the type of tumor—in tumor therapy. It has been shown that antibodies to tumor antigens might mask the tumor antigens and thus protect the tumor from the desired aggression by T-lymphocytes and other immune system cells. Due to this known property of inducing immune responses that might even protect the tumor from the attack of the cellular immune system, most researchers have ignored aluminum hydroxide and have not investigated its properties as an adjuvant for tumor vaccines. Those who have investigated these properties in animal experiments have clearly shown that aluminum hydroxide in fact does not have adjuvant activity at all. See, B. E. Souberbielle, B. C. Knight, W. J. Morrow, D. Darling, M. Fraziano, J. B. Marriott, S. Cookson, F. Farzaneh, and A. G. Dalgleish, Comparison of IL-2 and IL-4-transfected B16-F10 cells with a novel oil-microemulsion adjuvant for B16-F10 whole cell tumor vaccine, *Gene Therapy* Vol. 3 (1996) 853–858. Consistently with this knowledge, some researchers have ceased using aluminum hydroxide in experimental tumor vaccination. In addition, it has been shown that aluminum hydroxide does not act as an adjuvant when injected together with tumor cells or when injected alone. This knowledge is supplemented by the already reported property of aluminum hydroxide as an adjuvant only for soluble protein or for carbohydrate antigens, not for cells.

Cytokines and cancer immunotherapy. Clinical trials with IL-2 have shown on the one hand that cytokines can stimulate immunity and lead to complete tumor regression in some patients. On the other hand, it has also been shown that systemic therapy with cytokines can be extremely toxic, thus limiting its effectiveness. See, for example, John A. Sogn, John F. Finerty, Anne K. Heath, Grace L. C. Shen, and Faye C. Austin, *Cancer Vaccines*: The Perspective of the Cancer Immunology Branch, NCI, in *Immunotherapy of Cancer With Vaccines* at p. 326. Furthermore, it is known that "determining the best cytokine or cytokines to use is difficult because so many cytokines have the potential to augment immunity and because virtually all of the cytokines tested in mice have shown some potential usefulness." Id. at p. 327.

It is known that administration of IL-2 to patients is of ten associated with adverse effects, sometimes so severe that the therapy must be halted. The complications include the development of severe vascular permeability which leads to interstitial pulmonary edema and eventual multiorgan failure if the therapeutic administration of IL-2 is not reduced or discontinued. A mouse study has characterized this condition and the IL-2-induced formation of certain products is believed to be involved in the process. Although less frequently, other adverse effects observed during or following the administration of IL-2 include cardiomyopathy, scleroderma, myelodysplasia, hypothyroidism, diabetes, renal disease, colonic ischemia, inflammatory arthritis, hypoprothrombinemia, fever, diarrhea, and asthemia. In addition, patients may develop antibodies against IL-2 that could compromise therapy. Given this sequel of adverse effects, it is acknowledged that "[t]herapeutic strategies, including dosing and route of administration, are largely influenced by attempts to limit adverse effects associated with IL-2 therapy". Robin Thorpe, *Interleukin*-2, in *Cytokines* at p. 27.

Cytokines have been reported as having generally potent effects on the development of the immune response to tumors and as eliciting a response capable of rejecting tumors. See, for example, A. McAdam, B. Pulanski, S. Harkins, E. Hutter, J. Frelinger, and E. Lord, Coexpression of IL-2 and γ-IFN Enhances Tumor Immunity, in *Immunotherapy of Cancer With Vaccines* at p. 349. Cytokines have also been used in vaccines for humoral immune responses. See, for example Dragana Jankovic, Patricia Caspar, Martin Zweig, Maria Garcia-Moll, Stephen D. Showalter, Frederick R. Vogel, and Alan Sher, Adsorption to Aluminum Hydroxide Promotes the Activity of Il-12 as an Adjuvant for Antibody as Well as Type 1 Cytokine Responses to HIV-1 gp 120, *The Journal of Immunology* Vol. 159 (1997) pp. 2409–17, at p. 2412. Although cytokines may play crucial roles in therapeutic vaccines for cancer treatment, these observations require a call for caution "because cytokines have as much potential to stimulate tumor growth as to retard it, and many cytokines effectively suppress immune responses under some conditions"; it is further acknowledged that these "complexities can only be unraveled by additional animal studies and direct testing in humans of promising candidate cytokines." John A. Sogn, John F. Finerty, Anne K. Heath, Grace L. C. Shen, and Faye C. Austin, *Cancer Vaccines*: The Perspective of the Cancer Immunology Branch, NCI, in *Immunotherapy of Cancer With Vaccines*, at p. 327.

In particular, numerous studies have utilized interleukin-2 (IL-2) in the form of recombinant IL-2 (hereinafter referred to as "rIL-2") which became available in therapeutically meaningful quantities as a result of genetic engineering techniques. Although systemic application of rIL-2 demonstrated promising therapeutic effects, severe and occasional lethal side effects were produced. Forni, G., Siovarelli, M., Santoni, A., Modesti, A., Forni, M., Interleukin-2 Activated Tumor Inhibition In Vivo Depends on the Systemic Involvement of Host Immunoreaetivity: J Immunol. 138: 4033–41 (1987); Waldmann, T. A., The IL-2/IL-2 Receptor System: A Target for Rational Immune Intervention; Immunol. Today 14: 264–70 (1993). In addition, the costs associated with this therapy can be very high.

The severe side effects may be due to the magnitude of the systemic doses of cytokines which must be administered to achieve the therapeutic benefits. Cytokines facilitate communication between cells. During such cell-to-cell communications, high concentrations are achieved at a localized cellular level but the concentration of circulating cytokines is typically very low. More specifically, if a lymphocyte meets a non-self antigen, for example, a tumor cell, it signals to other cells of the immune system about this encounter by secretion of cytokines. It was shown that the local concentration of IL-2 secreted by an activated T-lymphocyte is very high. The concentration of IL-2 in the secretory granules in which IL-2 is stored is in the range of 1–100 mM, which is a very high local concentration (equivalent to about 10–1000 g/l). See, D. R. Kaplan, Autocrine secretion and the physiological concentration of cytokines, *Immunology* Today Vol. 17 (1996) pp. 303–304. After release of IL-2 into the local environment, the local concentration remains very large, but this concentration is very small just a few cell diameters away from the release site. Consequently, a cytokine concentration gradient develops in the neighborhood of the cytokine release site, which is where the encounter with the antigen has taken place. Released cytokine molecules diffuse and finally reach the vascular system, where lymphocytes will detect the cytokine and migrate according to the cytokine concentration gradient towards regions with increasingly higher cytokine concentration, eventually reaching the site of the encounter with the antigen, invading it, secreting additional cytokines, and thus attracting greater numbers of lymphocytes to the site. This is in essence a chemotactic reaction of lymphocytes to cytokine concentration gradients.

Systemic delivery of a cytokine, however, results in "flooding" of the entire organism with concentrations which would normally be present only at a localized cellular level. Consequently, immune system cells cannot locate the source of the cytokines that were released upon reaction with the antigenic material, which may further lead to the suppression of the beneficial effects of cytokines or even to the failure of the immune system. Local administration of cytokines has been investigated with variable results. Local administration in the form of an inhaled spray for the treatment of lung metastases of renal cell carcinomas appears to permit sufficient quantities of cytokines to be retained in proximity to the tumor lesions. Other attempts to localized administration, however, have been less successful. Because of their small size, the cytokine molecules tend to diffuse away from the application site and into surrounding tissue or be carried away and diluted in body fluids. In addition, the very short half-life of cytokines in blood results in a very short period of activity.

Concisely, the administration of cytokines may lead to complications and deleterious effects. It is therefore desirable to find the dosage that can be tolerated by living beings without causing undesirable side effects.

Cancer immunotherapy and localized delivery of cytokines. Numerous attempts have been made to direct the immunostimulating activity of cytokines to the tumor site. Some of these attempts rely on transfection techniques, transfection being the artificial transfer of foreign DNA into a eukaryotic cell. In animal models, this local cytokine immunostimulating activity has been achieved through the method of transfecting cytokine encoding genes into the tumor cells thereby causing the tumor cells to produce and secrete the cytokines. Cytokine gene-transfected cells contain the cytokine source and also the source of the immunogenic material. Karasuyama, H., Melchers, F., Establishment of Mouse Cell Lines Which Constitutively Secrete Large Quantities of interleukin 2, 3, 4, or 5, Using Modified cDNA Expression Vectors; Eur. J. Immunol. 18: 97–104 (1988).

Additional research into this promising method has been performed involving most of the known cytokine genes and various animal tumor models, especially mouse models. Because intact viable tumor cells, capable of multiplying, are necessary for the expression of the transfected cytokine gene, this method requires the use of viable tumor cells in the vaccine. Following injection into the experimental animal, the viable cytokine-gene-transfected tumor cells initially replicate to form a tumor. Over a period of time, typically 1–2 weeks, however, the tumor begins to diminish and eventually disappears entirely. Appearance of systemic cytokine activity follows the same pattern. Animals subjected to this treatment subsequently demonstrate immunity to "re-infection" by tumor cells of the original genotype but not to other tumor types. See, e.g., Ley, V., Roth, C., Langlade-Demoyen, P., Larsson-Sciard, E. L., Kourilsky, P., A Novel Approach to the Induction of Specific Cytolytic T Cells In Vivo, Res. Immunol. 141: 855–63 (1990).

Further experiments have shown that immunity to non-transfected and, thus, non cytokine-producing, tumor cells can be induced by administering these tumor cells closely mixed with cytokine-producing tumor cells. Pardoll, D., New Strategies for Active Immunotherapy With Genetically Engineered Tumor Cells; Curr. Opin. Immunol. 4: 619–623 (1992). The induction of immunity appears to require that both the antigenic stimulus of the non-transfected tumor cells and the immunostimulus of the cytokine-producing cells originate from the same location within the experimental animal although not necessarily from the same cell. Further support for this theory arises from experiments in which immunity was induced by the administration of target tumor cells accompanied by nontransformed somatic cells, typically fibroblasts, transfected with a cytokine gene. See, e.g., Sobol, R. E., Fakhrai, H., Gjerset, R., Active Tumor Immunotherapy With Transduced Fibroblasts; Protocols Amer. Assn. Cancer Res. 33: 495–502 (1992).

Simultaneous exposure to multiple cytokines has been shown to be an especially effective method of inducing immunity with gene-transfected tumor cells. Vaccination of mice with a mixture of IL-2-gene-transfected and IL-4-gene-transfected tumor cells induced stronger immunity than vaccination with cells transfected with only one or the other of the cytokine genes. Ohe, Y. Podack, E. R., Olsen, K. J. et al., Combination Effect of Vaccination With IL-2 and IL-4 cDNA Transfected Cells on the Induction of a Therapeutic Immune Response Against Lewis Lung Carcinoma Cells; Intl. J. Cancer 52: 432–37 (1993). Tumor cells transfected with both IL-2 and Tumor Necrosis Factor (TNF) cytokines were more effective at inducing immunity than cells infected with only one of the two genes. Ohira, R., Ohe, Y., Heike, Y., Podack, E. R., Olsen, K. J., Nishio, K., Nishio, M., Miyahara, Y., Funayama, Y., Ogasawara, H., Arioka, H., Kato, H., Saijo, N., Gene Therapyfor Lewis Lung Carcinoma With Tumor Necrosis Factor and Interleukin-2 cDNAs Co-Transfected Subline; Gene Therapy 1: 269–275 (1994).

It is also known that lymphocytes obtained from cancer patients that were activated with IL-12 and IL-2 revealed greatly augmented cytotoxicity against autologous tumor cells compared with that induced by IL-2 alone. See, for example, Michael Shurin, Clemens Esche, Jean-Marie Peron, and Michael T. Lotze, Antitumor Activities of IL-2 and Mechanisms of Action, in *Chemical Immunology*, IL-12, edited by L. Adorini, K. Arai, C. Berek, J. D. Capra, A.-M. Schmitt-Verhulst and B. H. Waksman, Vol. 68 at pp. 153–74, Karger, Basel, Switzerland 1997.

It is known that Granulocyte-Macrophage Colony-Stimulating-Factor (hereinafter referred to as "GM-CSF") plays an essential role in induction of tumor immunity. GM-CSF is a cytokine that is made by a number of cells, including lymphocytes and it is necessary for differentiation of lineage-specific stem cells. B16 mouse melanoma cells which had been transduced with the genes for both IL-2 and GM-CSF induced stronger immunity to this tumor than any other cytokine-gene transfected Btumor cell. Dranoff, G., Jaffee, E., Lazenby, A., Golumbek, P., Levitsky, H., Brose, K., Jackson, V., Hamada, H., Pardoll, D., Mulligan, R. C., Vaccination With Irradiated Tumor Cells Engineered to Secrete Murine Granulocyte-Macrophage Colony-Stimulating-Factor Stimulates Potent, Specific, and Long-Lasting Anti-Tumor Immunity; Proc. Natl. Acad. Sci. USA 90: 3539–3543 (1993). The underlying molecular and cellular events are not entirely understood. It could be that GM-CSF released from the tumor cells is actively recruiting cells that are essential for primary immune responses, such as dendritic cells, and attracting these to the injection site or to the tumor cell itself. The dendritic cells then may take up antigen for presentation to T-lymphocytes attracted by cytokines released by the dendritic or other cells and/or by IL-2 released by the transfected tumor cells. Alternatively, or in addition, the dendritic cells may carry the tumor antigens to the regional lymph nodes and thereby expose the antigens to other immune system cells. It would appear that the natural immune response is more closely mimicked with vaccines incorporating the local release of two, or more, cytokines than by vaccines incorporating the release of only one cytokine.

Other experiments with IL-2 transfected tumor vaccines include those reported in Jerry A. Bash, Active Specific Immunotherapy of Murine Colon Adenocarcinoma with Recombinant Vaccinia/Interleukin-2-Infected Tumor Cell Vaccines, in *Immunotherapy of Cancer With Vaccines*, at pp. 331–33; E. Lord, A. McAdam, A. Felcher, M. Woods, B. Pulaski, E. Hutter, and J. Frelinger, Transfection of TGF-β Producing Tumors with IL-2 Elicits Tumor Rejection, in *Immunotherapy of Cancer With Vaccines*, at pp. 346–48; A. McAdam, B. Pulaski, S. Harkins, E. Hutter, J. Frelinger, and E. Lord, Coexpression of IL-2 and γ-IFN Enhances Tumor Immunity, in *Immunotherapy of Cancer With Vaccines*, at pp. 349–51. For general background on cytokine gene-transfected tumor cells see, for example, Z. Qin and T. Blankenstein, Influence of Local Cytokines on Tumor Metastasis: Using Cytokine Gene-Transfected Tumor Cells As Experimental Models, in Attempts to Understand Metastasis Formation III, Therapeutic Approaches for Metastasis Treatment, edited by U. Günthert, P. M. Schlag, and W. Birchmeier, pp. 55–64, Springer Verlag, Berlin 1996.

Despite the promising results with cytokine-gene-transfected cells in experimental animals, adaptation of these methods to patients faces several hurdles. As an initial matter, the technical difficulty and cost of generating sufficient quantities of gene-transfected tumor cells from a primary tumor specimen is significant. The tumor cells must be recovered from the tumor of which only a small specimen is usually available. The recovered tumor cells must be adapted to in vitro growth. This is a tedious and of ten unsuccessful procedure. The cells must be transfected in a procedure which has variable success with different tumor types and with cells of the same tumor type from different patients. See, V. W. Simons et al., Bioactivity of autologous irradiated renal cell carcinoma vaccines generated by in vivo GM-CSF gene transfer, *Cancer Research*, Vol. 57 (1997) 1537–1546; R. Soiffer et al., Vaccination with irradiated autologous melanoma cells engineered to secrete human granulocyte-macrophage colony-stimulatingfactor generates potent antitumor immunity in patients with metastatic melanoma, *Proceedings of the National Academy of Sciences*, Vol. 95 (1998) pp. 13141–13146. (The two immediately proceeding articles will hereinafter be collectively referred to as "Irradiated cancer cells and GM-CSF secretion. ") Unlike tumor cells obtained from animal tumor cell lines, which are homogeneous, tumor cells recovered from a human primary cancer lesion represent an extremely heterogeneous population of cells differing in their genotypes and phenotypes. Efficiency of transfection in such a cell population can be expected to be much less than in the quasi-monoclonal animal tumor cell populations. The transfected tumor cells with the highest cytokine production rate must be identified and selected. Thus, the overall procedure is time- and cost-intensive and the results can be unpredictable.

Another problem arises because the administration of viable gene-transfected tumor cells to patients is risky and ethically unacceptable. Administration of cytokine-gene-transfected somatic cells such as fibroblasts is also risky. In animal experiments, injected cytokine-gene transfected tumor cells have occasionally lost the cytokine gene and demonstrated aggressive tumor growth, and cytokine-gene transfected fibroblasts have been shown to accelerate tumor growth. Tsai, J., Gansbacher, B., Tait, L., Miller, S. R., Heppner, G. H., Induction of Antitumor Immunity by Interleukin-2 Cene-Transduced Mouse Mammary Tumor Cells Versus Transduced Mammary Stromal Fibroblasts; J. Natl. Cancer Inst. 85: 546–52 (1993). Transfection with a cytokine or a growth factor gene has also been shown to confer a malignant or metastasizing phenotype on some tumor cells. Malik, S. T. A., Naylor, M. S., East, N., Oliff, A., Balkwill, F. R., Cells Secreting Tumor Necrosis Factor Show Enhanced Metastasis In Nude Mice; Eur. J. Cancer 26: 1031–1034 (1990).

In patient trials, tumor cells must be subjected to lethal radiation before administration to prevent replication of the tumor cells. Although the irradiated cells retain the capability of secreting the encoded cytokine, production capacity is of ten diminished. Accumulated data from various gene transfection experiments indicates that the cytokine production rate for cytokine-gene transfected cells is in the range of picograms to nanograms per 24 h per $10^6$ cells. Colombo, M. P., Fomy, G., Cytokine Gene Transfer in Tumor Inhibition and Tumor Therapy. Where Are We Now?; Immunol. Today 15: 48–51(1994). With respect to irradiated transfected tumor cells, the combination of diminished capacity to produce the encoded cytokine and the elimination of viable, replicating cytokine-producing cells will severely limit the quantity of cytokines secreted. The contribution of replicating tumor cells to cytokine production was demonstrated by data from a study where mice were injected with IL-2-gene-transfected P815 mouse mastocytoma cells or with untransfected P815 tumor cells. Ley, V. Roth, C., Langlade-Demoyen, P. Larsson-Sciard, E. L., Kourilsky, P., A Novel Approach to the Induction of specific Cytolytic T Cells In Vivo; Res. Immunol. 141: 855–863 (1990). Within 2–3 weeks following injection of $10^6$ untransfected cells, a tumor having a volume of about 10,000 mm$^3$, corresponding to approximately $10^9$–$10^{10}$ tumor cells, was generated. In contrast, injection of $10^6$ transfected cells resulted in a much slower growing tumor of only 100 mm$^3$ volume within two weeks. This small tumor regressed within a few more weeks indicating that cytokine had been secreted not only by the initially injected 106 transfected cells but by the daughter cells as well.

Assuming a cytokine production rate of a few nanograms per $10^6$ cells per 24 hours, it will be appreciated that the dividing tumor cells will secrete steadily increasing quantities of cytokine during the growth phase of the tumor such that, after 14 days, a cytokine production rate of a few hundred to a few thousand nanograms per 24 hours would be achieved. It will further be appreciated that, if replication of the tumor cells is prevented by irradiation the release rate of transfected X-irradiated tumor cells cannot go up during the follow up. This is in contrast to vital gene-transfected cells where there is a great dynamic in cytokine release due to the fact that the cells first multiply and produce more and more cytokine and then die and the cytokine production diminishes. Even assuming that the cytokine production rate from the initially injected cells remains stable over 14 days, the quantity of cytokines will be lower by a factor of 100 to 1,000 compared to the quantity produced by viable replicating tumor cells. In patient trials, $10^7$ cells are typically employed in vaccines. Nevertheless, considering the large body mass of a human, it appears that the cytokine production rates obtainable from $10^7$ irradiated non-replicating transfected tumor cells will be very low. Furthermore, it has been shown that each patient's tumor cells show a different transfection rate and a different cytokine release rate. See, Irradiated cancer cells and GM-CSF secretion.

In sum, the use of cytokine gene-transfected cells permits the localized delivery of cytokines but it has several drawbacks which include: unpredictability of the number of gene copies introduced in the transfected cell and extent to which the gene copies are expressed; unpredictability of the amount of cytokine that will be secreted by the transfected cells; and finally possibility that the transfected tumor cells will lose the inserted gene, escape elimination and develop new tumors. In general, and despite the progress in gene therapy, the obtention of appropriately transfected cells is complicated, difficult, and expensive.

Notwithstanding the intense effort expended in research directed to the preparation of tumor vaccines capable of stimulating immune response to specific tumor antigens, none have been developed which are simple, reliable and relatively inexpensive. As a result, efforts to develop such vaccines continue unabated.

The fight against infectious diseases with vaccines also teaches that prevention of infectious diseases with vaccines is easier than therapy of the same diseases under development. This experience has been interpreted as suggesting that prophylactic vaccination against cancer may be more successful than vaccination when the disease is at an advanced stage. *Immunotherapy of Cancers With Vaccines*, at p. 4. However, therapeutic vaccination may be the only resort to fight against certain diseases and in particular against tumors.

In light of the problems or drawbacks associated with the systemic administration of cytokines or with the use of cytokine gene-transfected cells, it is desirable to provide a composition and method of administration for immunological treatment of tumors with a selected cytokine whose non-systemic administration leads to positive effects on the treatment of tumors. Such preparation has to be administered at a physiologically acceptable dosage by an appropriate administration route. It is also desirable to provide a composition and method of administration for immunological treatment of tumors with properties that include: (a) good tolerance with the receiving living being, a property that requires the absence of or at least minimization of undesirable side effects; (b) high effectivity upon administration in amounts of the order of $\mu$g rather than in the order of mg as in systemic treatments; (c) appropriate form for local administration; and (d) appropriate form for administration in a controlled and predictable manner.

SUMMARY AND OBJECTS OF THE INVENTION

An object of the present invention is the induction of immune responses to tumors. In particular, an object of the present invention is the design of a depot formulation including an immunostimulant such as a cytokine that is optimally suited as an adjuvant for the induction of cell-dependent cytotoxic immune responses to cellular antigens.

Another object of the present invention is to provide methods of preparing tumor vaccines capable of stimulating immune responses to tumor cells which are simple, reliable, and relatively inexpensive to use.

Another object of the present invention is to provide a composition comprising antigenic material and a depot with immunostimulating material that is tolerated by living organisms without unacceptably deleterious side effects. In particular, an object of the present invention is to provide a composition with antigenic tumor cells, preferably inactivated cells, and a depot with at least one cytokine that is tolerated by living organisms without unacceptably deleterious side effects.

Another object of the present invention is to provide tumor vaccines comprising tumor cells mixed with immunostimulant adsorbed to aluminum hydroxide in the same inoculum such that active specific immunity is induced.

Another object of the present invention is to provide an intratumoral treatment preparation including an immunostimulant adsorbed to a depot which can be injected into a tumor.

A feature of the compositions and methods of this invention is that the compositions can be administered as vaccines are typically administered, and also they can be administered in intratumoral applications. It is also a feature of the compositions of the present invention that the specific characterization of treatment is not critical to the beneficial results derived therefrom.

These and other objects and features of the present invention will become more fully apparent from the following description and appended claims, or may be learned by the practice of the invention as set forth hereinafter.

To achieve the foregoing objects, and in accordance with the invention as exemplified by embodiments described herein, compositions and methods are provided which can be utilized in active immunization as a prophylactic treatment or a therapeutic treatment for tumors. The compositions are employed as injectable tumor vaccines or as preparations for intratumoral administration and are capable of stimulating immune responses to specific tumor antigens.

The tumor vaccines induce an immune response to prevent tumor proliferation and growth and include an antigenic cellular material comprising a plurality of inactivated tumor cells or tumor cell portions, an adsorbent depot material, and at least one immunostimulant adsorbed to the depot material. The tumor cells or tumor cell portions are inactivated such that the antigenic structures thereof are preserved, with the tumor cells or tumor cell portions being capable of inducing an immune response. The depot material with absorbed immunostimulant is mixed with the tumor cells or tumor cell portions to form the vaccine compositions. The preparations for intratumoral administration include the depot material adsorbed immunostimulant without the antigenic cellular material. The immunostimulant adsorbed to the depot material permits release of biologically active quantities of the immunostimulant over a period of time rather than all at once.

A preferred immunostimulant for the compositions of the invention is a cytokine, such as a recombinant human cytokine, particularly a lymphokine, and more particularly interleukin-2. Other useful immunostimulants besides interleukin-2 include interleukin-4, interleukin-12, G-CSF, GM-CSF, and combinations thereof, as well as bacterial cell wall components such as muramyl dipeptide. Preferably, the immunostimulant is present in the compositions in an amount of at least about 10 $\mu$g.

A preferred depot material is an aluminum-based depot such as aluminum hydroxide, although other inorganic materials such as calcium phosphate as well as other inorganic or organic particles which are capable of adsorbing proteins such as latex particles and ion exchangers can also be used as depot material, along with various combinations thereof. In the context of this invention, the cytokine adsorbed to the depot material is, in combination, an adjuvant.

The ratio of immunostimulant to depot material in the compositions of the invention is chosen such that the depot material adsorbs all of the immunostimulant. Preferably, the ratio of immunostimulant to depot material is from about 0.1 to about 1 $\mu$g/$\mu$g.

A preferred treatment preparation for intratumoral injection to eliminate a tumor and induce an immune response to the tumor includes an inorganic depot material composed of aluminum hydroxide, and a cytokine immunostimulant adsorbed to the depot material.

In a method for inducing an immune response to prevent tumor proliferation and growth, one or more tumor vaccine inoculums according to the invention are provided, and an effective amount of one or more of the tumor vaccine inoculums are injected at least once so as to permit release of biologically active quantities of the immunostimulant over a period of time to induce an immune response to the presence of active tumor cells. The tumor cells which can be used in the vaccine inoculums may be obtained from various sources such as tumor cells recovered from a primary lesion or secondary lesions in a patient, tumor cells prepared by in vitro culture of the tumor cells recovered from a patient, tumor cells prepared by in vitro culture of allogeneic tumor cell lines, and combinations thereof. The tumor cell portions which can be used in the vaccine inoculums may be obtained from various processes such as lyzing of the tumor cells, preparing extracts of cell membranes and membrane vesicles, and combinations thereof.

The tumor vaccine inoculum can be injected to prevent proliferation and growth of various tumors such as melanoma, renal carcinoma, prostate carcinoma, colon carcinoma, pancreas carcinoma, and lung carcinoma, as well as B lymphoma. It should be understood that a particular vaccine composition will contain tumor cells that correspond to the particular tumor being treated. Thus, a vaccine composition for renal carcinoma will contain renal carcinoma cells or cellular portions thereof. The tumor vaccine inoculums can be injected into a patient subcutaneously and/or intradermally.

In a preferred method for intratumoral treatment, a treatment preparation is provided as described above, and an effective amount of the treatment preparation is injected at least once into a tumor so as to permit release of biologically active quantities of the cytokine immunostimulant over a period of time to induce an immune response.

Instead of relying on systemic administration of cytokines or on cytokine gene-transfected cells, the present invention encompasses the following strategy. In-situ cytokine-producing gene-transfected cells are characterized by having the source of cytokine and the source of immunogenic material combined in one entity. Instead of having this combination in a gene-transfected cell, the present invention uses mixtures of tumor cells and cytokines in depot formnulations. One of the advantages of this procedure is that it is relatively easy to prepare vaccines from irradiated tumor cells and one or several cytokines in depot formulations. The cytokine depots can be kept on the shelf and used as needed. It is possible and easy to vary the dose of both components, the tumor cells and the cytokine, thus being able to elucidate their contribution to the induction of the immune response and to make vaccines with optimal properties for each patient. Another advantage of this invention is that parameters that characterize the vaccine composition and its administration can be elaborated on a quantitative basis rather than by trial and error. These parameters include the composition of the vaccine, and more specifically the tumor cell dose and cytokine dose, and the vaccination conditions, including vaccination site and vaccination course.

BRIEF DESCRIPTION OF THE DRAWINGS

In order to more fully understand the manner in which the above-recited and other advantages and objects of the invention are obtained, a more particular description of the invention will be rendered by reference to specific embodiments thereof as illustrated in the appended drawings. Understanding that these drawings depict only typical embodiments of the invention and are not therefore to be considered to be limiting of its scope, the invention in its presently understood best mode for making and using the same will be described and explained with additional specificity and detail through the use of the accompanying drawings in which.

DETAILED DESCRIPTION OF THE INVENTION

Figure 1:
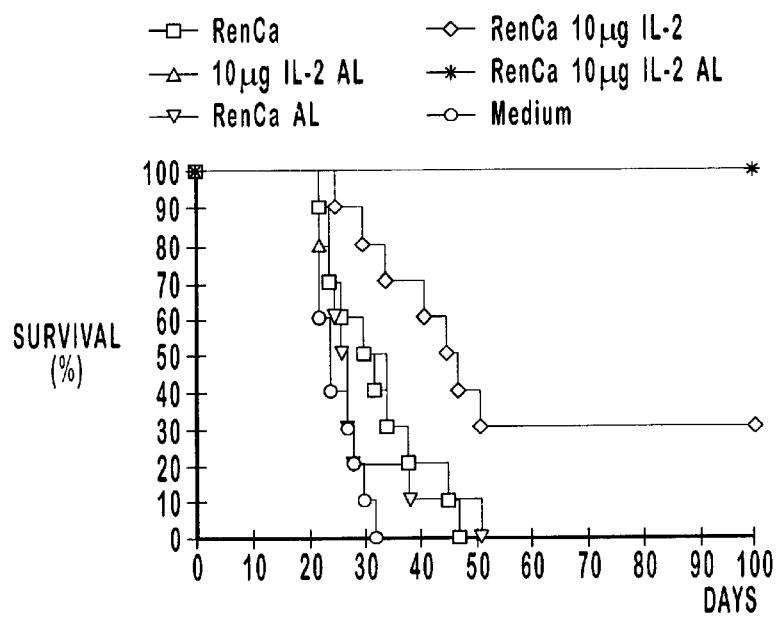
FIG. 1 is a survival plot for a RenCa therapeutic study with different vaccine compositions.

The present invention is directed to tumor vaccine compositions and methods for providing active immunization as prophylactic treatment and as therapeutic treatment, the latter treatment also referred to as immunotherapy. Active immunization as prophylactic treatment is directed to prevention of the proliferation of tumor cells such that a primary or secondary tumor does not form. Therapeutic treatment or immunotherapy is directed to the treatment of known or suspected proliferating tumor cells. The goal of therapeutic treatment is to arrest the proliferation of existing tumor cells and even to destroy them.

Cancer cells typically originate in a primary tumor. After resection of a primary tumor, the medical evidence supports that the occurrence of a secondary tumor is likely. In what is referred to as "minimal residual disease" as little as one cell or agglomerates of a few cells may be present upon resection of the primary tumor, thus laying the groundwork for a secondary tumor. These cells might be "dormant" for several years or even for a decade and start to divide for unknown reasons at an unpredictable time. Treatment at this stage is in essence a combination of prophylactic and therapeutic treatment.

The present invention provides tumor vaccines, and methods of preparing tumor vaccines, capable of stimulating immune responses to specific tumor antigens which can be injected into a host to thereby induce active specific immunity to the tumor antigens. Animal experiments using cytokine-gene-transfected tumor cells have demonstrated that efficient stimulation of the immune system against the injected tumor cells occurs when both the cytokine immunostimulus and the tumor antigenic stimulus are presented in a substantially side-by-side fashion on the tumor cell membrane. The tumor vaccines of the present invention include an antigenic cellular material including a plurality of inactivated tumor cells or tumor cell portions, which are combined with at least one substance having immune stimulating activity, i.e., an immunostimulant. The immunostimulants are combined with the tumor cells or tumor cell portions such that the immunostimulants are themselves either directly or indirectly attached to the tumor cells or tumor cell portions and/or mixed in the preparation so as to be in a side by side fashion with the tumor antigens. Alternatively, or additionally, the immunostimulants are prepared in depot forms or as aggregated or complexed forms which are either directly or indirectly attached to the tumor cells or tumor cell portions and/or mixed in the preparation so as to be side by side with the tumor antigens in the same inoculum. The immunostimulants are combined with the tumor cells or tumor cell portions in a manner that permits biologically active quantities of the immunostimulants to be released over a period of time following injection of the vaccine. In this manner, the natural immune system reaction is more closely mimicked and effective immunity is induced.

Coupling of immunostimulants or of immunostimulants incorporated in depot forms or aggregated or complexed forms to tumor cells or tumor cell portions provides the ability to concentrate considerable immune stimulating potency locally at the level of the tumor cells or tumor cell membranes in the vaccine inoculum. For example, it has been discovered that 30 μg of IL-2 per vaccine encapsulated in liposomes can be coupled to $10^6$ tumor cells. This quantity far exceeds the quantity of cytokine that can be released by genetically engineered tumor cells transfected with a cytokine gene. In addition, the localized concentration of cytokines within the vaccine inoculum avoids the severe side effects associated with systemic administration of cytokines. Simultaneous release of multiple immunostimulants is possible which, as noted above, more closely imitates the natural immune system response. The methods of the present invention can be utilized in combination with other known immunostimulating techniques such as the use of autologous Newcastle Disease Virus-modified tumor cells.

I. The Tumor Cells and Tumor Cell Portions

The inactivated tumor cells or tumor cell portions of the antigenic cellular material used in the vaccine compositions of the invention can be selected from various known tumor cells or portions thereof. These include B lymphoma cells, as well as melanoma cells, renal carcinoma cells, prostate carcinoma cells, colon carcinoma cells, pancreas carcinoma cells, lung carcinoma cells, combinations thereof, and the like. Preferably, the antigenic cellular material comprises about $10^5$ to about $10^8$ tumor cells or tumor cell portions.

Morphologically intact and vital tumor cells, inactivated by high doses (200 Gray) of X-radiation, have been shown capable of inducing an effective immune response in animal tumor models and in vitro while lyzed tumor cells were less effective. On the other hand, IL-2 containing liposomes which have been fused with membrane vesicles of tumor cells and mixtures of IL-2 and ultrasonic tumor cell homogenates encapsulated in liposomes have also been shown to be capable of inducing tumor specific immunity. Thus, although portions of tumor cells may be employed in the tumor vaccines in accord with the present invention, morphologically intact and vital tumor cells which have been inactivated by X-radiation are preferred.

II. The Immunostimulants

Various substances are known to have immune stimulating activity against tumor cells. Among these are the cytokines, bacterial superantigens, e.g., staphylococcal enterotoxin A, conjugates prepared from bacterial, murine, or human heat shock proteins, and bacterial cell wall components and related compounds, e.g., muramyl dipeptide (N-acetyl-muramyl-L-alanyl-D-isoglutamine, "MDP", a peptide that can be used in the induction of antibodies and cell-mediated immunity. A number of MDP derivatives have also been shown to have similar activity). In addition, co-stimulatory components of mammalian cell membranes, e.g., HLA-B7, MHC-I and MHC-II antigens, have been shown to enhance tumor-specilfic immune responses. Ostrand-Rosenberg, S., Tumor Immunotherapy: The Tumor Cell As An Antigen-Presenting Cell, Curr. Opin. Immunol. 6: 722–27 (1994); Wahl, W. L., Strome, S. E., Nabel, G. J., Plautz, G. E., Cameron, M. J., San, H., Fox, B. A., Shu, S., Chang, A. E., Generation of Therapeutic T-Lymphocytes After In Vivo Tumor Transfection With An Allogeneic Class I Major Histocompatibility Complex Gene, J. Immunotherapy 17: 1–11 (1995).

As described below, the present invention teaches that immunostimulants may themselves be attached directly, such as by covalent binding, or indirectly, such as through protein carriers, to the tumor cells or tumor cell portions. In this manner, the tumor cells with attached immunostimulants will behave much like tumor cells transfected with genes encoding for the immunostimulant because the immunostimulants are essentially exposed on the surfaces of tumor cell membranes in close molecular proximity to the antigenic membrane structures of the tumor cells. Immunostimulants can alternatively be incorporated into various depot forms or complexed with other substances in various aggregate forms. The depot forms or aggregate forms may then be attached, either directly or indirectly, to the tumor cells or tumor cell portions.

Because the depot forms or aggregate forms can incorporate relatively large quantities of immunostimulants, this method will dispose a higher quantity of immunostimulants mixed with the tumor antigens. For example, it has been discovered, in accord with the present invention, that liposomes containing 30 $\mu$g of IL-2 can be covalently coupled to $10^6$ B16 tumor cells. Depot particles such as liposomes or microspheres are known. Cytokines encapsulated into liposomes have been shown to be released in active form. It also appears that a portion of the encapsulated cytokine becomes integrated into the liposome membranes because the liposomes will bind to cytokine receptors on other cells. Kedar, E., Rutkowski, Y., Braun, E., Emanuel, N., Barenholz, Y., Delivery of Cytokines by Liposomes. I. Preparation and Characterization of Interleukin-2 Encapsulated in Long-Circulating Sterically Stabilized Liposomes; J. Immunother. 16: 47–59 (1994). It is also possible to encapsulate two different cytokines, IL-2 and GM-CSF, into a single liposome preparation. Anderson, O. P. M., Hanson, D. C., Hasz, D. E., Halet, M. R., Blazar, B. R., Ochoa, A. C., Cytokines in Liposomes: Preliminary Studies With IL-1, IL-2, IL-6, GM-CSF and Interferon-γ; Cytokine 6; 92–101 (1994).

It has been shown that biodegradable polymers, e.g, polylactides made by copolymerization from lactic acid and glycolic acid, can be "loaded" with cytokines, hormones, or other immunostimulants. The loaded substances become enclosed in hollow spaces within the biopolymers or are adsorbed or chemically bonded to surface structures. It has been shown that polylactide-adsorbed hormones are released slowly and in biologically active form. Gombotz, W. R., Pettit, D.K., Biodegradable Polymers for Protein and Peptide Drug Delivery, Review, Bioconjugate Chem. 6: 332–351 (1995). Branched-chain polymers, equipped with a multitude of "arms" are useful carriers for immunostimulants. Examples of such carriers include "PEG star" molecules formed through polymerization of ethylene oxide with a core of cross-linked divinylbenzene. These molecules have a molecular mass in the range of 600 kD and contain more than 100 PEG "arms" extending from the core. Other examples are poly-L-lysine, available in different molecular masses and in a succinylated form, and branched polypeptides built on poly-L-lysine.

Inorganic particles and gels such as aluminum hydroxide (AL) are known for their capacity for adsorbing proteins and have been used in vaccines, e.g., tetanus vaccine prepared with aluminum hydroxide gel (Alhydrogel). Particles or gels made of calcium phosphate also have an adsorptive capacity for biomolecules and have been utilized in bacterial vaccines and as DNA carriers for transfection experiments. It is possible to adsorb or otherwise chemically bind immunostimulants to such particles or gels and in general to combine immunostimulants to adjuvants.

It will be appreciated that the depot and aggregate forms described could be utilized to carry multiple molecules of a single immunostimulant or to carry multiple molecules of different immunostimulants. The simultaneous release of multiple immunostimulants would more closely mimic the natural immune response.

The cytokine preferably used in the context of this invention is IL-2. Recombinant human IL-2 is commercially available. Recombinant human IL-2 with a specific activity of 18·$10^6$ IU/ml was either purchased or provided by Chiron, Inc., for the experiments described hereinbelow. In addition to its availability, it is known that IL-2 reacts biologically in human beings as good as in mice, a property that is referred to as "biological cross-reaction."

III. Combining Immunostimulants and Tumor Cells or Tumor Cell Portions

Chemotaxis is a reaction by which the direction of locomotion and the orientation of cells is determined by chemical substances. The cells become oriented and move towards (positive chemotaxis) or away from (negative chemotaxis) the source of a concentration gradient of the substance. For example, leucocytes show positive chemotaxis towards many agents including a plurality of cytokines. Chemotaxis is essential for recruitment of cells to sites of tissue injury and inflammation. See, for example, *Dictionary of*

*Immunology*, at p. 40. A chemotactic gradient is a gradient that causes chemotaxis.

The results of experiments in animal tumor models with cytokine gene transfected tumor cells demonstrate that the cytokines released from the tumor cells form a chemotactic gradient extending into the tissue surrounding the tumor vaccine inoculum. Immune cells, attracted by the cytokine, migrate into the vaccine inoculum and encounter the tumor cells. Depending on the type of cytokine, the attracted immune cells either attack the tumor cells directly or release additional cytokines which attract other tumor-attacking lymphocytes. Because the most likely location of the proposed cellular interactions is the membrane of the tumor cell which is releasing the cytokine, the lymphocytes come into direct physical contact with the tumor cell antigens also present on the membrane. Some experiments have indicated that exposure of the cytokine directly on the membranes of the tumor cells rather than in the adjacent cellular environment is important in inducing immunity. Other experiments, however, have shown that the immune response induced by cytokines released from cytokine-gene transfected tumor cells can be conferred to untransfected tumor cells of the same or another type provided the untransfected tumor cells are closely mixed with the transfected tumor cells. For purposes of the present invention, it is preferred that the immunostimulants adsorbed to aluminum hydroxide depot be closely mixed with the tumor cells or tumor cell portions. Most preferably, the immunostimulants may be both attached to, and mixed in aluminum hydroxide adsorbed form, with the tumor cells or tumor cell portions.

It is believed to be advantageous to mix the immunostimulants, particularly when prepared in AL depot forms, with the tumor cell or tumor cells portions to ensure direct contact of immune system cells with the tumor cell antigens. Mixing of the immunostimulants, particularly when prepared in depot forms or aggregate forms, with the tumor cells such that a chemotactic gradient will be formed locally within the vaccine inoculum, however, may also be effective.

IV. Combination With Other Known Immunostimulation Techniques

Tumor vaccine preparations in accord with the present invention may be combined with other known immunostimulation techniques. In particular, tumor vaccines prepared from tumor cells which have been xenogenized by infection with viruses such as Newcastle Disease Virus (NDV) could be applied mixed with the AL-adsorbed immunostimulants.

Tumor vaccine preparations and methods for preparing tumor vaccine preparations in accord with the present invention are described in the following examples as well as in an article by the inventors, F. W. Falkenberg and M. Reimer, Liposome-Encapsulated Cytokines Covalently Coupled to Tumor Cells: An Alternative To Gene-Transfected Tumor Cells as Vaccines?, Vaccine Research, Vol. (1995) pp. 1–7, which article is hereby incorporated by reference.

V. The Depot Formulation

Aluminum hydroxide has an inherent adjuvant property and consistently with this property it has been used in bacterial and viral vaccines. Such vaccines are used to induce humoral immunity, which is antibody-mediated immunity. Aluminum hydroxide is known in particular for its ability to enhance this type of immune response. However, humoral immune responses have been proven counterproductive in tumor therapy. It is believed that this effect is due to antibodies to tumor antigens masking the tumor antigens themselves, thus protecting the tumor from the aggression by cytotoxic T-lymphocytes and other immune system cells. Consistently with this experience, some research has backed away from the use of aluminum hydroxide in experimental tumor vaccination. It has also been shown that aluminum hydroxide does not act as an adjuvant when it is injected together with inactivated tumor cells, and that animals treated with such vaccines die as fast or even faster than animals that were treated with inactivated tumor cells alone. Furthermore, experiments carried out in the context of this invention have shown that the administration of aluminum hydroxide alone to control groups provided no protection.

It is also known that aluminum hydroxide is an adjuvant only for soluble protein or for carbohydrate antigens, but not for antigenic material in the form of inactivated cells. However, it has been found in the present invention that aluminum hydroxide is optimally suited as a depot for cytokines. Accordingly, cytokines adsorbed to aluminum hydroxide are optimally suited as adjuvants for cell-dependent cytotoxic immune responses to cellular antigens.

Depot formulations were also prepared with liposomes that were in turn prepared from 1,2-Dimyristoyl-sn-Glycero-3-Phospho-Choline powder (DMPC, Avanti Polar Lipids, Alabaster, Alabama) as described by P. M. Anderson, E. Katsanis, S. F. Sencer, D. Hasz, A. C. Ochoa, and B. Bostrom, Depot characteristics and biodistribution of Interleukin-2 liposomes. Importance of route of administration, Journal of Immunotherapy Vol. 12 (1991) pages 19–31, the disclosure of which is incorporated herein by reference. A range of 90–96% of the added IL-2 was encapsulated in the liposomes. Free IL-2 was determined in the supernatant solution by an IL-2 bioassay using CTLL-2 cells. Although aluminum hydroxide depots are preferred in the present invention, IL-2 can also be adsorbed to an organic adsorbent material such as latex beads, and the embodiments of the present invention also include cytokines adsorbed to latex beads. Combinations of aluminum hydroxide adsorbed and liposome-encapsulated cytokines are other embodiments of the present invention.

VI. Examples of Therapeutic and Prophylactic Applications of the Present Invention.

The vaccine compositions of the present invention comprise inactivated tumor cells or tumor cell portions, mixed with depots that contain at least one immunostimulant. A preferred composition in accordance with the present invention comprises in particular irradiated tumor cells, and IL-2 adsorbed to an AL depot. Tumor cells that have been inactivated by exposure to radiation provide the antigenic material, while aluminum hydroxide is a preferred depot forming material, and the cytokine IL-2 is an immunostimulating agent which is adsorbed to the depot-forming material. Each of these elements will be described in more detail hereinbelow.

A preferred treatment preparation for intratumoral injection to eliminate a tumor and induce an immune response to the tumor includes an inorganic depot material composed of aluminum hydroxide, and a cytokine immunostimulant adsorbed to the depot material.

It has been discovered in accordance with the present invention that the amount of IL-2 contained in the locally administered composition is critical. A threshold dose of IL-2 is necessary to induce a minimal prophylactic or therapeutic immune response, while an excessive dose thwarts the desired immune response.

In preferred compositions, the IL-2 is adsorbed to an inorganic material, such as aluminum hydroxide, which serves as a depot material. The ratio of IL-2 to aluminum hydroxide in such compositions is preferably from about 0.1 to about 1 μg/μg. Such compositions preferably comprise at least about 10 μg of IL-2 per vaccine inoculum, while the aluminum hydroxide is present in an amount of at least about 10 μg per vaccine inoculum, and preferably from about 10 μg to about 100 μg. Alternatively, calcium phosphate can serve as the depot material.

Preferably, irradiated tumor cells are administered with the IL-2 adsorbed aluminum hydroxide depot. Irradiation of the cells inactivates the disease causing aspect but retains the antigenicity and morphology of the cells. Thus, the cells are capable of promoting an immune response, while not causing disease. Preferably, the cells are irradiated with one or more high doses of X-radiation of about 100–200 Gray (Gy). More specifically, inactivation of tumor cells can be achieved by irradiating cells with 200 Gy under a $^{137}Cs$ irradiation source.

As an alternative to inactivated total tumor cells, unfractionated tumor cell lysates, cell membranes or cell portions that have been inactivated through exposure to X-rays can also be used, and this is the preferred procedure in the present invention It will be appreciated from the description of the invention herein, that the preferred irradiated cells comprise the tumor cells of the type desired to be treated. These cells can be obtained via a variety of sources. In particular, a person's own primary tumor can be used to obtain these cells. In case of low cell harvest from the primary tumor, the cells obtained from the primary tumor can be expanded in vitro to obtain the cell membranes needed for vaccination. Cells harvested from in vitro culture of tumor cells of allogeneic tumor cell lines can also be employed as antigen.

The tumor cell models RenCa and B16 were utilized for evaluation purposes as will be described further in the examples hereinbelow. These tumor models were utilized because human tumors fall approximately in between with respect to their immunogenic (immunity inducing) and tumorigenic (tumor inducing) characteristics.

RenCa murine renal cell carcinoma grown in BALB/c mice has slight inherent immunogenicity. Without treatment, mice inoculated with a dose of 100,000 live RenCa tumor cells will typically die within 3–4 weeks after inoculation. Specimens of this cell line were obtained from the Department of Oncology, Hoffmann-La Roche, Inc., Nutley, N.J.

The B16BL6/D5 highly metastatic subline (in this specification, this subline will be referred to concisely as "B 16") of the B16 murine melanoma grown in C57BL/6 mice has an extremely high tumorigenicity and very low immunogenicity. This is the most aggressive of the B16 tumor family. As few as 100 tumor cells will kill 100% of the mice within 5–7 weeks, and a dose of 100,000 kills 100% of mice within 3–4 weeks. Specimens of this subline were obtained from the Cleveland Clinic Foundation, Cleveland, Ohio.

Other murine mammary carcinoma model tumors used in experiments performed in the context of this invention comprise the C26 (BALB/c) and CT26 (BALB/c) murine colon carcinomas, the TS/A (BALB/c) murine mamma carcinoma, the murine lymphoma 38C13 (C3H/He), and the MCA (C57 BL/6) murine sarcoma. Nevertheless, RenCa and B16BL6/D5 mark the limits that comprise the levels of immunogenicity and tumorigenicity of these additional tumor models.

The adherently growing tumor cells were cultured in standard Rockwell Park Memorial Institute medium RPMI 1640 according to standard culture procedures and were harvested using a trypsin/versene solution. Tissue culture media and supplements are widely available and they were obtained in particular from Bio Whittaker, Walkersville, Md.

In the prophylactic experiments performed in the context of this invention, the animals were first vaccinated and then the induced immunity was checked by following with a lethal dose of live tumor cells. This is a practice that may clearly not be directly applied to human beings. However, such prophylactic vaccination experiments performed on animals provide insight on and indications of the compositions that may successfully work on an individual which is suffering from a tumor disease. This is particularly applicable to results of experiments performed with IL-2, which is characterized by biological cross-reaction with respect to human beings and mice. By using the vaccination preparation technique of this invention that permits the precise control of the administered preparation composition, it was found that vaccination efficiency depends on several factors, including:

(a) The dose of antigenic material, and in particular the dose of inactivated tumor cells, in the vaccine. Specifically, the higher tumor cell doses gave better responses. About 10,000 inactivated cells per composition dose are needed at least. A preferred dose is in the range of about 100,000 to 10,000,000 inactivated cells per composition dose.

(b) The cytokine dose. A minimal dose, or threshold dose, of IL-2 is necessary to induce potent immunity, but the response became less positive at doses above a certain dose and all the animals that had been vaccinated with these doses died after being challenged with live tumor cells, although survival was also significantly prolonged. Therefore, there is a rather narrow cytokine-dose window. The results disclosed in this specification show the existence of a tolerable dose that produces positive immunological effects, the precise determination of such dose in the context of the experiments performed in this invention, and the methodology to successfully determine such dose window in other experiments.

(c) Vaccination frequency. It is known in general that most vaccines have to be adiministered several times to get a good immune response. It is specifically shown in this invention, however, that the stronger the tumorigenicity or the lower the immunogenicity of the tumor, the more vaccinations must be administered to achieve positive immune responses. For example, in the case of a tumor with relatively high immunogenicity such as the RenCa murine renal carcinoma, a single vaccination was sufficient to induce long lasting protective immunity in 80 to 100% of the vaccinated mice. In contrast, in the case of a tumor with practically no immunogenicity but relatively high tumorigenicity such as the B16BL6/D5 murine melanoma, 4 to 6 vaccinations were needed to induce lasting protective immunity in 50 to 60% of the vaccinated mice.

In sum, in the prophylactic vaccination, the animals were first vaccinated and then challenged with a lethal dose of live tumor cells. The animals became immune to a later challenge in one tumor model for a life time, and in another model, survival was increased substantially.

In the therapeutic experiments performed in the context of this invention, two classes of experiments were performed. In the first class of experiments, tumor-bearing mice were vaccinated. These mice had been injected with a dose of live tumor cells 4 days prior to the administration of the vaccinations. During the four-day interval from tumor induction to first vaccination, the tumor cells may have increased by tenfold with respect to the initially injected number of live cells and disseminated to other parts of the body.

Tumor induction can be performed at any location. For most of the vaccinations, tumor inductions were done subcutaneously. Tumor induction by intraperitoneal injection was also performed because it is the most effective way to induce a tumor, and mice get tumors faster than they do after subcutaneous induction. Because tumors develop so fast after intraperitoneal injection, the compositions and methods of this invention that cure mice with such intraperitoneally induced tumors provide very effective treatment.

Vaccination is much more effective by intraperitoneal injection than by subcutaneous injection, and intramuscular injection is less effective than subcutaneous injection. However, intraperitoneal vaccination can generally not be performed in patients because it is painful and very dangerous. Therefore, most of the vaccinations were administered subcutaneously so that the administration conditions in animal experiments could be as similar as possible to those in future human trials.

In the second class of therapeutic experiments, intratumoral therapy was performed. The preparations were administered into comparatively large tumors in mice that had been previously injected subcutaneously with live tumor cells to locally induce tumor growth. When the tumors were palpable, usually after one or two weeks, the tumor masses were about 0.1 to 0.5 ml each, corresponding to approximately $10^7$ to $10^8$ tumor cells. In both prophylactic and therapeutic vaccination experiments, the number of vaccinations has to be adapted depending on the inherent immunogenicity of the tumors investigated. Thus, in the case of a tumor with some inherent immunogenicity like the RenCa, a single vaccination might be sufficient either to confer protection in prophylactic vaccination experiments or to cure the tumor bearing animals by therapeutic vaccination experiments. If the immunogenicity of the tumor is very low as in the B16 melanoma or if the tumor is non-immunogenic, many vaccinations are needed in order to induce protection by prophylactic vaccination. Several therapeutic vaccinations are required to cure animals from such tumors. But even then, a success can of ten only be achieved when the tumor induction dose is reduced by one or several orders of magnitude.

In the first class of therapeutic experiments, mice were injected with about 100,000 live cells of the more immunogenic RenCa tumor. Four days later, the same mice were vaccinated with a preparation that contained about 1,000,000 inactivated RenCa cells and about 10 μg IL-2 adsorbed to aluminum hydroxide and the tumor in the vaccinated mice disappeared for good. These experiments also showed that vaccination efficiency depends on the number of irradiated tumor cells and on the amount of IL-2 adsorbed to aluminum hydroxide in the vaccine. In addition, the same threshold dose and dose window as in the prophylactic experiments were found. When the same type of therapeutic experiments were performed with the low immunogenic but highly tumorigenic B16BL6/D5 tumor cells, another factor turned out to be very important for the success of the therapeutic treatment. This factor is the tumor load present in the animal at the time the vaccination course began. To get a minimal positive response, the number of live tumor cells used for the induction of the tumor had to be reduced to 100 cells per animal. Only then about half of the mice were cured, and this was achieved upon administration of ten vaccinations.

In the second class of therapeutic experiments, the tumor growth could be slowed down considerably in the B16BL6/D5 model. The mice treated with a preparation that contained only aluminum hydroxide adsorbed IL-2 every days for several weeks lived significantly longer than the mice that received only saline solution, but all the mice eventually succumbed to the tumor. Life prolongation was much more pronounced with the RenCa model tumor, and about 50% of the mice were cured with as many as ten injections of aluminum hydroxide adsorbed IL-2 administered at a rate of one injection every three days.

In sum, in the therapeutic treatments the animals were first given a "lethal" dose of live tumor cells and several days later, a therapeutic administration was begun. In one tumor model, the animals were saved from an otherwise deadly tumor disease originating from 100,000 live tumor cells injected four days prior to injection of one dose of the therapeutic composition of the present invention.

In the treatment of tumor bearing animals by injecting IL-2 in a depot formulation into the existing tumor, approximately 60% of the animals carrying visible and palpable tumors were cured by the injection of a preparation that included aluminum hydroxide-adsorbed IL-2 into the tumor lesions. A third type of experiments involved rechallenges. In these experiments, mice that had been prophylactically vaccinated and had survived a challenge with vital tumor cells or mice that had been cured of a previously induced tumor by therapeutic vaccination were rechallenged by an inoculation with a lethal dose of vital tumor cells at least 100 days after the first challenge.

The following examples are meant to illustrate features of the present invention, but should not be construed as limiting the scope thereof. Although the following examples are grouped under various headings, these examples should be viewed in their entirety for all the information that they disclose explicitly or impliedly to anyone of ordinary skill in the art. The information that these examples and equivalents thereof disclose should not be limited to the specific characterizations of the individual headings, which are provided as an informative guide and as a presentation aid. Consequently, any of the following examples and equivalents thereof is offered for its full enabling, descriptive, supportive, and demonstrative content in addition to the limited content characterization that might be implied by any of the following concise headings when viewed in isolation.

The examples given below refer to graphs and tables. The graphs are Kaplan-Meier plots, also known as survival plots. These plots are a type of survival plot commonly used in the art. The ordinate in each plot represents survival expressed as a percentage. Survival in the following examples refers to the number of sample individuals alive in a specific vaccination group at a certain time. The abscissa in each plot represents the time in days from the day when a determined action was induced in the sample population under study. For example, in a typical therapeutic study, a number of mice are vaccinated at day 0. Time that precedes the vaccination day is given in negative day units. Tumor induction at day −4, for example, means that the individuals under study were administered a dose of a tumor inducing agent four days prior to the vaccination day. In a typical prophylactic experiment, day 0 is the day when the individuals under study are challenged by exposure to an agent against which one or a plurality of vaccines had been previously administered. The days when these vaccines were administered are given negative time values. For example, vaccination at day −35 in a prophylactic study means that the sample individuals were vaccinated thirty-five days prior to the day when they were exposed to a challenge.

In any experiment in the context of this invention, the Kaplan-Meier plot gives the percentage of surviving individuals at times (in days) after day 0. Kaplan-Meier plots are hereinafter referred to as "survival plots". Non-alphanumeric symbols such as circles, squares, triangles and asterisks represent actual surviving population readings at different days. In each plot, each one of these symbols is associated with a different vaccination group, and the solid lines link like-characters to more clearly show the time evolution of the vaccination group populations.

Each vaccination group is in turn characterized by a dose of a vaccine agent administered to the individuals in that group, the agent including at least one of the following components: An administration medium (hereinafter "medium") such as RPMI 1640 that is part of the common practice in the art; antigenic tumor cells, such as inactivated cancer cells; immunostimulant, such as cytokine, and depot, such as an aluminum-based substance. For example, "$10^6$ RenCa 10 μg IL-2 AL" characterizes a vaccination group whose individuals have been vaccinated with a preparation that includes about $10^6$ inactivated RenCa cells, IL-2 at a dose of about 10 μg adsorbed to 10 μg of aluminum hydroxide depot in an administration medium. The same notation is also used for referring to the vaccination composition itself that includes the same components. Similarly, "$10^6$ RenCa 10 μg IL-2" characterizes a vaccination group whose individuals have been vaccinated with a preparation that includes about $10^6$ inactivated RenCa cells to which IL-2 at a dose of about 10 μg in an administration medium was added (incubated before injection for about 30 min.), but no aluminum hydroxide depot, and "$10^6$ RenCa" characterizes a vaccination group whose individuals receive a vaccination that includes about $10^6$ inactivated RenCa cells only, but no aluminum hydroxide or IL-2. "RenCa AL" characterizes a vaccination group whose individuals receive a vaccination that includes inactivated RenCa cells and aluminum hydroxide in an administration medium, and "10 μg IL-2 AL" characterizes a vaccination group whose individuals receive a vaccination that includes a 10 μg dose of IL-2 adsorbed to 10 μg of aluminum hydroxide depot in an administration medium. The same notations are also used for referring to the respective vaccination compositions themselves.

The individuals in each vaccination group were inbred mice of the strains BALB/c and C57BL/6. On vaccination, aliquots of 100 μl of the vaccines were injected to anesthetized mice. For induction and challenge, a lethal dose of vital tumor cells was injected. Mice were daily inspected, and tumor development and survival were monitored. To prevent unnecessary suffering, mice bearing tumors of more than approximately 2 cm$^3$ were killed.

In the tables shown in the following examples, "n" stands for the number of individuals in each vaccination group. The forms of administration of the different agents to the individuals in each vaccination group are described by abbreviated terms that are standard in the art. These abbreviations include "iv" for intravenous, intravenously, intravenous injection, or intravenous administration, "i.p." for intraperitoneal, intraperitoneally, intraperitoneal injection or intraperitoneal administration, and "s.c." for subcutaneous, subcutaneously, subcutaneous injection or subcutaneous administration. "AL" stands for an aluminum hydroxide-based depot, "CP" stands for a calcium phosphate-based depot, and "Lip" stands for a liposome-based depot. The terms "$10^m$ B16" and "$10^m$ RenCa", where the exponent "m" is an integer, in the examples given below mean about $10^m$ inactivated B16 cells and about $10^m$ inactivated RenCa cells, respectively.

Data disclosed in the following examples have been analyzed according to statistical techniques that are standard in the art. In particular, significance is determined by using the Logrank test. For a textbook on the bases of the statistical analysis performed in the context of this invention, see, for example, Andrew Edmondson and David Druce, *Advanced Biology Statistics*, Oxford University Press, Oxford, UK 1996. General discussion, analytical mathematics, algorithmics, and actual working programs related to statistical description of data can be found in, for example, William H. Press, Saul A. Teukolsky, William T. Vetterling, and Brian P. Flannery, *Numerical Recipes*, pp. 603–49, Cambridge University Press, Cambridge, UK 1992. For a specific presentation of the bases of the Logrank test and related statistical principles, see, for example, Chap T. Le, *Fundamentals of Biostatistical Inference*, Marcel Dekker, Inc., New York 1992, particularly chapter 3, and more specifically pp. 152–55 therein.

As conventionally used in the art, significances are given below according to the following generic notation: "Identifying characteristic of the experimental hypothesis vs. Identifying characteristic of the null hypothesis; p". The experimental hypothesis is also known as the alternative hypothesis, the real number "p" is the level of significance, or concisely "significance," and the identifying characteristics can be listed in any order, with that for the experimental hypothesis preceding or following that for the null hypothesis. The number p satisfies p<1, although it can also be given as a percentage, and the smaller p is, the more likely it is that the null hypothesis will be rejected and the experimental hypothesis will be accepted. In other words, the experimental hypothesis is accepted as increasingly more convincing as p takes increasingly smaller values. A commonly used significance level in biology is 0.05, or 5%, but any value can in principle be chosen. See, for example, Advanced Biology Statistics at pp. 60–63. With this choice, it can be said that the samples being compared lead us to reject the null hypothesis and accept the experimental hypothesis at the 5% significance level. In common parlance, the term "explanation" is often used instead of the term "hypothesis". The following criteria are adopted regarding the statistical analysis of the results reported hereinbelow. Generally, the results supporting an experimental hypothesis or explanation are comparatively regarded as statistically not significant, significant, very significant or extremely significant depending on whether p respectively satisfies: p>0.05, 0.01<p<0.05, 0.001<p<0.01, or p<<0.001, where the bounds for the p-values are meant to be approximate.

More concretely in the context of this invention, an example of a significance expressed as "$10^6$ RenCa 10 μg IL-2 AL vs. 10 μg IL-2 AL; 0.0007" would be read as follows. At the 0.07% significance level, the survival of the individuals in the vaccination group characterized by "$10^6$ RenCa 10 μg IL-2 AL" compared with the survival of the individuals in the vaccination group characterized by "10 μg IL-2 AL" leads to the rejection of the hypothesis that the survival is due to the administration of 10 μg IL-2 adsorbed to 10 μg of an aluminum hydroxide-based depot and to the acceptance of the hypothesis that the survival is due to the administration of $10^6$ RenCa in addition to the administration of 10 μg IL-2 adsorbed to 10 μg of an aluminum hydroxide-based depot. We could also report the same result by using the following language: At the 0.07% significance level, the survival of the individuals in the vaccination group characterized by "$10^6$ RenCa 10 μg IL-2 AL" compared with the survival of the individuals in the vaccination group characterized by "10 μg IL-2 AL" leads to the rejection of the explanation that the survival is due to the administration of 10 μg IL-2 adsorbed to 10 μg of an aluminum hydroxide-based depot and to the acceptance of the explanation that the survival is due to the administration of $10^6$ RenCa in addition to the administration of 10 μg IL-2 adsorbed to 10 μg of an aluminum hydroxide-based depot. In other words, these results indicate that without the tumor cells as antigen in the vaccine, no cure is possible.

In contrast, an example of a significance expressed as "$10^2$ RenCa 10 μg IL-2 AL vs. 10 μg IL-2 AL; 0.9549" may not be read as follows: The survival of the individuals in the vaccination group characterized by "$10^2$ RenCa 10 μg IL-2 AL" compared with the survival of the individuals in the vaccination group characterized by "10 μg IL-2 AL" leads to the rejection of the hypothesis that the survival is due to the administration of 10 μg IL-2 adsorbed to 10 μg of an aluminum hydroxide-based depot and to the acceptance of the hypothesis that the survival is due to the administration of $10^2$ RenCa in addition to the administration of 10 μg IL-2 adsorbed to 10 μg of an aluminum hydroxide-based depot. In this example, the rejection of the null hypothesis is not convincing because p is very close to unity, or to 100% if expressed as a percentage. In other words, the cause for survival of the individuals in the vaccination group characterized by $10^2$ RenCa 10 μg IL-2 AL is statistically indistinguishable from the cause for survival of the individuals in the vaccination group characterized by 10 μg IL-2 AL.

Although the foregoing discussion of statistical levels of significance predominantly refers to "survival," this is meant to be illustrative and the effectiveness of a treatment is not to be assessed in terms of survival rates only. To this respect, significant life prolongation is an important effect, although actual survival is clearly more desirable. If animals that have been treated according to this invention survive significantly longer but finally succumb to the tumor, a successful treatment has been achieved.

"Control group" hereinbelow stands for a group of mice that were injected with only the medium that was used in the preparations delivered to the mice in the other groups in each one of the following examples. Accordingly, mice in the control group in therapeutic studies had a tumor induced like the mice in the other groups had, but they were not vaccinated. Instead, they were injected with the medium that was used to deliver the preparation to the mice that were vaccinated.

Referring to the Examples discussed hereinbelow, the numbers of irradiated tumor cells are the approximate numbers of cells that are contained in the vaccines, and each vaccine generally has a volume of about 100 μl per mouse per inoculation. Generally, the amount of cytokine and the amount of AL to which the cytokine is adsorbed are approximately equal to each other, and in particular about 10 μg of IL-2 is adsorbed to about 10 μg of AL. The adsorptive capacity of calcium phosphate, however, is much lower than that of AL and consequently the amount of CP used is about 100 times as great. In particular, about 10 μg of IL-2 is adsorbed to about 1000 μg of CP.

Compositions with cytokine, adsorbent and cells are generally prepared by mixing the cytokine and the adsorbent, incubating for about 30 minutes at room temperature, and then adding the cells. The volumes are adjusted so that a vaccine volume of about 100 μl results. This volume might be bigger if more cells or more IL-2 and more adsorbent are used. In the case of adsorption of IL-2 to the tumor cells, the amount of IL-2 is added to the tumor cells, mixed, and the mixture incubated at room temperature for about 30 minutes. Culture medium without serum is used for preparing the cell suspensions and saline or buffered solutions can be used for preparing the other substances.

The preparation techniques for different preparations used in this invention are more specifically described hereinbelow. These techniques refer to the preparation of cytokine depot tumor vaccines, the preparation of vaccines containing IL-2 but no depot material, and the preparation of vaccines containing calcium phosphate as depot material. In addition, the properties of other substances that can in principle be used as depot material for adsorbing IL-2 are also discussed.

Aluminum hydroxide gel was used to prepare cytokine depot tumor vaccines. In particular, the aluminum hydroxide gel was a high protein binding variety of aluminum hydroxide—Rehydragel HPA—produced by Reheis, Inc., Berkely Heights, N.J. This gel contains 20 mg of aluminum hydroxide per ml. It has a very high binding capacity of about 2.5 mg BSA per mg of aluminum hydroxide, and the binding capacity for IL-2 was determined in the context of this invention to be about 1 mg IL-2 per mg of aluminum hydroxide.

IL-2 was used as provided commercially by Chiron Corp., in the form of, for example, 1 mg IL-2 as lyophilized powder in an injection ampulla. The lyophilized material is dissolved by injection of 1.0 ml of sterile distilled water into the injection ampulla resulting in a IL-2 concentration of 1000 μg/ml (or 1.2 μg of lyophilized material dissolved in 1.2 ml of water).

To prepare the vaccine for an exemplary number of 9 animals, the following amounts are used. Five 105 μl of aluminum hydroxide gel are added to and thoroughly mixed with 100 μl of the sterile IL-2 solution containing 100 μof IL-2, thus obtaining IL-2 adsorbed to aluminum hydroxide depot material or, concisely, IL-2 adsorbed to aluminum hydroxide.

About 900 μl (or more precisely 895 μl) of a cell suspension containing the appropriate number of irradiated tumor cells—for example, $10^7$ irradiated tumor cells—are subsequently mixed with the 105 μl of the IL-2 adsorbed to aluminum hydroxide preparation. 100 μl of this mixture containing irradiated tumor cells and IL-2 adsorbed to aluminum hydroxide are injected into each animal.

The preparations for intratumoral administration were composed of an immunostimulant such as IL-2 adsorbed to a depot such as aluminum hydroxide, and did not contain antigenic tumor cells. It is because of this characteristic of their composition that the intratumoral preparations are not referred to with the term "vaccine."

The vaccines containing irradiated tumor cells and IL-2 that was not adsorbed to depot material were prepared by mixing an appropriate volume of a cell suspension with an appropriate volume of sterile IL-2 solution as indicated in the foregoing description of the preparation of cytokine depot tumor vaccines.

Calcium phosphate was used as depot material, but calcium phosphate is not as strong an adsorbent for proteins as aluminum hydroxide is. Vaccines with calcium phosphate are consequently more voluminous than similar aluminum hydroxide containing vaccines because larger amounts of calcium phosphate have to be used to bind the required amount of IL-2 per vaccine. The volume of vaccines with calcium phosphate generally exceeded the volume of 100 μl that was otherwise the standard vaccine volume.

The calcium phosphate material used in the context of this invention was the material "Calcium Phosphate Adjuvant" produced by Superfos Biosector AS, Kvistgaard, Denmark, with 1.0% of calcium phosphate in the gel. Since the adsorption capacity of calcium phosphate is about 100 times lower than that of aluminum hydroxide, i e., 1.0 μg IL-2/100 μg CP, 100 fold larger amounts of calcium phosphate gel have to be used.

To prepare the vaccine for an exemplary number of 9 animals, the following amounts are used. 1.0 ml of the calcium phosphate gel is added to and thoroughly mixed with 100 µl of sterile IL-2 solution containing 100 µg IL-2. About 900 µl of a cell suspension containing the appropriate number of irradiated tumor cells—for example, $10^7$ irradiated tumor cells—are mixed with the 1100 µl of the IL-2 adsorbed to calcium phosphate preparation. 200 µl of this mixture containing irradiated tumor cells and IL-2 adsorbed to calcium phosphate are injected into each animal.

Other substances that have been used as adsorbents for IL-2 include talcum, methylcellulose and polystyrene beads. Calcium and methylcellulose are not as good as AL and CP. Polystyrene ("Latex") beads are very good adsorbent material for IL-2, but they have a completely different in vitro IL-2 release pattern. In general, any material that can adsorb proteins, e.g., ion exchangers, and are not toxic to living beings, are in principle candidates for depot materials. However, AL and, to a lesser extent, CP appear to be the preferred materials for this purpose.

It is shown in the context of this invention that it is not necessary to inject the tumor cells adsorbed to the AL depot, but the tumor cells just have to be present in a mixture in the same inoculum. This is an important advantage because by not having to adsorb the tumor cells to the AL depot, the cytokine can be kept adsorbed to the depot preparation in a storage place and then used in a variety of procedures. These procedures include mixing the cytokine adsorbed on a depot preparation with inactivated tumor cells for cellular tumor-specific cytolytic responses, injecting into tumor lesions, and mixing with soluble antigens (e.g., toxoids) for the preparation of vaccines. In contrast, it has been shown in the context of this invention that tumor cell lyzates are preferably adsorbed to aluminum hydroxide and then applied mixed with the aluminum hydroxide adsorbed cytokine.

It has been shown in the context of this invention that the release of cytokines depends on the density of cytokine molecules loaded to AL (as µg cytokine/µg AL). Thus, 10 µg AL are just sufficient to bind 10 µg IL-2, with about 80–90% IL-2 bound, and 100 µg AL completely bind 10 µg IL-2. The results obtained in experiments performed in the context of this invention show that:

(a) The higher the amount of AL that is used to adsorb a certain amount of cytokine, the higher the percentage of the cytokine actually adsorbed to AL, but the lower the release rate and the longer the release time.

(b) The lower the amount of AL that is used to adsorb a certain amount of cytokine, the lower the percentage of the cytokine actually adsorbed to AL, but the higher the release rate and the shorter the release time.

(c) 10 µg IL-2 adsorbed to 10 µg AL appears to be the optimal ratio for use in tumor vaccines.

The three strains of inbred mice used in the experiments discussed hereinbelow are is named BALB/c, a white mouse with the $H-2^{d/d}$ haplotype, C57BL/6, a black mouse with the $H2^{b/b}$ haplotype, and C3H1He, an agouti-colored mouse of the $H-2^{k/k}$ haplotype. Cell culture medium (e.g, RPMI 1640), was used as control in all the vaccination protocols and saline solution was used as control in intratumoral experiments.

For a general practical reference manual on immunochemical techniques, see, for example, Terry M. Phillips, *Analytical Techniques in Immunochemistry*, Marcel Dekker, New York 1992, the disclosure of which is incorporated by reference herein. Immunization techniques for intradermal, intramuscular, intraperitoneal, and intravenous immunization that produce good results for most applications have been described. Id. at pp. 312–14.

The abbreviated notation for dosages in this specification and its accompanying claims consists in the name or symbol of the component preceded by the quantitative expression of its dosage in the appropriate units. For example, "10 µg IL-2" stands for "IL-2 at a dose of about 10 µg per vaccine".

Each one of the aforementioned references is hereby incorporated by reference for the material disclosed therein.

EXAMPLE 1

Therapeutic Vaccination Experiment

Renal carcinoma was induced into mice via intraperitoneal injection of a lethal dose of vital carcinoma cells. Four days later, the mice were vaccinated with the compositions described in the first column of Table 1. Each vaccination group was composed of ten mice. Mice in the first group received a therapeutic composition that comprised about $10^6$ inactivated RenCa cells with no cytokine and no depot. The composition for the second group comprised 10 µg IL-2 adsorbed to about 10 µg of aluminum hydroxide (AL) depot but no RenCa cells. The composition administered to the mice in the third group comprised about $10^6$ inactivated RenCa cells and aluminum hydroxide depot, but no cytokine. Mice in the fourth group received $10^6$ RenCa cells and about 10 µg IL-2 per vaccine, but no depot. Mice in the fifth group received a composition comprising about $10^6$ inactivated RenCa cells, about 10 µg IL-2, adsorbed to about 10 µg of aluminum hydroxide depot. Only the medium that was used in the other preparations was administered to mice in the sixth group, which did not receive any inactivated RenCa cells, cytokine or aluminum hydroxide. For each vaccination group, the tumor induction and vaccination information is summarized in the corresponding row in Table 1.

TABLE 1

| vaccination group | n | day −4 | day 0 |
|---|---|---|---|
| 1  $10^6$ RenCa | 10 | i.p. tumor induction | s.c. vaccination |
| 2  10 µg IL-2 AL | 10 | i.p. tumor induction | s.c. vaccination |
| 3  $10^6$ RenCa AL | 10 | i.p. tumor induction | s.c. vaccination |
| 4  $10^6$ RenCa 10 µg IL-2 | 10 | i.p. tumor induction | s.c. vaccination |
| 5  $10^6$ RenCa 10 µg IL-2 AL | 10 | i.p. tumor induction | s.c. vaccination |
| 6  Medium (RPMI 1640) | 10 | i.p. tumor induction | s.c. injection |

FIG. 1 shows the survival plot for this example. Sixty days after vaccination, no mouse had survived in any one of the vaccination groups except for the fourth and fifth groups. About 30% of the mice that had been vaccinated with about 10 µg IL-2 and about $10^6$ inactivated RenCa cells (Group 4) survived for a period of 60 days after vaccination, and this population was still alive 100 days after vaccination. Notably, 100% of the mice that had been vaccinated with about $10^6$ inactivated RenCa cells, about 10 µg IL-2 adsorbed to about to about 10 µg of aluminum hydroxide depot (Group 5) were alive 100 days after vaccination.

This example discloses the most preferred composition in this invention. This composition comprises about $10^6$ inactivated RenCa cells, IL-2 at a dose of about 10 µg adsorbed to about 10 µg aluminum hydroxide depot. Variables such as amount of antigenic tumor cells in the form of inactivated tumor cells, type of adjuvant, the type and amount of cytokine that are administered in a therapeutic treatment, and antigenicity and immunogenicity of tumor cells are further analyzed in the following examples.

EXAMPLE 2

Therapeutic Vaccination Experiment

Renal carcinoma was induced into mice via intraperitoneal injection of a lethal dose of vital carcinoma cells to test the influence of tumor cell dose on survival. Four days later, the mice were vaccinated with the compositions described in the first column of Table 2.

TABLE 2

| vaccination group | n | day −4 | day 0 |
|---|---|---|---|
| 1  $10^6$ RenCa 10 μg IL-2 AL | 8 | i.p. tumor induction | s.c. vaccination |
| 2  $10^5$ RenCa 10 μg IL-2 AL | 8 | i.p. tumor induction | s.c. vaccination |
| 3  $10^4$ RenCa 10 μg IL-2 AL | 8 | i.p. tumor induction | s.c. vaccination |
| 4  $10^3$ RenCa 10 μg IL-2 AL | 8 | i.p. tumor induction | s.c. vaccination |
| 5  $10^2$ RenCa 10 μg IL-2 AL | 5 | i.p. tumor induction | s.c. vaccination |
| 6  10 μg IL-2 AL | 5 | i.p. tumor induction | s.c. vaccination |
| 7  $10^6$ RenCa | 5 | i.p. tumor induction | s.c. vaccination |
| 8  Medium (RPMI 1640) | 5 | i.p. tumor induction | s.c. injection |

Vaccination groups 1–4 were composed of 8 mice each and vaccination groups 5–7 comprised mice each, with the eighth group being the control group with five mice also. The therapeutic composition that was administered to mice in groups 1–5 comprised about 10 μg IL-2 adsorbed to about 10 μg of aluminum hydroxide. In addition, the composition administered to mice in group j included about $10^{(7-j)}$ inactivated RenCa cells, for groups j=1, 2, 3, 4, 5, respectively. The composition administered to mice in group 6 comprised about 10 μg IL-2 adsorbed to about 10 μg of aluminum hydroxide, but no RenCa cells, whereas the composition administered to mice in group comprised about $10^6$ inactivated RenCa cells. Group 8 was the control group.

Figure 2:
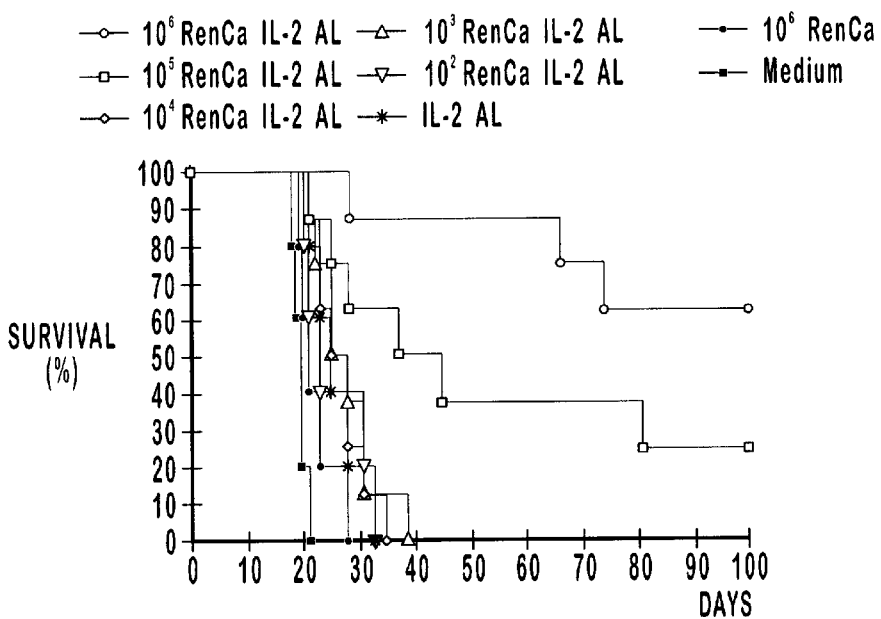
FIG. 2 is a survival plot for a RenCa therapeutic study with different tumor cell dosages.

FIG. 2 shows the survival plot for this example. No mice had survived 40 days after vaccination except for mice in the groups that were vaccinated with preparations that contained more than $10^4$ inactivated RenCa cells. More precisely, the mice that had been vaccinated with a preparation that contained about $10^6$ inactivated RenCa cells, about 10 μg IL-2 adsorbed to about 10 μg of aluminum hydroxide depot experienced a survival rate of about 62% 100 days after vaccination.

The significances computed at day 100 after vaccination are as follows:

| | |
|---|---|
| $10^6$ RenCa 10 μg IL-2 AL vs. 10 μg IL-2 AL; 0.0007 | (2.1) |
| $10^5$ RenCa 10 μg IL-2 AL vs. 10 μg IL-2 AL; 0.0317 | (2.2) |
| $10^4$ RenCa 10 μg IL-2 AL vs. 10 μg IL-2 AL; 0.6878 | (2.3) |
| $10^3$ RenCa 10 μg IL-2 AL vs. 10 μg IL-2 AL; 0.6488 | (2.4) |
| $10^2$ RenCa 10 μg IL-2 AL vs. 10 μg IL-2 AL; 0.9549 | (2.5) |
| $10^6$ RenCa 10 μg IL-2 AL vs. $10^5$ RenCa 10 μg IL-2 AL; 0.0988 | (2.6) |
| $10^6$ RenCa 10 μg IL-2 AL vs. $10^4$ RenCa 10 μg IL-2 AL; 0.0003 | (2.7) |
| $10^5$ RenCa 10 μg IL-2 AL vs. $10^4$ RenCa 10 μg IL-2 AL; 0.0198 | (2.8) |
| $10^5$ RenCa 10 μg IL-2 AL vs. $10^3$ RenCa 10 μg IL-2 AL; 0.0389 | (2.9) |
| 10 μg IL-2 vs. $10^6$ RenCa; 0.2189 | (2.10) |
| 10 μg IL-2 AL vs. Medium; 0.0112 | (2.11) |

The set of five significances (2.1) through (2.5) leads to the acceptance of the explanation that an amount of inactivated RenCa cells above 104 together with 10 μg IL-2 adsorbed to about 10 μg aluminum hydroxide depot significantly increases the survival of mice in favor of the alternative explanation that is based on the administration of a preparation with only about 10 μg IL-2 adsorbed to about 10 μg of aluminum hydroxide depot. More particularly, the set of four significances (2.6) through (2.9) leads to the acceptance of the explanation that an amount of inactivated RenCa cells above $10^4$ together with about 10 μg IL-2 adsorbed to about 10 μg of aluminum hydroxide depot significantly increase the survival of mice over the alternative explanation that is based on the administration of a preparation with about $10^4$ inactivated RenCa cells or less, about 10 μg IL-2 adsorbed to about 10 μg of aluminum hydroxide depot. Significance (2.6) in the preceding group indicates that, at a slightly less than 10% significance level, the acceptance of the explanation that about $10^6$ inactivated RenCa cells together with about 10 μg IL-2 adsorbed to about 10 μg of aluminum hydroxide depot significantly increase the survival of mice in favor of the alternative explanation that is based on the administration of a preparation with about $10^5$ inactivated RenCa cells, about 10 μg IL-2 adsorbed to about 10 μg of aluminum hydroxide depot. Significance (2.10) indicates that the explanations for survival in groups 6 and 7 are not statistically distinguishable, at the 21.89% significance level, in terms of the administration of about 10 μg IL-2 adsorbed to about 10 μg of aluminum hydroxide depot to mice in group 6 and the administration of about $10^6$ inactivated RenCa cells to mice in group 7. Finally, significance (2.11) indicates that the survival in group 6 is due to the administration to mice in this group of about 10 μg IL-2 adsorbed to about 10 μg of aluminum hydroxide depot and not due to the vaccination medium that was administered to mice in group 8, at least at a 1.12% significance level. The analysis of the results of this experiment according to the Logrank test for trend shows that survival depends in an extremely significant manner on the dose of irradiated RenCa cells in the vaccine (p<0.001).

In sum, the results of this study indicate that a threshold of about $10^6$ inactivated RenCa cells in the vaccine provides superior survival rates over those provided by preparations that contain lower inactivated cell densities.

EXAMPLE 3

Therapeutic Vaccination Experiment

The number of tumor cells plays a role in the composition of the vaccination preparation and also in the composition of the tumor induction preparation. The tumor cells are inactive in the vaccination preparation and the effect of the number of inactivated tumor cells in therapeutic vaccination has been analyzed in Example 2. The tumor cells are active or vital (hereinafter "vit") in the tumor induction preparations of the therapeutic vaccination study in this example. The number of tumor cells used to induce a tumor is hereinafter referred to as "tumor burden".

As shown in Table 3, the vaccination groups comprised 10 mice each. The amount of vit B16 cells used to induce tumors were about $10^4$, about $10^3$ and about $10^2$. Mice with tumors induced by each one of these preparations were therapeutically vaccinated with preparations that comprised about $10^5$ inactivated B16 cells alone or about $10^5$ inactivated B16 cells with about 10 μg IL-2 adsorbed to about 10 μg of aluminum hydroxide depot. The corresponding vaccination groups and tumor induction groups are shown in columns 2 and 4 in Table 3, respectively. Because multiple vaccinations were administered to each vaccination group in this study, column 5 in the same table shows the vaccination days for the mice in each group.

TABLE 3

| vaccination group | n | tumor induction | vaccine composition and vaccination days |
|---|---|---|---|
| 1 $10^5$ B16 10 μg IL-2 AL | 10 | s.c. tumor induction $10^4$ vit B16 (Day −4) | s.c. vaccination B16 IL-2 AL (day 0, 7, 14, 21, 28) |
| 2 $10^5$ B16 | 10 | s.c. tumor induction $10^4$ vit B16 (Day −4) | s.c. vaccination B16 (Day 0, 7, 14, 21) |
| 3 Medium (RPMI 1640) | 10 | s.c. tumor induction $10^4$ vit B16 (Day −4) | s.c. injection Medium (Day 0, 7, 14) |
| 4 $10^5$ B16 10 μg IL-2 AL | 10 | s.c. tumor induction $10^3$ vit B16 (Day −4) | s.c. vaccination B16 IL-2 AL (day 0, 7, 14, 21, 28, 35) |
| 5 $10^5$ B16 | 10 | s.c. tumor induction $10^3$ vit B16 (Day −4) | s.c. vaccination B16 (Day 0, 7, 14, 21, 28) |
| 6 Medium (RPMI 1640) | 10 | s.c. tumor induction $10^3$ vit B16 (Day −4) | s.c. injection Medium (Day 0, 7, 14, 21, 28) |
| 7 $10^5$ B16 10 μg IL-2 AL | 10 | s.c. tumor induction $10^2$ vit B16 (Day −4) | s.c. vaccination B16 IL-2 AL (day 0, 7, 14, 21, 28, 35, 42) |
| 8 $10^5$ B16 | 10 | s.c. tumor induction $10^2$ vit B16 (Day −4) | s.c. vaccination B16 (Day 0, 7, 14, 21, 28, 35, 42) |
| 9 Medium (RPMI 1640) | 10 | s.c. tumor induction $10^2$ vit B16 (Day −4) | s.c. injection Medium (Day 0, 7, 14, 21, 28) |

Figure 3:
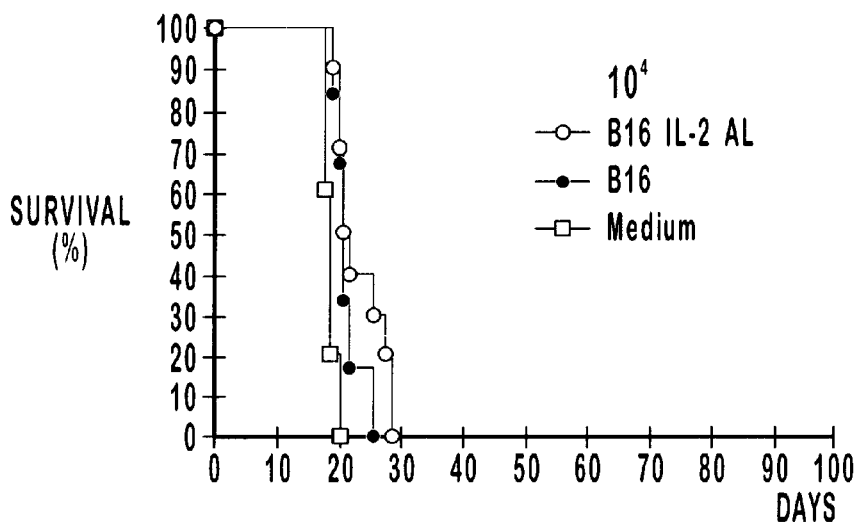
FIG. 3 is a survival plot for a B therapeutic study with a tumor cell induction dosage of $10^4$ vital B16 cells.
Figure 4:
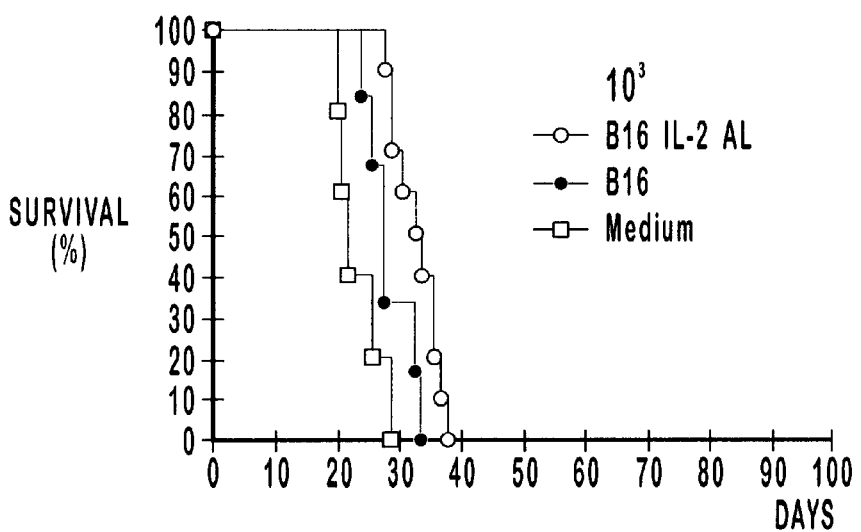
FIG. 4 is a survival plot for a B16 therapeutic study with a tumor cell induction dosage of $10^3$ vital B16 cells.
Figure 5:
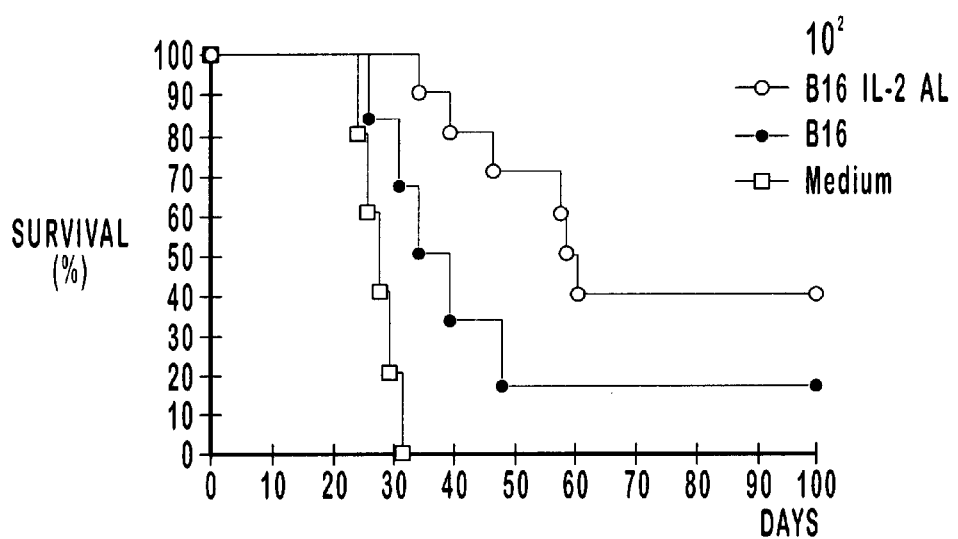
FIG. 5 is a survival plot for a B16 therapeutic study with a tumor cell induction dosage of $10^2$ vital B16 cells.

FIGS. 3–5 show the survival plots for tumor loads of about $10^4$, about $10^3$ and about $10^2$, respectively. Even with multiple vaccination with a preparation that comprised inactivated tumor cells and IL-2 adsorbed to aluminum hydroxide depot, no mice survived for more than 40 days when the tumor load was of about $10^3$ or more vit B16 cells. When the tumor load was reduced to about $10^2$, however, about 40% of the mice survived after being vaccinated at seven day intervals, seven times, starting four days after the tumor induction day.

The significances computed at day 100 after the initial vaccination are as follows:

s.c. tumor induction $10^4$ vit B16 (Day −4):

| | |
|---|---|
| $10^5$ B16 10 μg IL-2 AL vs. $10^5$ B16; 0.2425 | (3.1) |
| $10^5$ B16 10 μg IL-2 AL vs. Medium; 0.0012 | (3.2) |
| $10^5$ B16 vs. Medium; 0.0107 | (3.3) | s.c. tumor induction $10^3$ vit B16 (Day −4):

| | |
|---|---|
| $10^5$ B16 10 μg IL-2 AL vs. $10^5$ B16; 0.0312 | (3.4) |
| $10^5$ B16 10 μg IL-2 AL vs. Medium; 0.0099 | (3.5) |
| $10^5$ B16 vs. Medium; 0.0834 | (3.6) | s.c. tumor induction $10^2$ vit B16 (Day −4):

| | |
|---|---|
| $10^5$ B16 10 μg IL-2 AL vs. $10^5$ B16; 0.0846 | (3.7) |
| $10^5$ B16 10 μg IL-2 AL vs. Medium; <0.0001 | (3.8) |
| $10^5$ B16 vs. Medium; 0.0222 | (3.9) |
| $10^5$ B16 10 μg IL-2 AL ($10^2$) vs. $10^5$ B16 10 μg IL-2 AL ($10^3$); <0.0001 | (3.10) |
| $10^5$ B16 10 μg IL-2 AL ($10^2$) vs. $10^5$ B16 10 μg IL-2 AL ($10^4$); <0.000 | (3.11) |
| $10^5$ B16 10 μg IL-2 AL ($10^3$) vs. $10^5$ B16 10 μg IL-2 AL ($10^4$); 0.0001 | (3.12) |

Any one of the two vaccination preparations used in this example caused an increase in the survival rate when compared with the medium effects, as significances (3.2), (3.3), (3.5), (3.6), (3.8), and (3.9) indicate. However, the effects of the preparation with about $10^5$ inactivated B16 cells, about 10 μg IL-2 adsorbed to about 10 μg of aluminum hydroxide depot cannot be statistically differentiated from those of the preparation with about $10^5$ inactivated B16 cells, but no IL-2 or aluminum hydroxide depot, unless the tumor load is less than or equal to about $10^3$, as significances (3.1), (3.4) and (3.7) indicate. Finally, the lower the tumor load, the higher the increase in survival achieved by the therapeutic vaccination with the preparation that includes about $10^5$ inactivated B16 cells, about 10 μg IL-2 adsorbed to about 10 μg of aluminum hydroxide depot, as can be concluded by comparing significances (3.10), (3.11) and (3.12). (Powers of ten within parenthesis in significances (3.10), (3.11) and (3.12) refer to the numbers of vit B16 cells in the tumor induction preparations). The analysis of the results of this experiment according to the Logrank test for trend shows that vaccination efficiency depends in an extremely significant manner on the tumor load present before the start of the vaccination (p<0.0001).

EXAMPLE 4

Prophylactic Vaccination Experiment

The influence of the number of inactivated tumor cells in the vaccination composition on survival is analyzed here in a B16 prophylactic study. Prophylactic vaccination was administered four times prior to day 0 (hereinafter "challenge day") when the mice were subcutaneously injected a dose of tumor inducing preparation. Specifically, the prophylactic vaccinations were administered four times (4×) on days 35, 28, 21, and 14 prior to the challenge day. The control group comprised 5 mice that were subcutaneously injected medium on the same vaccination days that the mice in the vaccination groups were subcutaneously injected the corresponding vaccination preparation. Vaccination group 1 comprised 8 mice, and the vaccination preparation included about $10^5$ inactivated B116 cells, and about 10 μg IL-2 adsorbed to about 10 μg of aluminum hydroxide depot. Vaccination groups 2 and 3 comprised 6 mice each. The vaccination preparations in groups 2 and 3 differed from the preparation in group 1 in that the preparation in group 2 included about $10^6$ inactivated B16 cells and the preparation in group 3 included about $10^7$ inactivated B16 cells. Both preparations also contained about 10 μg IL-2 adsorbed to about 10 μg of aluminum hydroxide depot. Vaccination group 4 also comprised 6 mice, but the vaccination preparation only included about $10^5$ inactivated B16 cells, but no IL-2 or aluminum hydroxide. These characteristics are summarized in Table 4.

TABLE 4

| vaccination group | n | day -35 | day -28 | day -21 | day -14 | day 0 |
|---|---|---|---|---|---|---|
| 1  $10^5$ B16 10 µg IL-2 AL (4x) | 8 | s.c. B16 IL-2 AL | s.c. B16 IL-2 AL | s.c. B16 IL-2 AL | s.c. B16 IL-2 AL | s.c. challenge |
| 2  $10^6$ B16 10 µg IL-2 AL (4x) | 6 | s.c. B16 IL-2 AL | s.c. B16 IL-2 AL | s.c. B16 IL-2 AL | s.c. B16 IL-2 AL | s.c. challenge |
| 3  $10^7$ B16 10 µg IL-2 AL (4x) | 6 | s.c. B16 IL-2 AL | s.c. B16 IL-2 AL | s.c. B16 IL-2 AL | s.c. B16 IL-2 AL | s.c. challenge |
| 4  $10^5$ B16 (4x) | 6 | s.c. B16 | s.c. B16 | s.c. B16 | s.c. B16 | s.c. challenge |
| 5  Medium (4x) | 5 | s.c. Medium | s.c. Medium | s.c. Medium | s.c. Medium | s.c. challenge |

Figure 6:
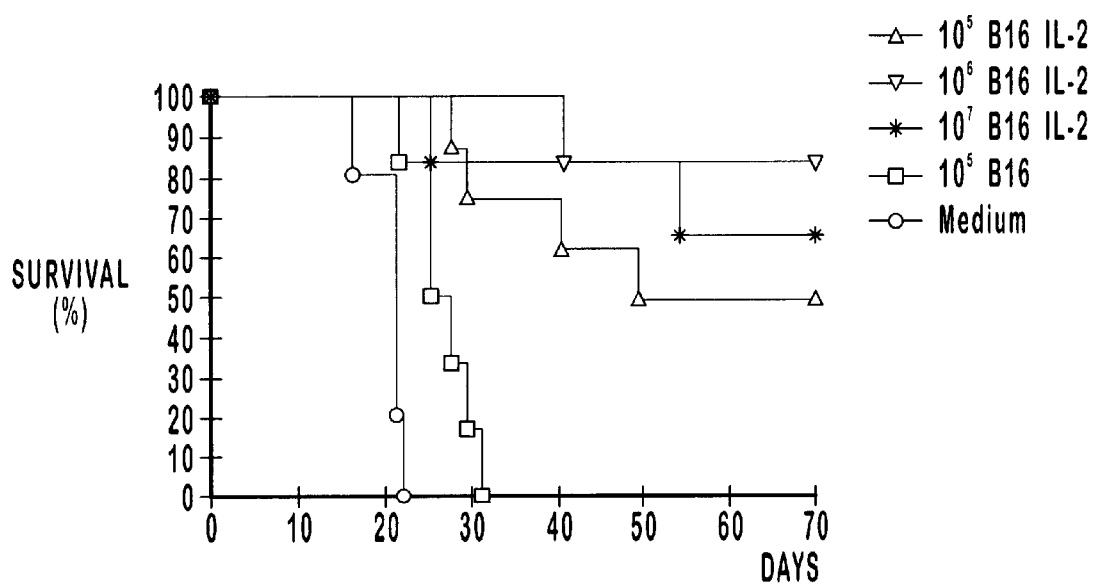
FIG. 6 is a survival plot for a B16 prophylactic study with different tumor cell vaccination dosages.

FIG. 6 shows a survival plot for this prophylactic study. No mice in vaccination group 4 were alive 35 days after the challenge day, whereas at least 50% of the mice in any one of groups 1–3 had survived for 70 days after the challenge day. The survival rates for these three groups in particular show that when the number of inactivated B16 cells in the vaccination preparation is too high, mice developed tolerance. These survival rates also show that when the number of these cells was too low, the preparation was less effective. An intermediate number of about $10^6$ inactivated B16 cells in particular, led to the highest survival rate of over 80% seventy days after the challenge day. This interpretation is consistent with the measured survival rates of less than 70% when the number of inactivated B16 cells in the vaccination preparation is about $10^7$, and about 50% when the number of inactivated B16 cells in the vaccination preparation is about $10^5$.

Figure 7:
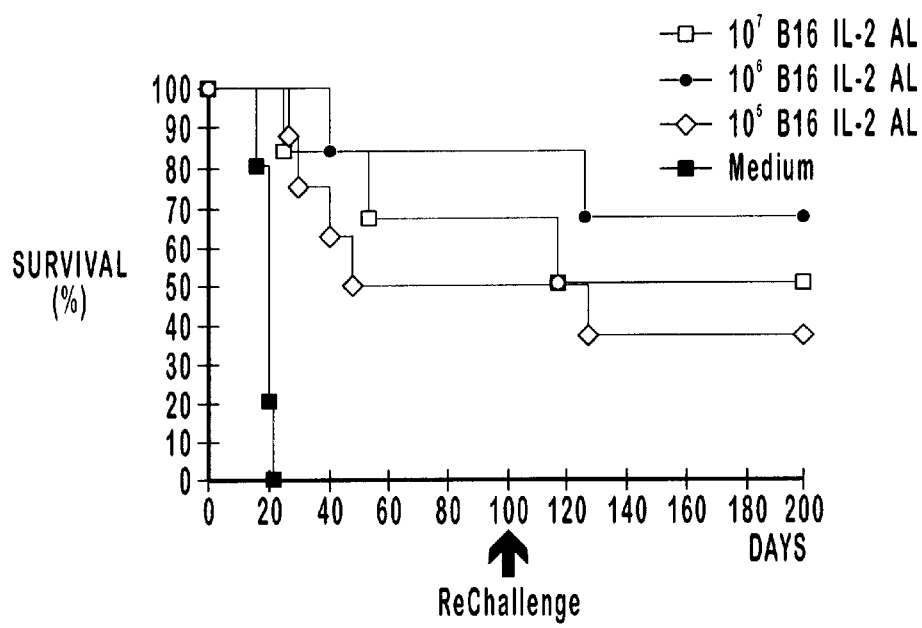
FIG. 7 is a survival plot for a B16 prophylactic study with different tumor cell vaccination dosages.

FIG. 7 shows a survival plot for this prophylactic study in which mice that were alive on day 100 after the initial challenge day were re-challenged on day 100. The vaccination preparation that includes about $10^6$ inactivated B16 cells is the preparation that provided the best survival rate of over 65% at day 200 after the initial challenge day. The survival rates on the same day 200 were about 50% and less than 40% for the groups that were vaccinated with preparations that included about $10^7$ and about $10^5$ inactivated B16 cells, respectively. These results are again consistent with the interpretation that an intermediate number of about $10^6$ inactivated tumor cells is preferred, with a higher number leading to tolerance and a smaller number leading to a lower survival rate.

The significances computed at day 100 after challenge day are as follows:

$10^5$ B16 10 µg IL-2 AL (4x) vs. Medium (4x); 0.0002

$10^6$ B16 10 µg IL-2 AL (4x) vs. Medium (4x); 0.0009

$10^7$ B16 10 µg IL-2 AL (4x) vs. Medium (4x); 0.0009

These significances indicate that any one of the vaccination preparations that included inactivated B16 cells, IL-2 and aluminum hydroxide caused an increase in the survival rate when compared with the medium effect on survival rate. The analysis of the results of this experiment according to the Logrank test for trend shows that dependence on cell dose is not significant in this case.

EXAMPLE 5

Therapeutic Vaccination Experiment

Renal carcinoma was induced into mice via intraperitoneal injection of a lethal dose of vital cacinoma cells to determine the preferred quantity of IL-2. Four days later, the mice were vaccinated with the compositions described in the second column of Table 5. Vaccination groups 1–5 were composed of six mice each, vaccination group 6 comprised 5 mice and the control group, or group 5 in this example, comprised mice. Mice in groups 1–6 received a therapeutic composition that included about $10^6$ inactivated RenCa cells. In addition, the compositions administered to mice in groups 1–5 included IL-2. In particular, the IL-2 dosages were about 3 µg in compositions administered to mice in groups 1 and 4, about 10 µg in compositions administered to mice in groups 2 and 5, and about 30 µg in the composition administered to mice in group 3. Furthermore, the compositions administered to mice in groups 4 and 5 included aluminum hydroxide depot to which the IL-2 was adsorbed in ratios of 10 µg of IL-2 to 10 µg of aluminum hydroxide and 10 µg IL-2 to 10 µg of aluminum hydroxide, respectively. To achieve a localized effect with the compositions that include no aluminum hydroxide depot, the vaccination compositions administered to mice in groups 1–3 were adsorbed onto the tumor cells themselves.

TABLE 5

| vaccination group | n | day -4 | day 0 |
|---|---|---|---|
| 1  $10^6$ RenCa 3 µg IL-2 | 6 | i.p. tumor induction | s.c. vaccination |
| 2  $10^6$ RenCa 10 µg IL-2 | 6 | i.p. tumor induction | s.c. vaccination |
| 3  $10^6$ RenCa 30 µg IL-2 | 6 | i.p. tumor induction | s.c. vaccination |
| 4  $10^6$ RenCa 3 µg IL-2 AL | 6 | i.p. tumor induction | s.c. vaccination |
| 5  $10^6$ RenCa 10 µg IL-2 AL | 6 | i.p. tumor induction | s.c. vaccination |
| 6  $10^6$ RenCa | 5 | i.p. tumor induction | s.c. vaccination |
| 7  Medium (RPMI 1640) | 4 | i.p. tumor induction | s.c. injection |

Figure 8:
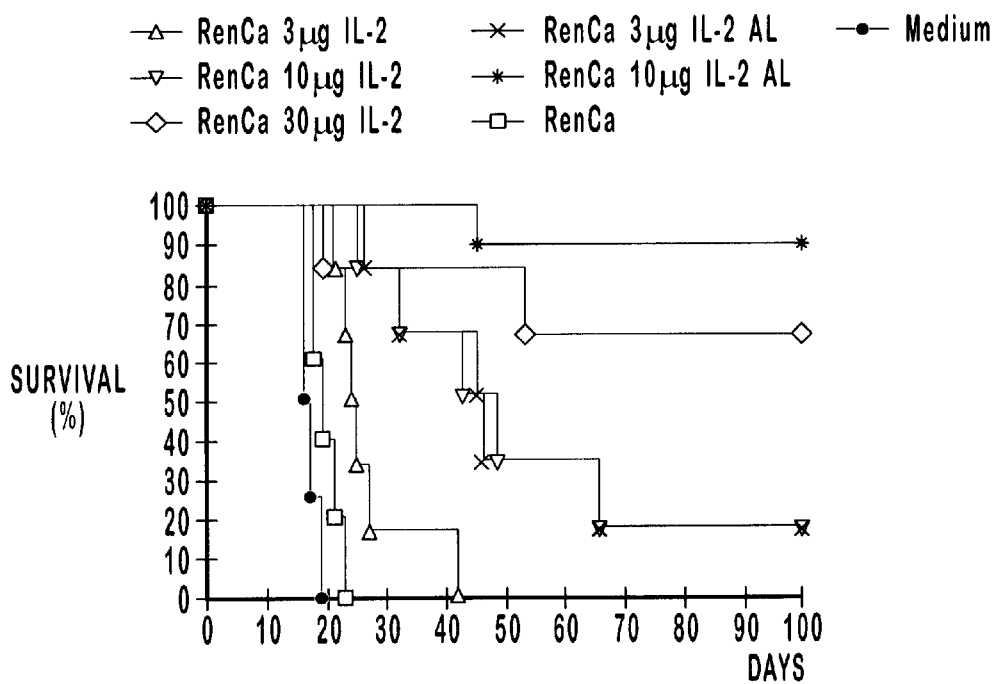
FIG. 8 is a survival plot for a RenCa therapeutic study with different IL-2 dosages with and without depot.

FIG. 8 shows a survival plot for this example. All of the mice in the control group (group 7) and in the group that was vaccinated with a preparation that did not include IL-2 or aluminum hydroxide (group 6) died within less than 25 days after vaccination. Measurable survival beyond day 50 after vaccination was recorded in vaccination groups 2–5. As shown in FIG. 8, less than 20% of the mice in groups 2 and 4 survived until day 100 after vaccination, slightly over 65% of the mice in group 3 survived for the same period of time, and 90% of the mice in group survived for 100 days after vaccination with a preparation that contained about $10^6$ inactivated RenCa cells and about 10 µg IL-2, adsorbed to about 10 µg of aluminum hydroxide depot. Consistently with the results discussed in example 1, a vaccination preparation that includes about $10^6$ inactivated RenCa cells, about 10 µg IL-2 adsorbed to about 10 µg of aluminum hydroxide is the preferred preparation according to this invention. Furthermore, the survival rates for groups 2 and 4, and independently for groups 3 and 5, indicate that the use of aluminum hydroxide in the vaccination preparation leads to the same or even greater survival rate than that achieved by using a preparation with a higher dose of IL-2 but with no aluminum hydroxide.

EXAMPLE 6

Therapeutic Vaccination Experiment

Renal carcinoma was induced into mice via intraperitoneal injection of a lethal dose of vital carcinoma cells. Four days later, the mice were vaccinated with the compositions described in the second column of Table 6. Vaccination group 1 comprised seven mice. Vaccination groups 2 and 3 were composed of six mice each, vaccination group 4 comprised 5 mice and the control group, or group 5 in this example, comprised mice. Mice in groups 1–4 received a therapeutic composition that included about $10^6$ inactivated RenCa cells. In addition, the compositions administered to mice in groups 1–3 included IL-2. In particular, the IL-2 dosages were about 3 μg in compositions administered to mice in groups 3 and 4, about 10 μg in compositions administered to mice in groups 2, and about 30 μg in the composition administered to mice in group 3. No vaccination composition in this example included aluminum hydroxide depot; the cytokine was applied adsorbed to the tumor cells.

TABLE 6

| vaccination group | n | day −4 | day 0 |
|---|---|---|---|
| 1  $10^6$ RenCa 3 μg IL-2 | 7 | i.p. tumor induction | s.c. vaccination |
| 2  $10^6$ RenCa 10 μg IL-2 | 6 | i.p. tumor induction | s.c. vaccination |
| 3  $10^6$ RenCa 30 μg IL-2 | 6 | i.p. tumor induction | s.c. vaccination |
| 4  $10^6$ RenCa | 5 | i.p. tumor induction | s.c. vaccination |
| 5  Medium (RPMI 1640) | 5 | i.p. tumor induction | s.c. injection |

Consistently with the results discussed in Example 5, and absent the depot effects of aluminum hydroxide, the highest survival rate was observed in the group whose vaccination composition included about 30 μg IL-2. The survival plot shown in FIG. 9 reveals that between 65% and 70% of the mice that had been vaccinated with this composition were alive 100 days after vaccination, but only between 15% and 20% of the mice that had been vaccinated with a composition that included about 10 μg IL-2 were alive on the same day, and none of the mice that had been vaccinated with a composition that included about 3 μg IL-2 survived for 50 days after vaccination day. The survival rate of the mice that had been vaccinated with inactivated RenCa cells only was 0 prior to the 25th day after vaccination day.

Figure 9:
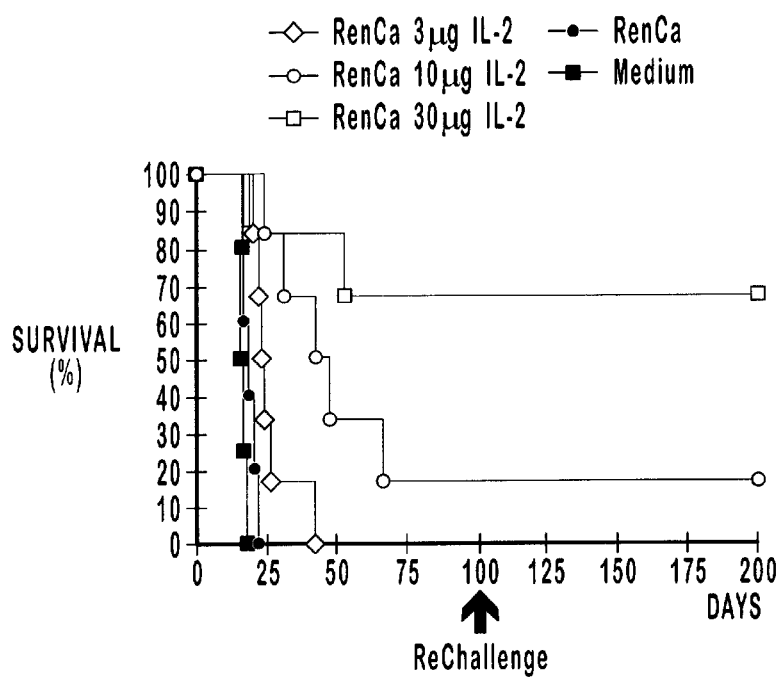
FIG. 9 is a survival plot for a RenCa therapeutic study with different IL-2 dosages without depot.

Mice in groups 2 and three that were alive on day 100 were re-challenged by intraperitoneal administration of the same tumor induction composition that had been administered to them four days prior to vaccination. As FIG. 9 shows, the number of mice alive in each group remained constant for another 100-day period, thus indicating that the prophylactic effect of the vaccination compositions used in groups 2 and 3 were equally positive in the respective mice populations. The effect was long lasting.

EXAMPLE 7

Therapeutic Vaccination Experiment

Renal carcinoma was induced into mice via intraperitoneal injection of a lethal dose of vital carcinoma cells. Four days later, the mice were vaccinated with the compositions described in the second column of Table 7. Vaccination group 4 comprised seven mice. Vaccination groups 2 and 3 were composed of six mice each, vaccination group 4 comprised 5 mice and the control group, or group 5 in this example, comprised mice. Mice in groups 1–4 received a therapeutic composition that included about $10^6$ inactivated RenCa cells. In addition, the compositions administered to mice in groups 1–3 included IL-2. In particular, the IL-2 dosages were about 10 μg adsorbed to about 10 μg of aluminum hydroxide depot in compositions administered to mice in group 1, about 10 μg adsorbed to about 10 μg of aluminum hydroxide depot in compositions administered to mice in group 2, and about 30 μg adsorbed to about 30 μg of aluminum hydroxide depot in the composition administered to mice in group 3. Neither IL-2 nor aluminum hydroxide were part of the vaccination composition administered to mice in group 4.

TABLE 7

| vaccination group | n | day −4 | day 0 |
|---|---|---|---|
| 1  $10^6$ RenCa 3 μg IL-2 AL | 7 | i.p. tumor induction | s.c. vaccination |
| 2  $10^6$ RenCa 10 μg IL-2 AL | 6 | i.p. tumor induction | s.c. vaccination |
| 3  $10^6$ RenCa 30 μg IL-2 AL | 6 | i.p. tumor induction | s.c. vaccination |
| 4  $10^6$ RenCa | 5 | i.p. tumor induction | s.c. vaccination |
| 5  Medium (RPMI 1640) | 5 | i.p. tumor induction | s.c. injection |

Figure 10:
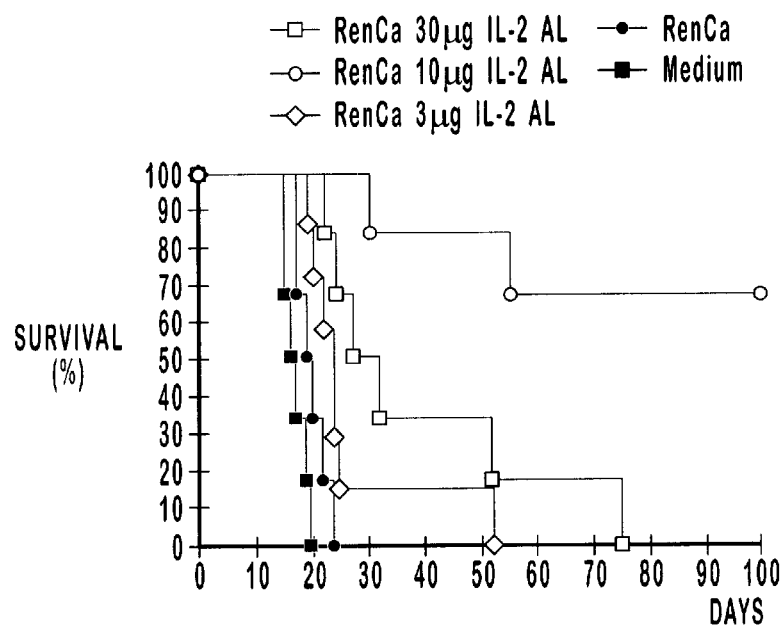
FIG. 10 is a survival plot for a RenCa therapeutic study with different IL-2 dosages with aluminum hydroxide depot.

The survival plot shown in FIG. 10 reveals that there is a cytokine dosage window that maximizes survival rate when administered with about $10^6$ inactivated RenCa cells and aluminum hydroxide depot. Between 65% and 70% of the mice in group 2 survived for 100 days after vaccination, whereas no mice in group 3 survived for more than 80 days and the survival time for any mice in group 1 was less than 55 days. Consistently with the previous example, the survival time of mice in group 1 was near 55 days after vaccination. The optimum dosage of cytokine was over 10 μg adsorbed to about 10 μg of aluminum hydroxide depot and less than 30 μg adsorbed to about 30 μg of aluminum hydroxide depot; more specifically, the preferred dose was about 10 μg IL-2 adsorbed to about 10 μg of aluminum hydroxide depot administered with about $10^6$ inactivated RenCa cells.

The significances computed at day 100 after the initial vaccination are as follows:

| | |
|---|---|
| $10^6$ RenCa 3 μg IL-2 AL vs. $10^6$ RenCa 10 μg IL-2 AL; 0.0011 | (7.1) |
| $10^6$ RenCa 3 μg IL-2 AL vs. $10^6$ RenCa 30 μg IL-2 AL; 0.1339 | (7.2) |
| $10^6$ RenCa 3 μg IL-2 AL vs. $10^6$ RenCa; 0.0642 | (7.3) |
| $10^6$ RenCa 3 μg IL-2 AL vs. Medium; 0.0019 | (7.4) |
| $10^6$ RenCa 10 μg IL-2 AL vs. $10^6$ RenCa 30 μg IL-2 AL; 0.0117 | (7.5) |
| $10^6$ RenCa 10 μg IL-2 AL vs. $10^6$ RenCa; 0.0005 | (7.6) |
| $10^6$ RenCa 10 μg IL-2 AL vs. Medium; 0.0005 | (7.7) |
| $10^6$ RenCa 30 μg IL-2 AL vs. $10^6$ RenCa; 0.0045 | (7.8) |
| $10^6$ RenCa 30 μg IL-2 AL vs. Medium; 0.0005 | (7.9) |
| $10^6$ RenCa vs. Medium; 0.0097 | (7.10) |

The preceding significances support the explanation that the administration of vaccination compositions that contain IL-2 adsorbed to aluminum hydroxide in addition to inactivated RenCa cells more positively affects the survival rate of the vaccinated populations than the administration of compositions that do not contain aluminum hydroxide and cytokine. See significances (7.3), (7.4), (7.6), (7.7), (7.8) and (7.9). Significance (7.5) indicates explanation that the increased survival rate is due to the administration of about $10^6$ inactivated RenCa cells with about 10 μg IL-2 adsorbed to about 10 μg of aluminum hydroxide depot instead of being due to the administration of about $10^6$ inactivated RenCa cells with about 30 μg IL-2 adsorbed to about 30 μg of aluminum hydroxide depot is to be accepted at a 1.17% significance level.

EXAMPLE 8

Therapeutic Vaccination Experiment

Renal carcinoma was induced into mice via intraperitoneal injection of a lethal dose of vital carcinoma cells. Four days later, the mice were vaccinated with the compositions described in the second column of Table 8. Vaccination groups 1, 2 and 4 comprised ten mice each. Vaccination group 3 was composed of nine mice, vaccination group 5 and the control group, or group 6 in this example, comprised 5 mice each. Mice in groups 1–4 received therapeutic composition that included about $10^6$ inactivated RenCa cells. In addition, the compositions administered to mice in groups 1–4 included IL-2. In particular, the IL-2 dosages were about 10 μg adsorbed to about 10 μg of aluminum hydroxide compositions administered to mice in group 1, about 10 μg adsorbed to about 10 μg of aluminum hydroxide in compositions administered to mice in group 2, about 10 μg adsorbed to about 1 μg of aluminum hydroxide in the composition administered to mice in group 3, and about 0.3 μg adsorbed to about 0.3 μg of aluminum hydroxide in composition administered to mice in group 4. Neither IL-2 nor aluminum hydroxide were part of the vaccination composition administered to mice in group 5.

TABLE 8

| vaccination group | n | day −4 | day 0 |
|---|---|---|---|
| 1 $10^6$ RenCa 10 μg IL-2 AL | 10 | i.p. tumor induction | s.c. vaccination |
| 2 $10^6$ RenCa 3 μg IL-2 AL | 10 | i.p. tumor induction | s.c. vaccination |
| 3 $10^6$ RenCa 1 μg IL-2 AL | 9 | i.p. tumor induction | s.c. vaccination |
| 4 $10^6$ RenCa 0.3 μg IL-2 AL | 10 | i.p. tumor induction | s.c. vaccination |
| 5 $10^6$ RenCa | 5 | i.p. tumor induction | s.c. vaccination |
| 6 Medium (RPMI 1640) | 5 | i.p. tumor induction | s.c. injection |

Figure 11:
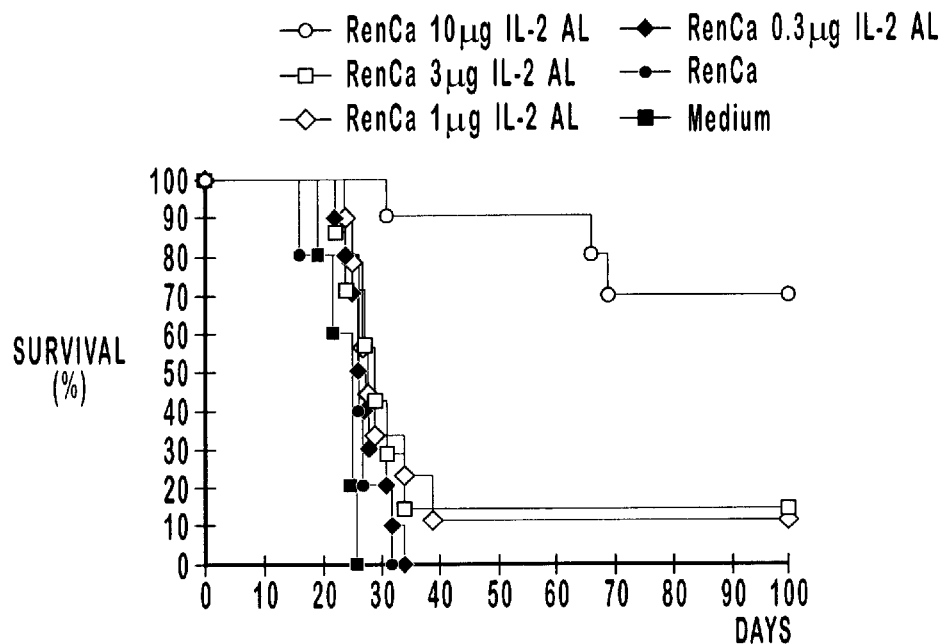
FIG. 11 is a survival plot for a RenCa therapeutic study with different IL-2 dosages with aluminum hydroxide depot.

The survival plot shown in FIG. 11 reveals that cytokine dosages of less than about 10 μg IL-2 are typically ineffective in maintaining a significant survival rate. About 70% of the mice in group 1 survived for 100 days after vaccination, whereas 25% or less of the mice in groups 2 and 3 survived for the same period of time. Consistently with Examples 6 and 7, the optimum dosage of cytokine was not less than about 10 μg; more specifically, the preferred dose was about 10 μg IL-2 adsorbed to about 10 μg of aluminum hydroxide administered with about $10^6$ inactivated RenCa cells. The significances computed at day 100 after the initial vaccination are as follows:

| | |
|---|---|
| $10^6$ RenCa 10 μg IL-2 AL vs. $10^6$ RenCa; <0.0001 | (8.1) |
| $10^6$ RenCa 3 μg IL-2 AL vs. $10^6$ RenCa; 0.2718 | (8.2) |
| $10^6$ RenCa 1 μg IL-2 AL vs. $10^6$ RenCa; 0.1546 | (8.3) |
| $10^6$ RenCa 0.3 μg IL-2 AL vs. $10^6$ RenCa; 0.7010 | (8.4) |
| $10^6$ RenCa 10 μg IL-2 AL vs. $10^6$ RenCa 3 μg IL-2 AL; 0.0028 | (8.5) |
| $10^6$ RenCa 10 μg IL-2 AL vs. $10^6$ RenCa 1 μg IL-2 AL; 0.0009 | (8.6) |
| $10^6$ RenCa 3 μg IL-2 AL vs. $10^6$ RenCa 1 μg IL-2 AL; 0.9770 | (8.7) |
| $10^6$ RenCa 3 μg IL-2 AL vs. $10^6$ RenCa 0.3 μg IL-2 AL; 0.3429 | (8.8) |

Significances (8.1), (8.2), (8.3) and (8.4) support the explanation that positive effects of IL-2 adsorbed to aluminum hydroxide with inactivated tumor cells on survival are statistically less significant as the dosages of IL-2 in the vaccination preparation becomes less than about 10 μg. More particularly, significances (8.5) and (8.6) indicate that the positive effect of the preferred composition on survival is an explanation that has to be accepted over alternative explanations that are based on lower dosages of IL-2 with at significance levels of less than 0.3%. Significances (8.7) and (8.8) indicate that the cause for survival of the individuals in the vaccination group characterized by $10^6$ RenCa 10 μg IL-2 AL are statistically indistinguishable from the cause for survival of the individuals in the vaccination groups characterized by $10^6$ RenCa 10 μg IL-2 AL and by $10^6$ RenCa 0.3 μg IL-2 AL.

The analysis of the results of this experiment according to the Logrank test for trend shows that survival depends in a very significant manner on the dose of the AL adsorbed cytokine in the vaccine (p=0.0016). It has been shown in the context of this invention that survival depends in an extremely significant manner on the number of vaccinations (p<0.0001), with vaccinations being better than vaccinations, which in turn were better than 2 vaccinations, and 2 vaccinations were better than 1 vaccination which was better than the administration of cells alone, in turn better than the administration of medium.

EXAMPLE 9

Prophylactic Vaccination Experiment

The influence of the IL-2 dose in the vaccination composition on survival is analyzed here in a B16 prophylactic study. Prophylactic vaccination was administered four times (4×) prior to day 0 (hereinafter "challenge day") when the mice were subcutaneously injected a dose of tumor inducing preparation. Specifically, the prophylactic vaccinations were administered 35, 28, 21, and 14 days prior to the challenge day. The control group comprised mice that were subcutaneously injected medium on the same vaccination days that the mice in the vaccination groups were subcutaneously injected the corresponding vaccination preparation. Vaccination group 1 comprised 6 mice, and the vaccination preparation included about $10^5$ inactivated B16 cells and about 30 μg IL-2. Vaccination groups 2 and 3 comprised 7 and 8 mice, respectively. The vaccination preparations in groups 2 and 3 differed from the preparation in group 1 in that the preparation in group 2 included about 10 μg IL-2 and the preparation in group 3 included about 10 μg IL-2. Vaccination group 4 also comprised about $10^5$ inactivated B16 cells, but no IL-2 or aluminum hydroxide. Because none of the preparations in this example included an aluminum hydroxide depot, IL-2 at the indicated dosages was adsorbed to tumor cells, so that the cells themselves became the depot. These characteristics are summarized in Table 9.

TABLE 9

| vaccination group | n | day −35 | day −28 | day −21 | day −14 | day 0 |
|---|---|---|---|---|---|---|
| 1 $10^5$ B16 30 μg IL-2 (4×) | 6 | s.c. B16 IL-2 | s.c. B16 IL-2 | s.c. B16 IL-2 | s.c. B16 IL-2 | s.c. challenge |
| 2 $10^5$ B16 10 μg IL-2 (4×) | 7 | s.c. B16 IL-2 | s.c. B16 IL-2 | s.c. B16 IL-2 | s.c. B16 IL-2 | s.c. challenge |
| 3 $10^5$ B16 3 μg IL-2 (4×) | 8 | s.c. B16 IL-2 | s.c. B16 IL-2 | s.c. B16 IL-2 | s.c. B16 IL-2 | s.c. challenge |
| 4 $10^5$ B16 (4×) | 5 | s.c. B16 | s.c. B16 | s.c. B16 | s.c. B16 | s.c. challenge |
| 5 Medium (4×) | 6 | s.c. Medium | s.c. Medium | s.c. Medium | s.c. Medium | s.c. challenge |

Figure 12:
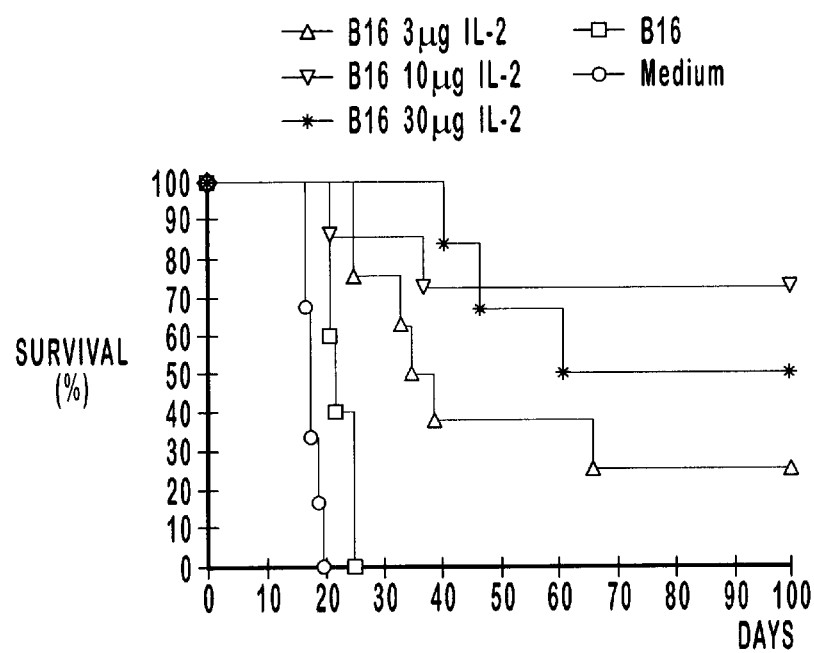
FIG. 12 is a survival plot for a B16 prophylactic study with different IL-2 dosages without aluminum hydroxide depot.

FIG. 12 shows a survival plot for this prophylactic study. These results indicate that the composition that had the most favorable effect on survival included cytokine at a dosage of about 10 μg. In particular, about 70% of the mice that had been repeatedly vaccinated with a composition that included 10 μg IL-2 survived for 100 days following challenge day. In contrast, only about 50% of the mice that had been vaccinated with a composition that included about 30 μg IL-2 survived for the same time, and about 25% of the mice that had been vaccinated with a composition that included about 10 μg IL-2 survived at the end of the same time period. No mice in vaccination group 4 was alive 30 days after the challenge day.

The survival rates for groups 1–3 show that there is a cytokine dose window at which the preparation of this invention achieves the optimum effect on survival rate in prophylactic treatment of tumors. Within this window, the preferred dosage is about 10 μg IL-2. Other preparations that also contained about $10^5$ inactivated B16 cells and IL-2 were not as effective in maintaining relatively high survival rates when the IL-2 doses were about 30 μg and about 10 μg. The results obtained in the B16 prophylactic model of this invention show that survival extremely significantly depends on cytokine dose.

EXAMPLE 10

Therapeutic Vaccination Expenment

Renal carcinoma was induced into mice via intraperitoneal injection of a lethal dose of vital carcinoma cells to determine the influence of depot form on survival. Four days later, the mice were vaccinated with the compositions described in the second column of Table 10. Vaccination groups 1, 2 and 3 comprised ten mice each. Vaccination group 4 was When control group with 3 mice. Mice in groups 1–3 received a therapeutic composition that included about $10^6$ inactivated RenCa cells. In addition, the compositions administered to mice in groups 1–2 included about 10 μg IL-2. The IL-2 in the vaccination compositions administered to mice in groups 1 and 2 was adsorbed to aluminum hydroxide depots and encapsulated in liposome depots (hereinafter "Lip"), respectively.

TABLE 10

| vaccination group | n | day −4 | day 0 |
|---|---|---|---|
| 1 | $10^6$ RenCa 10 μg IL-2 AL | 10 | i.p. vaccination | i.p. challenge |
| 2 | $10^6$ RenCa 10 μg IL-2 Lip | 10 | i.p. vaccination | i.p. challenge |
| 3 | $10^6$ RenCa | 10 | i.p. vaccination | i.p. challenge |
| 4 | Medium (RPMI 1640) | 3 | i.p. injection | i.p. challenge |

Figure 13:
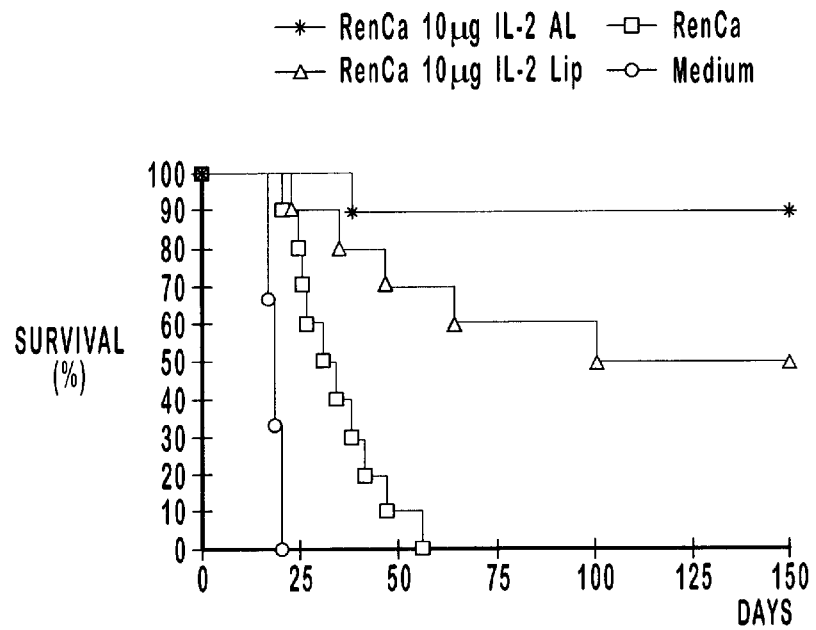
FIG. 13 is a RenCa therapeutic study with different depot forms.

FIG. 13 shows in a survival plot that about 90% of the mice that had been vaccinated with the composition that contained aluminum hydroxide adsorbed IL-2 survived 150 days after vaccination. In contrast, the survival rate in the group whose individuals were administered the same amount of IL-2 encapsulated in liposomes was significantly lower, at a 50% for the same time period. Therefore, the IL-2 AL preparation is preferable to the IL-2 Lip preparation, The significances computed at day 150 after the initial vaccination are as follows:

| | |
|---|---|
| $10^6$ RenCa 10 μg IL-2 AL vs. $10^6$ RenCa; <0.0001 | (10.1) |
| $10^6$ RenCa 10 μg IL-2 AL vs. Medium; <0.0001 | (10.2) |
| $10^6$ RenCa 10 μg IL-2 Lip vs. $10^6$ RenCa; 0.0011 | (10.3) |
| $10^6$ RenCa 10 μg IL-2 Lip vs. Medium; <0.0001 | (10.4) |
| $10^6$ RenCa 10 μg IL-2 Lip vs. $10^6$ RenCa 10 μg IL-2 AL; 0.1330 | (10.5) |

Significances (10.1), (10.2), (10.3) and (10.4) indicate that the positive effect of compositions that include IL-2 in a depot formulation on survival is an explanation that has to be accepted over alternative explanations that are based on compositions with either no depot or with no depot and no cytokine. Significance (10.5) indicates that the cause of survival of the individuals in the vaccination group characterized by $10^6$ RenCa 10 μg IL-2 Lip and of the individuals in the vaccination group characterized by $10^6$ RenCa 10 μg IL-2 AL are different at the 13.30% significance level.

EXAMPLE 11

Therapeutic Vaccination Experiment

Renal carcinoma was induced into mice via intraperitoneal injection of a lethal dose of vital carcinoma cells. Four days later, the mice were vaccinated with the compositions described in the second column of Table 11.

TABLE 11

| vaccination group | n | day −4 | day 0 |
|---|---|---|---|
| 1 $10^6$ RenCa 10 μg IL-2 AL | 10 | i.p. tumor induction | s.c. vaccination |
| 2 $10^6$ RenCa 10 μg IL-2 CP | 10 | i.p. tumor induction | s.c. vaccination |
| 3 $10^6$ RenCa 10 μg IL-4 AL | 5 | i.p. tumor induction | s.c. vaccination |
| 4 $10^6$ RenCa | 5 | i.p. tumor induction | s.c. vaccination |
| 5 Medium (RPMI 1640) | 7 | i.p. tumor induction | s.c. injection |

Vaccination groups 1 and 2 comprised ten mice each. Vaccination groups 3 and 4 were composed of five mice each, and the control group, or group 5 in this example, comprised 7 mice. Mice in groups 1–4 received a therapeutic composition that included about $10^6$ inactivated RenCa cells. In addition, the compositions administered to mice in groups 1–3 included a cytokine. This cytokine was IL-2 in groups 1 and 2, but it was IL-4 in group 3. Any one of these cytokines was delivered at a dose of about 10 μg. About 10 μg of IL-2 in vaccination group 1 and about 10 μg of IL-2 in vaccination group 3 was adsorbed to about 10 μg of aluminum hydroxide whereas the composition administered to the individuals in group 2 contained about 10 μg of IL-2 adsorbed to about 1000 μg of calcium phosphate (CP). The vaccination composition administered to mice in group 4 did not contain cytokine or any depot formulation, whether calcium phosphate or aluminum hydroxide.

Figure 14:
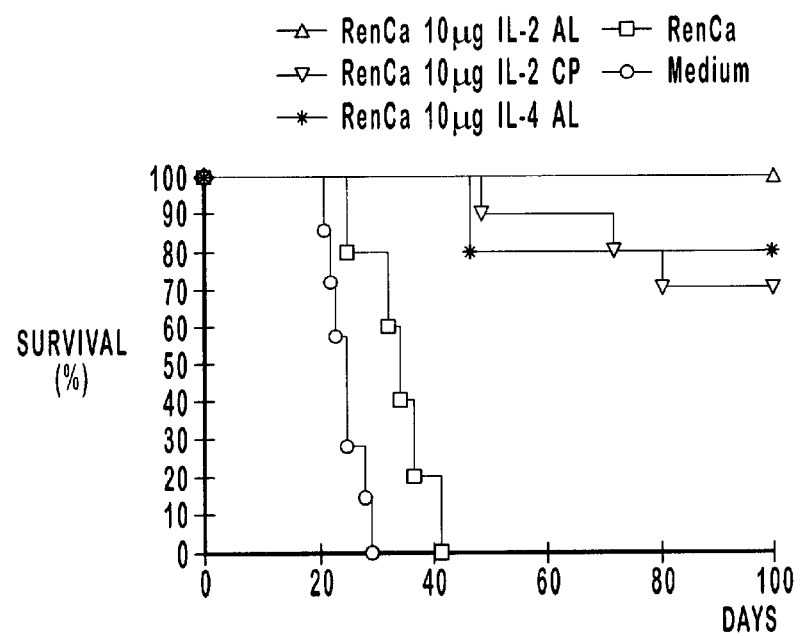
FIG. 14 is a RenCa therapeutic study with different depot forms and different cytokines.

The survival plot shown in FIG. 14 reveals that the influence of aluminum hydroxide on survival was more positive than that of calcium phosphate, whether administered with IL-2 or with IL-4. 100% of the mice that had been vaccinated with the composition $10^6$ RenCa 10 μg IL-2 AL were alive 100 days after vaccination, 80% of those vaccinated with the composition $10^6$ RenCa 10 μg IL-2 AL were alive at the end of the same time period, and about 70% of those vaccinated with the composition $10^6$ RenCa 10 μg IL-2 CP were alive for the same time. The preparation with IL-2 had effects on survival rates that were more positive than those due to the preparation with IL-4.

The significances computed at day 100 after the initial vaccination are as follows:

| | |
|---|---|
| $10^6$ RenCa 10 μg IL-2 AL vs. $10^6$ RenCa; <0.0001 | (11.1) |
| $10^6$ RenCa 10 μg IL-2 CP vs. $10^6$ RenCa; <0.0001 | (11.2) |
| $10^6$ RenCa 10 μg IL-4 AL vs. $10^6$ RenCa; 0.0018 | (11.3) |

Significances (11.1), (11.2), and (11.3) indicate that the positive effect on survival of compositions that include cytokine adsorbed to either aluminum hydroxide or CP is an explanation that has to be accepted over alternative explanations that are based on compositions with no depot and no cytokine. No significant difference was observed between the survivals in groups $10^6$ RenCa 10 μg IL-2 AL and $10^6$ RenCa 10 μg IL-2 CP and between the survivals in the groups $10^6$ RenCa 10 μg IL-2 AL and $10^6$ RenCa 10 μg IL-2 AL.

EXAMPLE 12

Prophylactic Vaccination Experiment

The influence on survival of the cytokine depot in the vaccination composition is analyzed here in a B16 prophylactic study. Prophylactic vaccination was administered four times (4×) prior to day 0 (hereinafter "challenge day") when the mice were subcutaneously injected a dose of tumor inducing preparation. Specifically, the prophylactic vaccinations were administered 35, 28, 21, and 14 days prior to the challenge day. The control group comprised 5 mice that were subcutaneously injected medium on the same vaccination days that the mice in the vaccination groups were subcutaneously injected the corresponding vaccination preparation. Vaccination group 1 comprised 8 mice, and the vaccination preparation was $10^5$ B16 10 μg IL-2 AL. Vaccination group 2 comprised 9 mice, and the vaccination preparation was $10^5$ B16 10 μg IL-2 CP. The vaccination preparation for group 3 with 6 mice was $10^5$ B16, and group 4 was the control group with 5 mice. These characteristics are summarized in Table 12.

TABLE 12

| vaccination group | n | day −35 | day −28 | day −21 | day −14 | day 0 |
|---|---|---|---|---|---|---|
| 1 $10^5$ B16 10 μg IL-2 AL (4x) | 8 | s.c. B16 IL-2 AL | s.c. B16 IL-2 AL | s.c. B16 IL-2 AL | s.c. B16 IL-2 AL | s.c. challenge |
| 2 $10^5$ B16 10 μg IL-2 CP (4x) | 9 | s.c. B16 IL-2 CP | s.c. B16 IL-2 CP | s.c. B16 IL-2 CP | s.c. B16 IL-2 CP | s.c. challenge |
| 3 $10^5$ B16 (4x) | 6 | s.c. B16 | s.c. B16 | s.c. B16 | s.c. B16 | s.c. challenge |
| 4 Medium (4x) | 5 | s.c. Medium | s.c. Medium | s.c. Medium | s.c. Medium | s.c. challenge |

Figure 15:
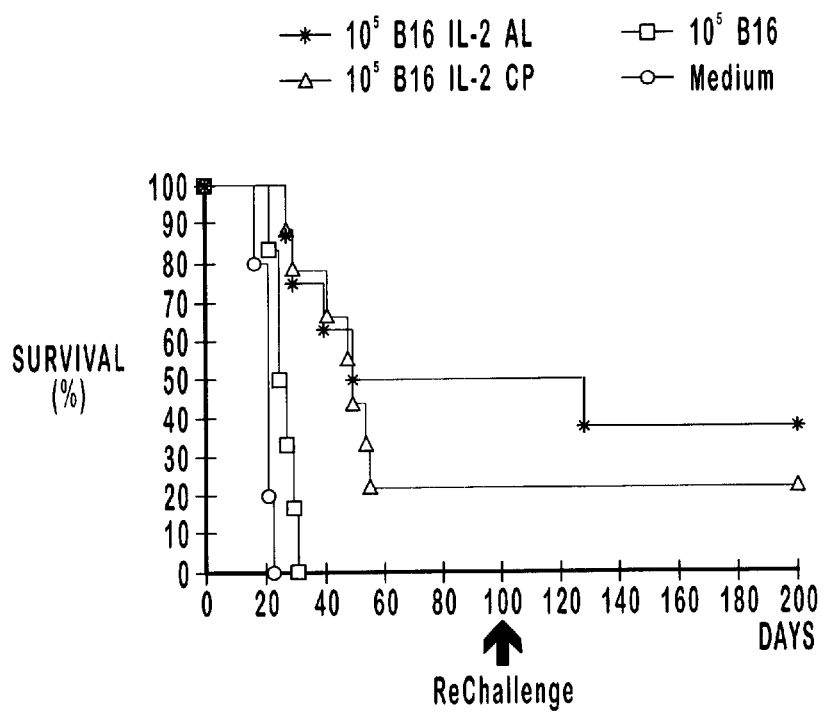
FIG. 15 is a survival plot for a B16 prophylactic study with different depot forms.

Consistently with the results analyzed in Example 11, the survival plot shown in FIG. 15 reveals that 50% of the mice in the group that had been vaccinated with a preparation that included cytokine adsorbed to aluminum hydroxide survived for a 70-day period after challenge day, but the survival rate for the same time period was only about 20% for the group whose mice had been vaccinated with a preparation that included IL-2 adsorbed to calcium phosphate instead of IL-2 adsorbed to aluminum hydroxide.

The significances computed at day 100 after the initial vaccination are as follows:

| | |
|---|---|
| $10^5$ B16 10 μg IL-2 AL (4x) vs. $10^5$ B16 10 μg IL-2 CP (4x); 0.6002 | (12.1) |
| $10^5$ B16 10 μg IL-2 AL (4x) vs. $10^5$ B16 (4x); 0.0024 | (12.2) |
| $10^5$ B16 10 μg IL-2 AL (4x) vs. Medium (4x); 0.0002 | (12.3) |
| $10^5$ B16 10 μg IL-2 CP (4x) vs. $10^5$ B16 (4x); 0.0011 | (12.4) |
| $10^5$ B16 10 μg IL-2 CP (4x) vs. Medium (4x); <0.0001 | (12.5) |
| $10^5$ B16 (4x) vs. Medium (4x); 0.0061 | (12.6) |

Significance (12.1) means that, although the survival rate of the mice treated with AL-containing vaccines is overall better as shown in FIG. 15, the difference is not significant. This is mainly due to the fact that the two corresponding curves practically have an identical course for survival rates between 100% and 50%, or for the time period 0–50 days. This parallelism in the first part of the two survival curves has a great effect on the statistical Significance and the two curves that appear so different from each other in FIG. 15 are not significantly different according to the statistical test used in the analysis of the results herein described. Significances (12.2), (12.3), (12.4), and (12.5) indicate that the positive effect on survival of compositions that include IL-2 adsorbed to an adsorbent as an adjuvant is an explanation that has to be accepted over alternative explanations that are based on compositions with no adjuvant and no cytokine. Significance (12.6) indicates that the positive effect on survival of compositions that include inactivated B16 cells is an explanation that has to be accepted over an alternative explanation that is based on compositions with no depot, no cytokine and no inactivated B16 cells.

Influence of Other Immunostimulating Substances on Survival

In contrast with recombinant human IL-2 that is commercially available, other cytokines are less available or they do not exhibit biological cross-reaction with respect to human beings and mice. Despite these drawbacks, experiments have been performed in the context of this invention with other cytokines. allogeneic Although IL-2 seems to develop into one of the more important cytokines, it is not readily available and IL-2 used in these experiments was obtained under non-commercial restricted distribution terms. Recombinant human IL-2 is applied for treatment of human beings, and it was observed that IL-12 can work very efficiently at relatively small doses.

Recombinant human G-CSF is commercially available and active in mice as well as in humans. Recombinant human GM-CSF is also commercially available, but it is not biologically active in mice. The murine CRM-CSF used in the experiments discussed herein as purified from the supematant of a GM-CSF gene transfected B16 melanoma cell line.

Recombinant human IL-2 is not commercially available and is not biologically active in mice. The murine IL-2 used in the experiments discussed herein was purified from the supernatant of IL-2 gene transfected P815 mastocytoma cell line.

EXAMPLE 13

Therapeutic Vaccination Experiment

Renal carcinoma was induced into mice via intraperitoneal injection of a lethal dose of vital carcinoma cells. Four days later, the mice were vaccinated with the compositions described in the first column of Table 13. Vaccination groups 1, 2 and 3 comprised five mice each and group 4 was the control group with four mice. Mice in groups 1–2 received a therapeutic composition that included about 10 μg G-CSF adsorbed to aluminum hydroxide each. G-CSF stands for granulocyte colony stimulating factor, which is a cytokine made chiefly by mononuclear phagocytes. In addition, the composition administered to mice in group 1 included about $10^6$ inactivated RenCa cells. The vaccination composition administered to mice in group 3 comprised about $10^6$ inactivated RenCa cells, but did not contain cytokine or any adjuvant, and the composition administered to the control group consisted of medium with no cytokine, RenCa cells or adjuvant. Recombinant human G-CSF is commercially available, but G-CSF is not a preferred cytokine for tumor vaccines.

TABLE 13

| vaccination group | | n | day −4 | day 0 |
|---|---|---|---|---|
| 1 | $10^6$ RenCa 10 μg G-CSF AL | 5 | i.p. tumor induction | s.c. vaccination |
| 2 | 10 μg G-CSF AL | 5 | i.p. tumor induction | s.c. vaccination |
| 3 | $10^6$ RenCa | 5 | i.p. tumor induction | s.c. vaccination |
| 4 | Medium (RPMI 1640) | 4 | i.p. tumor induction | s.c. injection |

Figure 16:
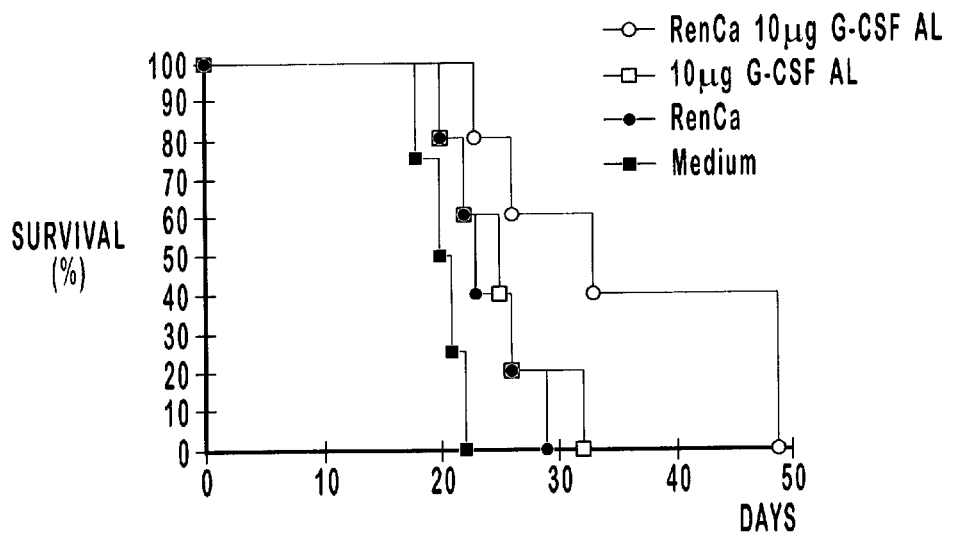
FIG. 16 is a survival plot for a RenCa therapeutic study and cytokine G-CSF.

The survival plot shown in FIG. 16 reveals that even the composition that includes RenCa cells with G-CSF adsorbed to aluminum hydroxide cannot maintain any mice alive beyond day 50 after vaccination.

EXAMPLE 14

Therapeutic Vaccination Experiment

Renal carcinoma was induced into mice via intraperitoneal injection of a lethal dose of vital carcinoma cells. Four days later, the mice were vaccinated with the compositions described in the second column of Table 14. Vaccination groups 1, 2, and 3 comprised six mice each, group 4 comprised five mice, and group 5 was the control group with four mice. Mice in groups 1–4 received a therapeutic composition that included about $10^6$ inactivated RenCa cells. The vaccination compositions administered to mice in groups 2 and 3 also included about 10 μg GM-CSF adsorbed to aluminum hydroxide. GM-CSF stands for granulocyte-macrophage colony stimulating factor, which is a cytokine made by immune system cells that include lymphocytes. The vaccination compositions administered to mice in groups 1 and 3 also included about 3 μg IL-4. The vaccination composition administered to mice in group 4 comprised about $10^6$ inactivated RenCa cells, but did not contain cytokine or depot, and the composition administered to the control group consisted of medium with no cytokine, RenCa cells or depot.

TABLE 14

| vaccination group | | n | day −4 | day 0 |
|---|---|---|---|---|
| 1 | $10^6$ RenCa 3 μg IL-4 AL | 6 | i.p. tumor induction | s.c. vaccination |
| 2 | $10^6$ RenCa 3 μg GM-CSF AL | 6 | i.p. tumor induction | s.c. vaccination |
| 3 | $10^6$ RenCa 3 μg IL-4 AL 3 μg GM-CSF AL | 6 | i.p. tumor induction | s.c. vaccination |
| 4 | $10^6$ RenCa | 5 | i.p. tumor induction | s.c. vaccination |
| 5 | Medium (RPMI 1640) | 4 | i.p. tumor induction | s.c. injection |

Figure 17:
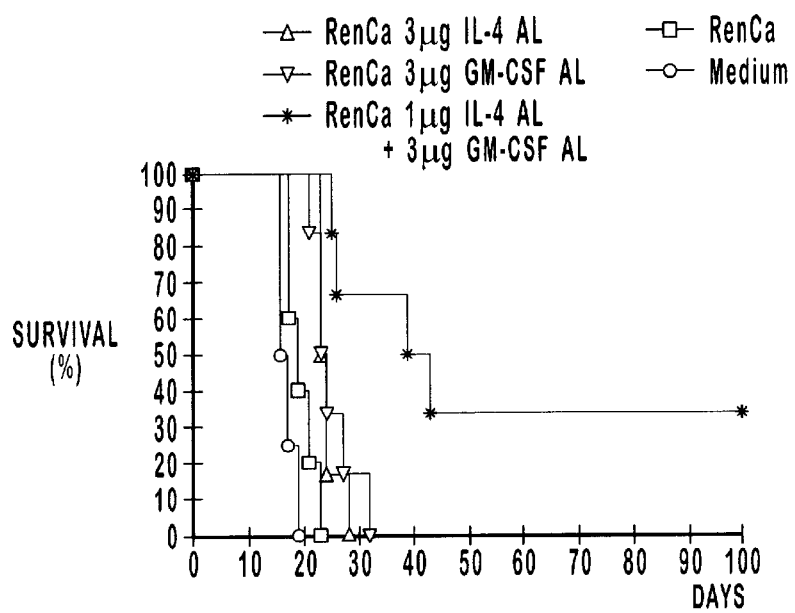
FIG. 17 is a survival plot for a RenCa therapeutic study and GM-CSF and IL-4.

The survival plot shown in FIG. 17 reveals that the only vaccination group with surviving mice on day 35 after vaccination is the group with mice that had been administered IL-2 together with GM-CSF, both in aluminum hydroxide adsorbed form. Between 30% and 35% of the mice in this group were alive on day 100 after vaccination. Although these survival rates are much smaller than those achieved by the preferred composition of this invention, the survival rates shown in FIG. 17 indicate that IL-2 and GM-CSF may, in fact, act synergistically. The results discussed in this Example show that the combination of two cytokines is better than each one of the cytokines alone. Nevertheless, IL-2 is still better than the combination of IL-2 and GM-CSF.

EXAMPLE 15

Therapeutic Vaccination Experiment

Renal carcinoma was induced into mice via intraperitoneal injection of a lethal dose of vital carcinoma cells. Four days later, the mice were vaccinated with the compositions described in the second column of Table 15. Vaccination groups 1–3 comprised five mice each, group 4 comprised six mice, group 5 comprised mice and group 6 was the control group with three mice. Mice in groups 1–5 received a therapeutic composition that included about $10^6$ inactivated RenCa cells or the lyzed equivalent thereof. The vaccination compositions administered to mice in groups 1–4 included RenCA tumor cell lysates instead of intact RenCA tumor cells. To obtain lysates, tumor cells were frozen and thawed several times. In addition, they were treated with ultrasonic waves (sonicated). In other experiments, cell membranes were also used. They were prepared from the lysates by ultracentrifiigation. Membrane vesicles obtained from the culture supernatants of in vitro cultured tumor cells were also used. The compositions in groups 3 and 4 included RenCa tumor cell lyzates adsorbed to aluminum hydroxide, and the compositions in groups 2 and 4 additionally included about 10 μg IL-2 adsorbed to about 10 μg of aluminum hydroxide. The vaccination compostion administered to mice in group 5 comprised about $10^6$ inactivated RenCa cells, but did not contain lysate, cytokine or any depot material, and the composition administered to the control group consisted of medium with no lysate, cytokine, RenCa cells or aluminum hydroxide.

TABLE 15

| vaccination group | | n | day −4 | day 0 |
|---|---|---|---|---|
| 1 | $10^6$ RenCa-Lysat | 5 | i.p. tumor induction | s.c. vaccination |
| 2 | $10^6$ RenCa-Lysat 10 μg IL-2 AL | 5 | i.p. tumor induction | s.c. vaccination |
| 3 | $10^6$ RenCa-Lysat AL | 5 | i.p. tumor induction | s.c. vaccination |
| 4 | $10^6$ RenCa-Lysat AL 10 μg IL-2 AL | 6 | i.p. tumor induction | s.c. vaccination |
| 5 | $10^6$ RenCa | 4 | i.p. tumor induction | s.c. vaccination |
| 6 | Medium (RPMI 1640) | 3 | i.p. tumor induction | s.c. injection |

Figure 18:
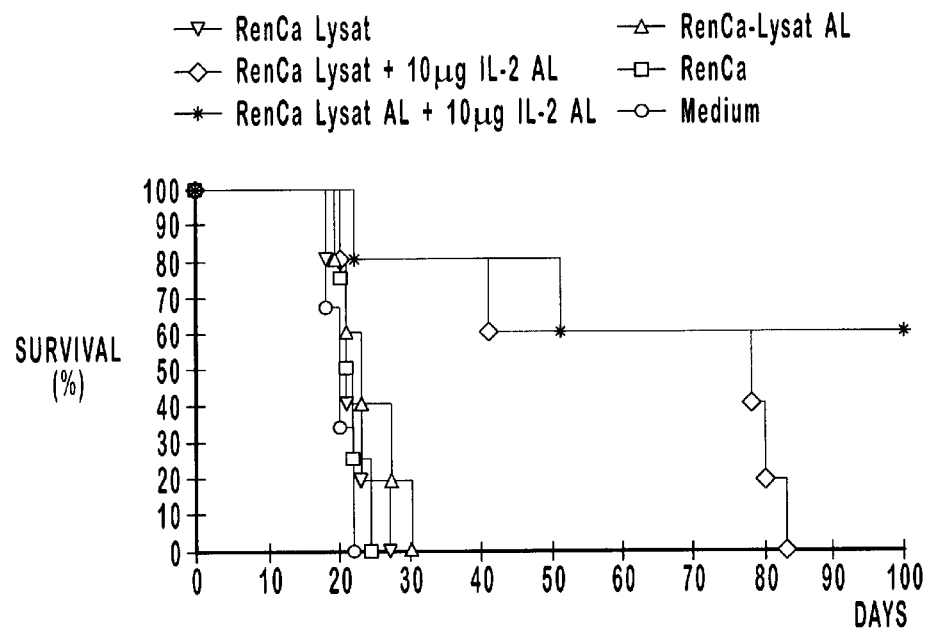
FIG. 18 is a survival plot for a RenCa therapeutic study with RenCa lysate.

The survival plot shown in FIG. 18 reveals that the only vaccination groups with significant survival rates 40 days after vaccination were the groups whose vaccination compositions included IL-2. In particular, the group that had been vaccinated with AL-adsorbed RenCa tumor cell lysate together with about 10 μg IL-2 adsorbed to about 10 μg of aluminum hydroxide depot, maintained a survival rate of 60% through day 100 after vaccination, but the group whose mice had been vaccinated with a free (i.e., not AL-adsorbed) RenCa tumor cell lysate together with about 10 μg IL-2 adsorbed to about 10 μg of aluminum hydroxide depot, which displayed the same survival rate through day 75 after vaccination, did not maintain this survival rate past day 80. These results indicate that the use of tumor cell lysates in vaccination preparations only leads to a significant increase in the survival rate of the vaccinated population if both, the tumor cell lysate and the cytokine (IL-2), are separately adsorbed to AL and then injected as a mixture. It appears that survival prolongation observed in the group vaccinated with a mixture of cell lysate without the AL-depot material and AL-depot adsorbed IL-2 is caused by other effects. In this group the mice lived disease-free for a certain time but then died within a few days. This resembles "stable disease" as it is also observed in tumor patients.

EXAMPLE 16

Prophylactic Transfer Experiment

The influence on survival of transferred spleen cells in the vaccination composition is analyzed in a prophylactic study in which RenCa-immune spleen cells of a vaccinated donor were transferred to BALB/c mice ("adoptive transfer of spleen cells") in groups 1–3. Mice to which tumor was induced by an injection of $10^5$ vital RenCa cells in day −4 were therapeutically vaccinated by a single inoculation with the usual vaccine (about $10^6$ irradiated tumor cells and about 10 µg IL-2 adsorbed to about 10 µg AL). The spleen cells of the surviving animals were harvested 100 days after vaccination. The spleens of the animals were transferred into medium-containing sterile dishes and squeezed with a forceps until the cells were released from the spleen tissue. The cells were counted, and the cell suspension was adjusted to the required density, e.g, about $30 \cdot 10^6$ cells per ml. Then the cells were injected intravenously into the animals (about 1 ml of the cell suspension containing the required amount of cells into each animal). Spleen cells of non-vaccinated donors, or "naive donors" were transferred to mice in group 4 the same day the mice in groups 1–3 received spleen cells of vaccinated donors. All the spleen cell transfers were carried out by intravenous injections. Seven days after the adoptive transfer, mice in groups 1–4 were intraperitoneally injected with vital RenCa tumor cells. This was day 0 or the "challenge day". Groups 1–4 comprised six mice each, and control group number 5 comprised four mice. Mice in groups 1 and 4 received about $30 \cdot 10^6$ spleen cells, mice in group 2 received about $10 \cdot 10^6$ spleen cells, and mice in group received about $3 \cdot 10^6$ spleen cells. These characteristics are summarized in Table 16.

TABLE 16

| | vaccination group | n | day −4 | day 0 |
|---|---|---|---|---|
| 1 | $30 \cdot 10^6$ spleen cells, vaccinated donor | 6 | i.v. cell transfer | i.p. tumor induction |
| 2 | $10 \cdot 10^6$ spleen cells, vaccinated donor | 6 | i.v. cell transfer | i.p. tumor induction |
| 3 | $3 \cdot 10^6$ spleen cells, vaccinated donor | 6 | i.v. cell transfer | i.p. tumor induction |
| 4 | $30 \cdot 10^6$ spleen cells, "naive" donor | 6 | i.v. cell transfer | i.p. tumor induction |
| 5 | Medium (RPMI 1640) | 4 | i.v. injection | i.p. tumor induction |

Figure 19:
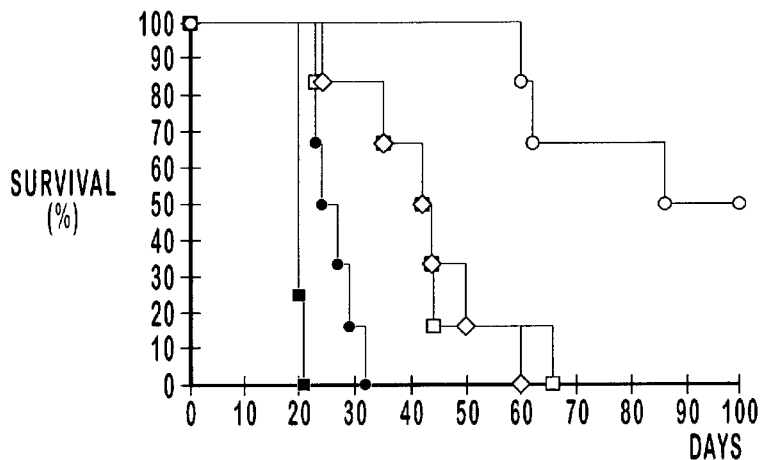
FIG. 19 is a survival plot for a RenCa prophylactic study with adoptive transfer of spleen cells.

As FIG. 19 shows, only the adoptive transfer of $30 \cdot 10^6$ RenCa-immune spleen cells was successful in maintaining a certain number of mice alive 100 days after challenge day. Even in this case, however, the survival rate was about 50%, which is significantly lower than the survival rate achieved after direct vaccination with the preferred composition of this invention. Adoptive transfer of $10 \cdot 10^6$ RenCa immune spleen cells and $3 \cdot 10^6$ RenCa-immune spleen cells led to such considerably lower survival rates that no mice in groups 2 and 3 were alive at day 70 after challenge day. Adoptive transfer of naive spleen cells did not led to the survival of any of the mice in group 4 for over 35 days after challenge day.

The significances computed at day 100 after challenge day are as follows:

| | |
|---|---|
| $30 \cdot 10^6$ cells, vaccinated donor vs. $10 \cdot 10^6$ cells, vaccinated donor; 0.0053 | (16.1) |
| $30 \cdot 10^6$ cells, vaccinated donor vs. $3 \cdot 10^6$ cells, vaccinated donor; 0.0012 | (16.2) |
| $30 \cdot 10^6$ cells, vaccinated donor vs. $30 \cdot 10^6$ cells, "naive" donor; 0.0005 | (16.3) |
| $30 \cdot 10^6$ cells, vaccinated donor vs. Medium; 0.0013 | (16.4) |
| $10 \cdot 10^6$ cells, vaccinated donor vs. $3 \cdot 10^6$ cells, vaccinated donor; 0.8492 | (16.5) |
| $10 \cdot 10^6$ cells, vaccinated donor vs. $30 \cdot 10^6$ cells, "naive" donor; 0.0071 | (16.6) |
| $10 \cdot 10^6$ cells, vaccinated donor vs. Medium; 0.0013 | (16.7) |
| $3 \cdot 10^6$ cells, vaccinated donor vs. $30 \cdot 10^6$ cells, "naive" donor; 0.0052 | (16.8) |
| $3 \cdot 10^6$ cells, vaccinated donor vs. Medium; 0.0013 | (16.9) |
| $30 \cdot 10^6$ cells, "naive" donor vs. Medium; 0.0013 | (16.10) |

In the immediately preceding ten expressions of the significances in this example, the term "cells" is used as an abbreviation for "spleen cells". Significances (16.1) and (16.2) indicate that when the survival rates of two populations that received spleen cells from vaccinated donors are compared with each other, the higher dose of RenCa-immune spleen cells leads to the higher survival rates. Significances (16.3), (16.4), (16.6), (16.7), (16.8) and (16.9) indicate that when the survival rate of a population that received RenCa-immune spleen cells is compared with the survival rate of a population that did not receive RenCa-immune spleen cells, the adoptive transfer of RenCa-immune spleen cells led to the higher survival rate. Significance (16.5) indicates that the survival rates associated with the lower doses of RenCa-immune spleen cells are not statistically different from each other. Significance (16.10) indicates that adoptive transfer of naive spleen cells leads to survival rates that are statistically different from those achieved by administration of the medium only with no spleen cells of any type.

Significances (16.7), (16.9), and (16.10) indicate that low doses of RenCa-immune spleen cells also result in prolongation of survival, although not in actual survival of the animals. It is of further interest to note that a spleen of a healthy mouse has about $100 \cdot 10^6$ spleen cells. Thus, $30 \cdot 10^6$ spleen cells of a RenCa immune mouse corresponds to approximately ⅓ of a spleen. Since the transfer of $30 \cdot 10^6$ RenCa immune spleen cells protects 50% of the animals treated, we can conclude that the immune level in a RenCa immune mouse is just 50% above the level needed to protect the animal.

The cells used in this transfer experiment were derived from BALB/c mice that had been therapeutically vaccinated with RenCa more than 100 days before. The transfer experiment itself, however, is of the prophylactic type because the immune cells were transferred first and then the animals were challenged with a lethal dose of live RenCa tumor cells. The result discussed in this experiment show that, in fact, "immune" lymphoid cells are responsible for tumor elimination.

EXAMPLE 17

Prophylactic Vaccination Experiment

Vaccination groups in this prophylactic study are designated by giving the abbreviated description of a type of vaccination tumor cells, followed by a slash which in turn is followed by another abbreviated description of a type of tumor-inducing cells. For example, RenCa/RenCa stands for a vaccination group which was vaccinated a number of times with a preparation that included inactivated RenCa cells and that received on challenge day a dose of tumor-inducing RenCa cells; RenCa/C26 refers to a vaccination group that was vaccinated a number of times with a preparation that included inactivated RenCa cells and that received on challenge day a dose of tumor-inducing C26 cells (C26 cells are murine colon adenocarcinoma cells). Obviously, the term "medium" in this convention indicates that the vaccination group was administered only medium. For example, the term Medium/RenCa describes a vaccination group that was administered medium whenever the other vaccination groups were administered vaccination preparations that included inactivated tumor cells and that was administered a dose of tumor-inducing RenCa cells on challenge day. C26 cells were cultured in vitro following standard procedures in tissue culture medium (RPMI 1640).

Each of the vaccination groups comprised 10 mice; groups 1–2 were vaccinated three times with a preparation that included inactivated RenCa cells, and IL-2 adsorbed to aluminum hydroxide, whereas groups 3–4 were administered medium at the same times, which were 28 days, 21 days, and 14 days prior to challenge day. As indicated previously, challenge day is designated day 0. Groups 1 and 3 received on challenge day $10^5$ vit C26 cells. Groups 2 and 4 received on challenge day $10^5$ vit RenCa cells. These data are summarized in Table 17.

TABLE 17

| group | n | day −28 | day −21 | day −14 |
|---|---|---|---|---|
| 1 RenCa/C26 | 10 | i.p. RenCa IL-2 AL | i.p. RenCa IL-2 AL | i.p. RenCa IL-2 AL |
| 2 RenCa/RenCa | 10 | i.p. RenCa IL-2 AL | i.p. RenCa IL-2 AL | i.p. RenCa IL-2 AL |
| 3 Medium/C26 | 10 | i.p. Medium | i.p. Medium | i.p. Medium |
| 4 Medium/RenCa | 10 | i.p. Medium | i.p. Medium | i.p. Medium |

Figure 20:
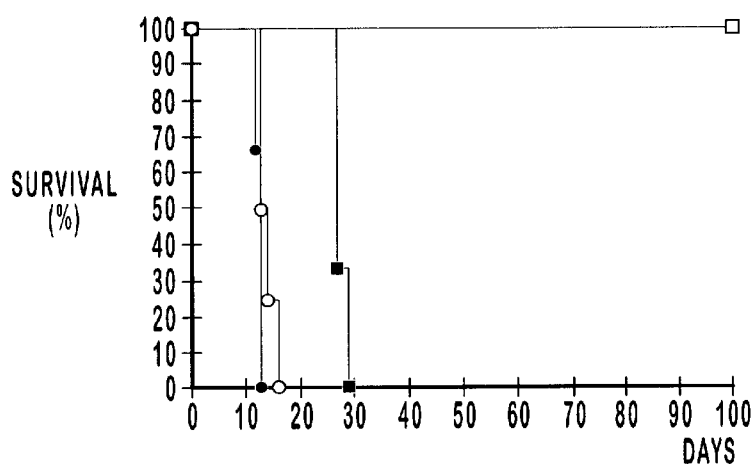
FIG. 20 is a survival plot for a RenCa prophylactic study with RenCa and C26 cross-challenge.

The survival plot in FIG. 20 shows that no mice that had received only medium on vaccination days survived for more than 30 days after challenge day. Notably, no mice that had undergone RenCa/C26 cross-challenge, survived for more than 20 days after challenge day. In contrast, the entire population of mice that was vaccinated with a composition that included inactivated RenCa cells in the form of the preferred composition of this invention and that was challenged with vital RenCa cells was alive 100 days after challenge day. Consequently, the data analyzed in this example show the specificity of the induced immunity to the RenCa cells, and these data also indicate that the most positive effects on survival are achieved when the tumor cells in the vaccination preparation and in the tumor-inducing preparation are of the same type. This observation supports the explanation that the most positive effects on survival rates are achieved when the tumor cells that are applied in the vaccine and that stimulate the induction of a cellular immune response are of the same type as the cells used to challenge the animal.

The significances computed at day 100 after challenge day are as follows:

| | |
|---|---|
| RenCa/C26 vs. RenCa/RenCa; 0.0025 | (17.1) |
| RenCa/C26 vs. Medium/C26; 0.1101 | (17.2) |
| RenCa/C26 vs. Medium/RenCa; 0.0158 | (17.3) |
| RenCa/RenCa vs. Medium/C26; 0.0067 | (17.4) |
| RenCa/RenCa vs. Medium/RenCa; 0.0046 | (17.5) |

Significances (17.1), (17.4), and (17.5) indicate that when the survival rate in the group RenCa/RenCa was compared to that of any other group, the higher survival rate was due to the administration of the same type of cells in the vaccination and in the tumor-inducing preparations. Significance (17.2) indicates that the survival rates associated with RenCa/C26 cross-challenge and those in the group that was administered only medium on vaccination days and tumor inducing C26 cells are not statistically different from each other.

EXAMPLE 18

Prophylactic Vaccination Experiment

The characteristics of the vaccination groups in this study are summarized in Table 18. The conventions and procedures are the same as those followed in Example 17.

TABLE 18

| | Vaccination group | n | Day −28 | Day −21 | Day −14 | Day 0 |
|---|---|---|---|---|---|---|
| 1 | C26/C26 | 10 | i.p. C26 IL-2 AL | i.p. C26 IL-2 AL | i.p. C26 IL-2 AL | i.p. $10^5$ it C26 |
| 2 | C26/RenCa | 10 | i.p. C26 IL-2 AL | i.p. C26 IL-2 AL | i.p. C26 IL-2 AL | i.p. $10^5$ it RenCa |
| 3 | Medium/C26 | 10 | i.p. Medium | i.p. Medium | i.p. Medium | i.p. $10^5$ it C26 |
| 4 | Medium/RenCa | 10 | i.p. Medium | i.p. Medium | i.p. Medium | i.p. $10^5$ it RenCa |

Figure 21:
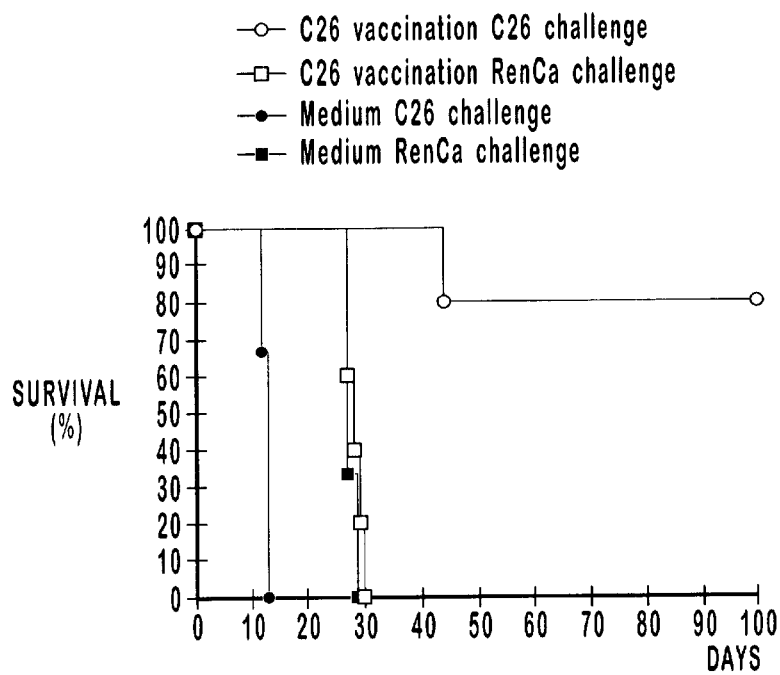
FIG. 21 is a survival plot for a C26 prophylactic study with RenCa and C26 cross-challenge.

The survival plot in FIG. 21 shows that, as in FIG. 20 in Example 17, the highest survival rate of about 80% on day 100 after challenge day is achieved in the group whose vaccination preparation included inactivated C26 cells and that was later challenged with tumor-inducing C26 cells. This observation lends further support to the conclusion that the most positive effects on survival rates are achieved when the tumor cells in the vaccine that stimulate the induction of a cellular immune response are of the same type as the cells used to challenge the animal.

The significances computed at day 100 after challenge day are as follows:

| | |
|---|---|
| C26/C26 vs. C26/RenCa; 0.0017 | (18.1) |
| C26/C26 vs. Medium/C26; 0.0067 | (18.2) |
| C26/C26 vs. Medium/RenCa; 0.0046 | (18.3) |
| C26/RenCa vs. Medium/C26; 0.0067 | (18.4) |
| C26/RenCa vs. Medium/RenCa; 0.5486 | (18.5) |

EXAMPLE 19

Prophylactic Vaccination Experiment

Each one of the five vaccination groups in this B16 prophylactic study comprised 5 mice. The vaccination preparation administered to groups 1–4 included about $10^5$ inactivated B16 cells. In addition, the vaccination preparations administered to groups 2 and 3 included about 10 μg G-CSF, whereas the vaccination preparation administered to group 1 included about 30 μg G-CSF. The vaccination preparations administered to groups 1 and 2 included aluminum hydroxide adsorbed G-CSF, but the vaccination preparation administered to group 3 included a MDP-Lip encapsulated G-CSF depot. Group 5 was the control group. The corresponding vaccination preparations were administered four times (4×) to the individuals in each vaccination group on days 35, 28, 21, and 14 prior to the challenge day. Group 5 received medium only on each one of the four vaccination days. All the administrations were subcutaneous, and the challenge comprised tumor-inducing B16 cells. These group characteristics are summarized in Table 19.

TABLE 19

| vaccination group | n | day −35 | day −28 | day −21 | day −14 | day 0 |
|---|---|---|---|---|---|---|
| 1 | $10^5$ B16 30 μg G-CSF AL (4x) | 5 | s.c. B16 G-CSF AL | s.c. B16 G-CSF AL | s.c. B16 G-CSF AL | s.c. B16 G-CSF AL | s.c. challenge |
| 2 | $10^5$ B16 10 μg G-CSF AL (4x) | 5 | s.c. B16 G-CSF AL | s.c B16 G-CSF AL | s.c. B16 G-CSF AL | s.c. B16 G-CSF AL | s.c. challenge |
| 3 | $10^5$ B16 10 μg G-CSF MDP-Lip (4x) | 5 | s.c B16 G-CSF Lip | s.c. B16 G-CSF Lip | s.c. B16 G-CSF Lip | s.c. B16 G-CSF Lip | s.c. challenge |
| 4 | $10^5$ B16 (4x) | 5 | s.c. B16 | s.c. B16 | s.c. B16 | s.c. B16 | s.c. challenge |
| 5 | Medium (4x) | 5 | s.c. Medium | s.c. Medium | s.c. Medium | s.c. Medium | s.c. challenge |

Figure 22:
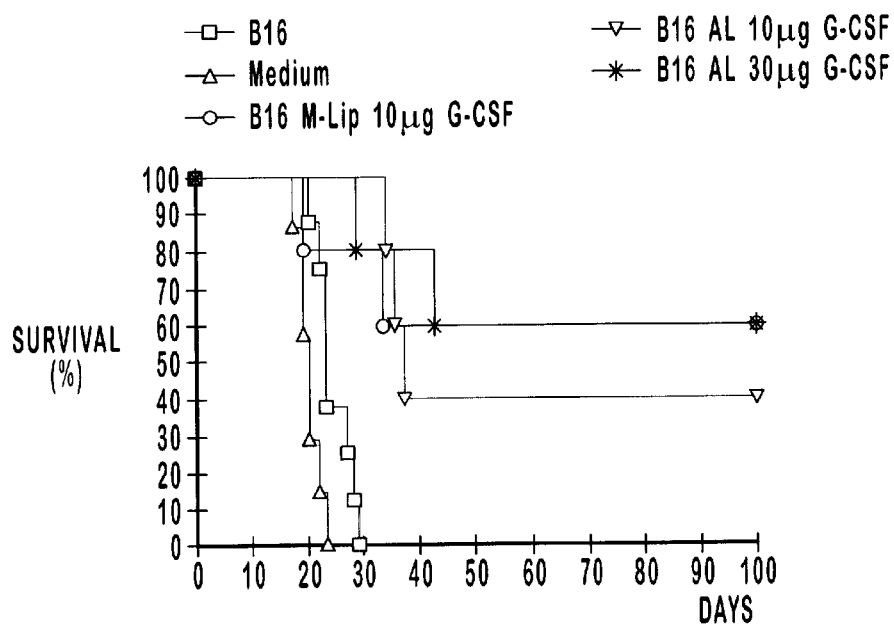
FIG. 22 is a survival plot for a B16 prophylactic study with G-CSF.

FIG. 22 shows that 60% of the individuals in groups 1 and 3 were alive on day 100 after challenge day, whereas only 40% in group had survived the same period of time. Neither the mice that had been administered medium nor the ones that had been vaccinated with inactivated B16 cells only survived for more than 30 days after challenge day. These data indicate that G-CSF encapsulated in MDP-Lip may have greater adjuvant effects than G-CSF adsorbed to aluminum hydroxide because a greater dose of G-CSF had to be administered when it was adsorbed to aluminum hydroxide to achieve the same survival rate on day 100. Notably, even the best survival rate in this experiment is significantly lower than that achieved with the preferred preparation in this invention.

EXAMPLE 20

Prophylactic Vaccination Experiment

This B16 prophylactic study is analogous to that reported in Example 19. Table 20 summarizes the characteristics of the vaccination groups in the present study. Only aluminum hydroxide was employed as depot in this study, and the cytokine was GM-CSF instead of G-CSF. The doses of GM-CSF reported in Table also differ from those of G-CSF reported in Table 19, and the number of mice in each vaccination group are also different.

TABLE 20

| vaccination group | n | day −35 | day −28 | day −21 | day −14 | day 0 |
|---|---|---|---|---|---|---|
| 1 | $10^5$ B16 10 μg GM-CSF AL (4x) | 7 | s.c. B16 GM-CSF AL | s.c. B16 GM-CSF AL | s.c. B16 GM-CSF AL | s.c. B16 GM-CSF AL | s.c. challenge |
| 2 | $10^5$ B16 3 μg GM-CSF AL (4x) | 8 | s.c. B16 GM-CSF AL | s.c. B16 GM-CSF AL | s.c. B16 GM-CSF AL | s.c. B16 GM-CSF AL | s.c. challenge |
| 3 | 10 μg GM-CSF AL (4x) | 6 | s.c. GM-CSF AL | s.c. GM-CSF AL | s.c. GM-CSF AL | s.c. GM-CSF Lip | s.c. challenge |

TABLE 20-continued

| vaccination group | n | day −35 | day −28 | day −21 | day −14 | day 0 |
|---|---|---|---|---|---|---|
| 4 | $10^5$ B16 (4x) | 5 | s.c. B16 | s.c. B16 | s.c. B16 | s.c. B16 | s.c. challenge |
| 5 | Medium (4x) | 6 | s.c. Medium | s.c. Medium | s.c. Medium | s.c. Medium | s.c. challenge |

Figure 23:
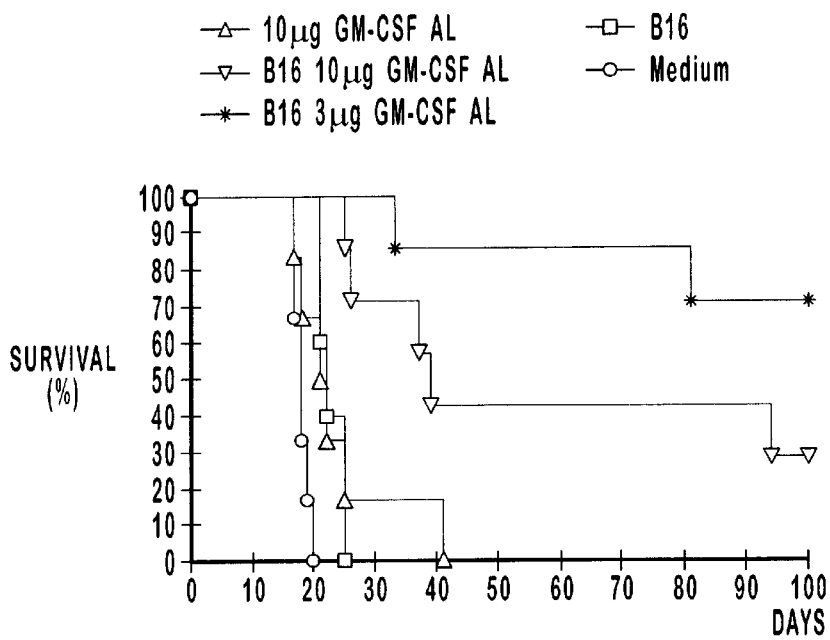
FIG. 23 is a survival plot for a B16 prophylactic study with different dosages of GM-CSF.

FIG. 23 shows that vaccination group 4 that was administered a preparation with antigenic tumor cells but with no depot that would provide the immunostimulating effects of a cytokine survived for less than 30 days after challenge day, whereas the vaccination groups 1 and 2 that were administered a vaccination preparation with antigenic tumor cells and depot with cytokine comprised live individuals at day 100 after challenge day. This is consistent with the data analyzed regarding the effects of IL-2. In this example, the cytokine used in the vaccination preparations for groups 1 and 2 was GM-CSF, and the survival rate on day 100 after challenge day for group 2 that had been administered a vaccination preparation with about 3 μg GM-CSF is greater than that for group 1 that had received a vaccination preparation that included about 10 μg GM-CSF. The combination of antigenic tumor cells with a depot that contained the immunostimulating cytokine GM-CSF administered to groups 1 and 2 also led to more positive survival effects than the preparation administered to group 3 that contained GM-CSF adsorbed to aluminum hydroxide depot, but had no antigenic tumor cells. This result is also consistent with the data regarding the effects of IL-2 adsorbed to aluminum hydroxide in combination with antigenic tumor cells.

The significances computed at day 100 after challenge day are as follows:

| | |
|---|---|
| $10^5$ B16 10 μg GM-CSF AL (4x) vs. $10^5$ B16 3 μg GM-CSF AL (4x); 0.0772 | (20.1) |
| $10^5$ B16 10 μg GM-CSF AL (4x) vs. 10 μg GM-CSF AL (4x); 0.0166 | (20.2) |
| $10^5$ B16 10 μg GM-CSF AL (4x) vs. $10^5$ B16 (4x); 0.0017 | (20.3) |
| $10^5$ B16 10 μg GM-CSF AL (4x) vs. Medium (4x); 0.0002 | (20.4) |
| $10^5$ B16 3 μg GM-CSF AL (4x) vs. 10 μg GM-CSF AL (4x); 0.0002 | (20.5) |
| $10^5$ B16 3 μg GM-CSF AL (4x) vs. $10^5$ B16 (4x); 0.0002 | (20.6) |
| $10^5$ B16 3 μg GM-CSF AL (4x) vs. Medium 4x); <0.0001 | (20.7) |
| 10 μg GM-CSF AL (4x) vs. $10^5$ B16 (4x); 0.9260 | (20.8) |
| 10 μg GM-CSF AL (4x) vs. Medium (4x); 0.0345 | (20.9) |
| $10^5$ B16 (4x) vs. Medium (4x); 0.0012 | (20.10) |

Significance (20.1) indicates that the survival data for vaccination groups 1 and 2 are statistically different at a significance level of about 7.7%. This significance level greater than 5% may in fact indicate that these two sets of data are not statistically different. Significances (20.2), (20.3), (20.4), (20.5), (20.6), and (20.7) lend statistical support to the conclusions stated above regarding the more positive effects on survival of vaccination preparations that include antigenic tumor cells and a depot with an immunostimulating cytokine. Significances (20.9) and (20.10) indicate that the survival data for vaccination groups 3 and 4 are statistically different from the survival data for the control group.

EXAMPLE 21

Therapeutic Vaccination Experiment

In this experiment, an immunostimulating substance other than a cytokine, the bacteria-derived cell wall component muramyl dipeptide (MDP), was used in aluminum hydroxide adsorbed form in the vaccines. Mice in this experiment were injected intra-peritoneally on day −4 with $10^5$ vit RenCa cells. On day 0, mice in group $10^6$ RenCa were vaccinated with $10^6$ irradiated RenCa cells whereas mice in group $10^6$ RenCa 25 μg MDP AL were vaccinated with $10^6$ irradiated RenCa cells with 25 μg MDP adsorbed to 25 μg AL.

Figure 24:
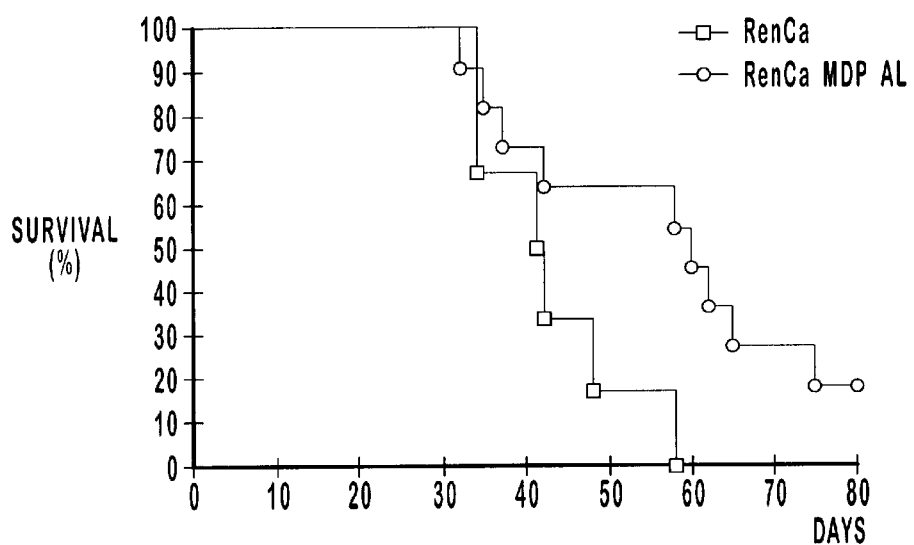
FIG. 24 is a survival plot for a RenCa therapeutic study with MDP.

FIG. 24 shows that no mice in vaccination group $10^6$ RenCa had survived past day 60 after vaccination day, whereas about 20% of the mice in group $10^6$ RenCa 25 μg MDP AL were still alive eighty days after vaccination day. The significance for the results shown in FIG. 24 is as follows:

$10^6$ RenCa vs. $10^6$ RenCa 25 μg MDP AL; 0.0379;
indicating that the survival rate of the mice in group $10^6$ RenCa 25 μg MDP AL is significant when compared with that of the mice in the group $10^6$ RenCa.

EXAMPLE 22

Prophylactic Vaccination Experiment

In this experiment, mice were vaccinated prophylactically against the 38C13 murine B-lymphoma which exposes an immunoglobulin idiotype (the 38C26 idiotype) as a tumor antigen. Vaccinations were administered on days −56, −42, −28, and −14 to mice in vaccination groups $10^6$ 38C13(4×), whose mice received four times $10^6$ irradiated 38C26 B lymphoma cells, vaccination group $10^6$ 38C13 10 μg IL-2 AL (4×), whose mice received four times $10^6$ irradiated 38C26 B lymphoma cells with 10 μg IL-2 adsorbed to 10 μg AL, and vaccination group Medium(4×), whose mice received medium four times. Challenge was done on day 0 by administering $3·10^2$ vit 38C13 cells.

Figure 25:
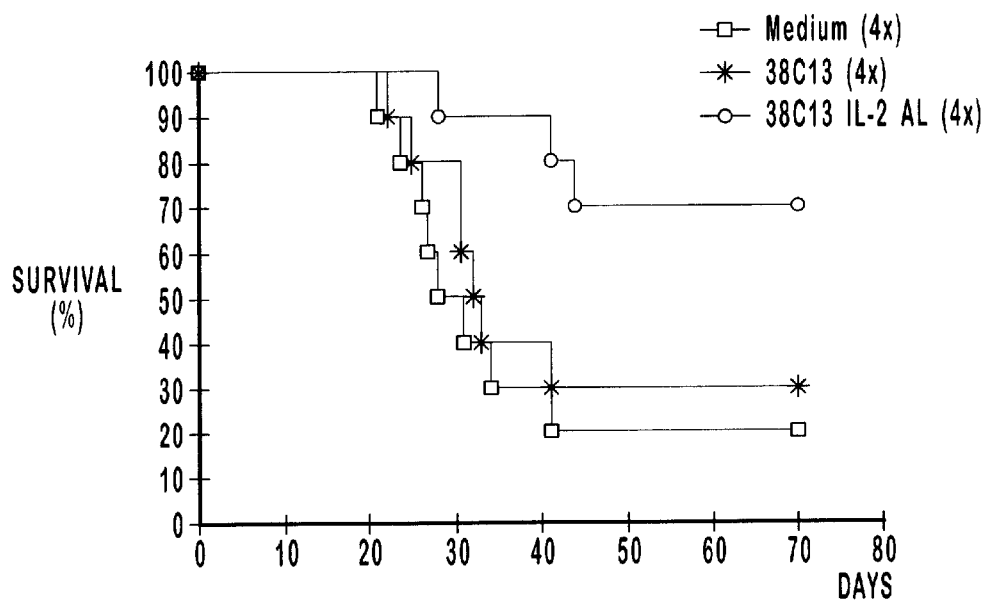
FIG. 25 is a survival plot for a 38C13 prophylacitc study with and without IL-2.

FIG. 25 shows that about 20% and 30% of the mice in vaccination groups Medium(4×) and $10^6$ 38C13(4×), respectively, were alive seventy days after challenge day, whereas about 70% of the mice that had been vaccinated with a preparation that contained $10^6$ irradiated 38C13 B lymphoma cells with 10 μg IL-2 adsorbed to 10 μg AL were alive seventy days after challenge day.

The significances computed for the results shown in FIG. 25 are as follows:

| | |
|---|---|
| Medium (4x) vs. $10^6$ 38C13 (4x); 0.4841 | (22.1) |
| Medium (4x) vs. $10^6$ 38C13 10 μg IL-2 AL (4x); 0.0048 | (22.2) |
| $10^6$ 38C13 (4x) vs. $10^6$ 38C13 10 μg IL-2 AL (4x); 0.0469 | (22.3) |

The survival rates for vaccination group $10^6$ 38C13 10 μg IL-2 AL (4×) are very significant and significant when compared with those for the vaccination groups Medium (4×) and $10^6$ 38C13 (4×), respectively, as significances (22.2) and (22.3) indicate. The survival rates for vaccination group $10^6$ 38C13 (4×), however, are not significant when compared with those for group Medium(4×), as significance (22.1) indicates.

EXAMPLE 23

Prophylactic Vaccination Experiment

The vaccination group characteristics are summarized in Table 21 below.

TABLE 21

| | vaccination group | n | day −35 | day −28 | day −21 | day −14 | day 0 |
|---|---|---|---|---|---|---|---|
| 1 | $10^5$ B16 10 μg rmuGM-CSF AL (4x) | 7 | s.c. B16 rmuGM-CSF AL | s.c. B16 rmuGM-CSF AL | s.c. B16 rmuGM-CSF AL | s.c. B16 rmuGM-CSF AL | s.c. challenge |
| 2 | $10^5$ B16 3 μg rmuGM-CSF AL (4x) | 8 | s.c. B16 rmuGM-CSF AL | s.c. B16 rmuGM-CSF AL | s.c. B16 rmuGM-CSF AL | s.c. B16 rmuGM-CSF AL | s.c. challenge |
| 3 | 10 μg rmuGM-CSF AL (4x) | 6 | s.c. B16 rmuGM-CSF AL | s.c. rmuGM-CSF AL | s.c. B16 rmuGM-CSF AL | s.c. rmuGM-CSF AL | s.c. challenge |
| 4 | $10^5$ B16 (4x) | 5 | s.c. B16 | s.c. B16 | s.c. B16 | s.c. B16 | s.c. challenge |
| 5 | Medium (4x) | 6 | s.c. Medium | s.c. Medium | s.c. Medium | s.c. Medium | s.c. challenge |

Figure 26:
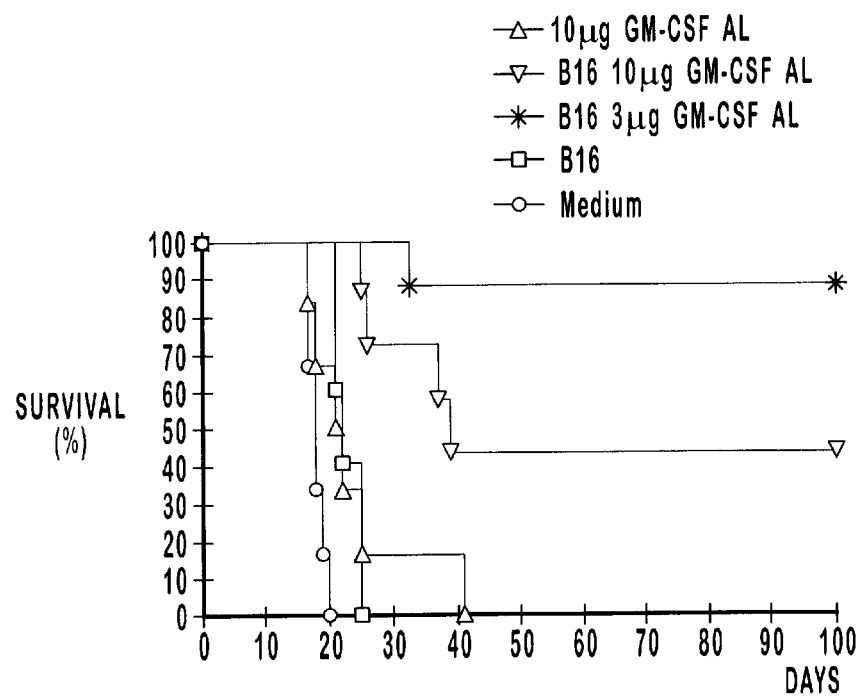
FIG. 26 is a survival plot for a B16 prophylactic study with recombinant murine GM-CSF.

The data shown in FIG. 26 is qualitatively similar to that shown in FIG. 23 of Example 19. Consistently with the data shown in FIG. 23, FIG. 26 shows that vaccination group that was administered a preparation with antigenic tumor cells but with no depot that would provide the immunostimulating effects of a cytokine survived for less than 30 days after challenge day, whereas vaccination groups 1 and 2 that were administered a vaccination preparation with antigenic tumor cells and a cytokine adsorbed on a depot comprised live individuals at day 100 after challenge day. This is consistent with the data analyzed regarding the effecting of IL-2. In this example, the cytokine used in the vaccination preparations for groups 1 and 2 was rnuGM-CSF, and the survival rate on day 100 after challenge day for group 2 that had been administered a vaccination preparation with about 3 μg rmuGM-CSF is greater than that for group 1 that had received a vaccination preparation that included about 10 μg rmuGM-CSF. The combination of antigenic tumor cells with a depot that contained the immunostimulating cytokine rmuGM-CSF administered to groups 1 and 2 also led to more positive survival effects than the preparation administered to group 3 that contained an aluminum hydroxide depot with rmuGM-CSF, but had no antigenic tumor cells. This result is also consistent with the data regarding the effects of IL-2 in combination with antigenic tumor cells and a depot.

Influence of Vaccination Frequency and Administration Loci on Survival

EXAMPLE 24

Prophylactic Vaccination Experiment

The influence of vaccination frequency on survival is analyzed in this B16 prophylactic study. Vaccination groups 1 and 2 comprised ten mice each, vaccination group 2 comprised mice and vaccination group 4 was the control group with six mice. About $10^5$ inactivated B16 cells were included in the vaccination preparations administered to mice in groups 1–3. The vaccination compositions administered to groups 1–2 included about 10 μg IL-2 adsorbed to about 10 μg of aluminum hydroxide. Group 4 was the control group. Vaccinations with the corresponding compositions were subcutaneously administered four times (4×) to individuals in vaccination group 2 on each one of days 35, 28, 21, and 14 prior to challenge day. Vaccination groups 1 and 3 received six vaccinations (6×); the two additional vaccinations were administered one on each one of days 49 and 42 prior to the challenge day. Mice in the control group received only medium on each of the vaccination days of groups 1 and 3. Vaccination group characteristics are summarized in Table 22.

TABLE 22

| | vaccination group | n | vaccination days | day 0 |
|---|---|---|---|---|
| 1 | $10^5$ B16 10 μg IL-2 AL (6x) | 10 | −49, −42, −35, −28, −21, −14 | s.c. $10^5$ it B16 |
| 2 | $10^5$ B16 10 μg IL-2 AL (4x) | 9 | −35, −28, −21, −14 | s.c. $10^5$ it B16 |
| 3 | $10^5$ B16 (6x) | 10 | −49, −42, −35, −28, −21, −14 | s.c. $10^5$ it B16 |
| 4 | Medium (6x) | 6 | −49, −42, −35, −28, −21, −14 | s.c. $10^5$ it B16 |

Figure 27:
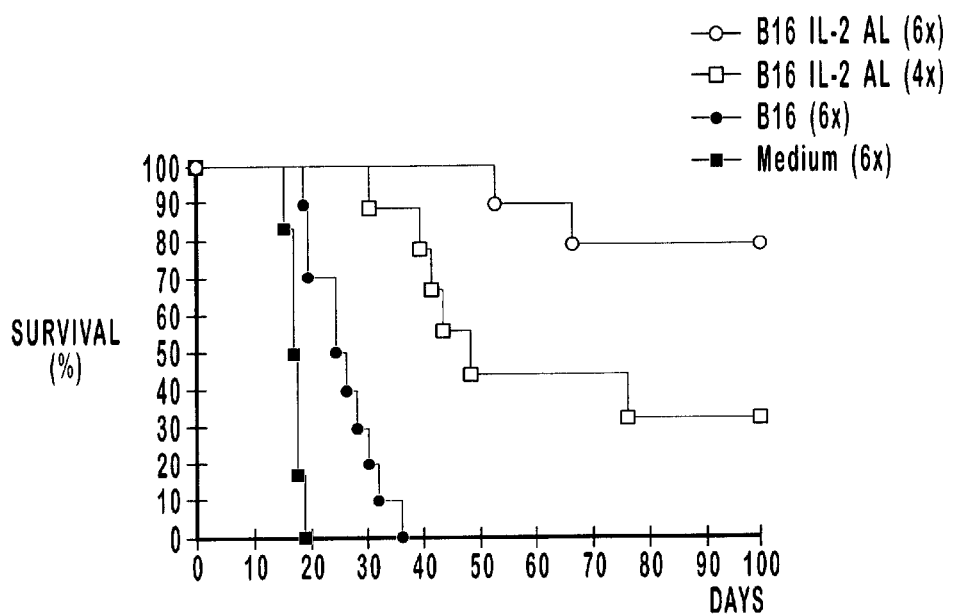
FIG. 27 is a survival plot for a B16 prophylactic study with different vaccination frequencies.

FIG. 27 shows that a greater number of vaccination administrations led to a more positive effect on survival rate. More precisely, 80% of the individuals in group 1 that were vaccinated six times were alive on day 100 after challenge day, whereas only about 30% of the individuals in vaccination group 2 that had been vaccinated four times survived the 100-day period after challenge day. Consistently with data in previous examples, the administration of antigenic tumor cells that did not include cytokine in depot form led to much weaker effects on survival rate, as shown by the fact that no mice in vaccination group 3 survived for 40 days after challenge day even though the individuals in this group had received six vaccinations.

The significances computed at day 100 after challenge day are as follows:

| | |
|---|---|
| $10^5$ B16 10 μg IL-2 AL (6x) vs. $10^5$ B16 10 μg IL-2 AL (4x); 0.0250 | (24.1) |
| $10^5$ B16 10 μg IL-2 AL (6x) vs. $10^5$ B16 (6x); <0.0001 | (24.2) |
| $10^5$ B16 10 μg IL-2 AL (6x) vs. Medium (6x); <0.0001 | (24.3) |
| $10^5$ B16 10 μg IL-2 AL (4x) vs. $10^5$ B16 (6x); <0.0001 | (24.4) |
| $10^5$ B16 10 μg IL-2 AL (4x) vs. Medium (6x); <0.0001 | (24.5) |
| $10^5$ B16 (6x) vs. Medium (6x); 0.0005 | (24.6) |

According to these results, six prophylactic vaccinations had a more positive effect on survival rates than four prophylactic vaccinations when the same vaccination preparation was administered. Consistently with results reported on previously discussed examples, the vaccination preparation that comprised antigenic material with cytokine adsorbed to aluminum hydroxide had more positive effects on survival than the preparations that included only medium or inactivated tumor cells, even when more administrations of these latter preparations were given.

EXAMPLE 25

Intratumoral Injection Experiment

Figure 28:
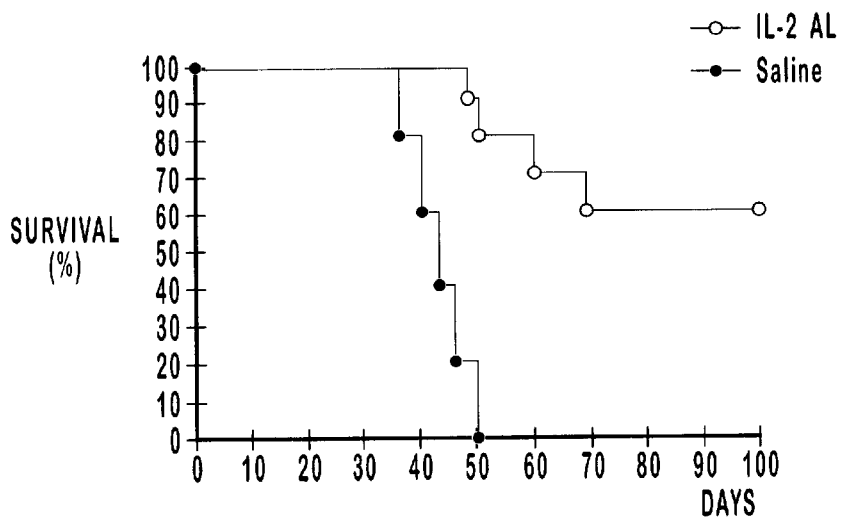
FIG. 28 is a survival plot for a RenCa therapeutic study with intratumoral injection of IL-2 in depot form.

In this RenCa therapeutic study a preparation comprising about 10 μg IL-2 adsorbed to about 10 μg of aluminum hydroxide was injected into tumors induced by injection of $10^5$ vital RenCa tumor cells (intratumoral treatment) every third day after the tumor became palpable. Mice were vaccinated between seven and ten times with about 100 μl of the intratumoral treatment preparation every time. Saline solution with no further additions was administered to the animals in the control group. FIG. 28 shows that no mouse in the control group survived for more than 50 days after the tumor induction day. On day 100, a survival rate of 60% was observed in the group that received the intratumoral treatment preparation. The significance computed on day 100 is 0.0002, which indicates that the explanation that the more positive effects on the survival rate are due to the intratumoral 10 μg IL-2 AL preparation should be accepted over the explanation that the increased survival rate is not due to this preparation with a significance of 0.02%. A comparison of the survival rates shown in FIG. 1 for treatment group 2 with the survival rate shown in FIG. 28 for the group that received intratumoral treatment preparation reveals that the effects of multiple intratumoral injections with a preparation that contained the cytokine IL-2 adsorbed to aluminum hydroxide were more positive than the single subcutaneous administration of the same preparation. However, the effects on survival rates of the single subcutaneous administration of the $10^6$ RenCa 10 μg IL-2 AL preparation were more positive than the effects on survival rates of the multiple intratumoral administration of the intratumoral treatment preparation with 10 μg IL-2 AL, as evinced by the comparison of the survival rates for group 5 in FIG. 1, group 1 in FIG. 2, group 5 in FIG. 8, and group 1 in FIG. 13 with the intratumoral treatment group 10 μg IL-2 AL in FIG. 28. This is due to the fact that the tumors into which the intratumoral aluminum hydroxide adsorbed IL-2 was injected had a considerable size (they were "palpable") and contained more tumor cells than the tumor-inducing inoculum applied to the animals of , e.g., group 5 in FIG. 1.

EXAMPLE 26

Intratumoral Injection Experiment

Figure 29:
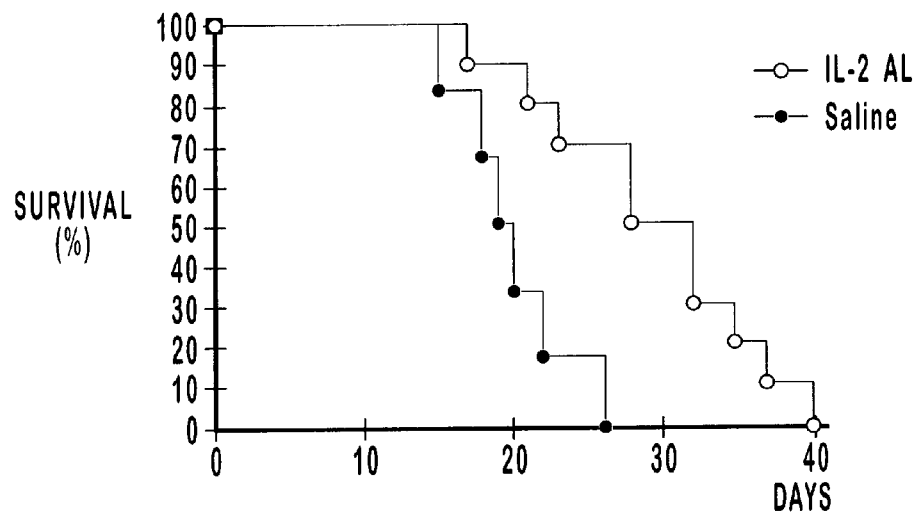
FIG. 29 is a survival plot for a B16 therapeutic study with intratumoral injection of IL-2 in depot form.

In this B16 therapeutic study an intratumoral treatment preparation comprising about 10 μg IL-2 adsorbed to about 10 μg of aluminum hydroxide ("10 μg IL-2 AL") was applied every third day after the tumor became palpable. Mice were injected between three and nine times with about 100 μl of the preparation every time. Saline solution with no further additions was administered to the animals in the control group. A significance of 0.003 on day 40 indicates that the more positive effects on survival rates observed in the group that received the intratumoral treatment preparation are due to the multiple intratumoral administration of the 10 μg IL-2 AL preparation. However, FIG. 29 shows that no mouse in the group that received this preparation multiple times in the tumor survived for more than 40 days after the tumor induction day. This observation is consistent with the known low immunogenicity of this tumor type as compared to the immunogenicity of the RenCa tumor.

EXAMPLE 27

Prophylactic Vaccination Experiment

The influence of spatial distribution of IL-2 containing vaccines on survival is analyzed in this B16 prophylactic study. Vaccination groups comprised six mice each. About $10^5$ inactivated B16 cells were included in the vaccination preparations administered to mice in groups 1–4. The vaccination compositions administered to group 1 included about 10 μg IL-2, and the vaccination compositions administered to vaccination groups 2 and 3 included about 2.5 μg IL-2 and about 10 μg IL-2, respectively. Vaccination group 4 received inactivated B16 cells only, with no cytokine. Vaccination group 5 was the control group. Four vaccinations (4x) with the corresponding composition were subcutaneously administered to individuals in vaccination groups 1–4, one vaccination on each one of days 35, 28, 21, and 14 prior to challenge day. Individuals in vaccination group 1 received one vaccination (1x) dose at one location each one of the vaccination days. Individuals in vaccination groups 2, 3 and 4 received one vaccination dose at four locations every vaccination day.

Because of the number of administration loci, mice in vaccination groups 1, 2 and 3 received on each vaccination day total dosages of about 10 μg IL-2, about 10 μg IL-2, and about 40 μg IL-2, respectively. The dosage administered to mice in vaccination group 1 was localized at one administration locus, whereas the dosages administered to mice in groups 2 and 3 were equally distributed among four administration loci. Consequently, mice in vaccination groups 1 and 2 received the same amount of IL-2, but the local amount delivered to mice in vaccination group 1 was four-fold the amount of IL-2 that was locally delivered to mice in vaccination group 2. Mice in vaccination groups 1 and 3 received the same local amounts of IL-2, but the total amount of IL-2 administered to mice in group 3 was four-fold the amount of IL-2 that was administered to mice in vaccination group 1. The total amount of IL-2 that was administered to mice in vaccination group 2 was one fourth the total amount of IL-2 that was administered to mice in vaccination group 3, and the relationship is the same when the local amounts of IL-2 administered to these two vaccination groups are compared with each other.

Mice in the control group received only medium administered to four locations on each of the vaccination days. Vaccination group characteristics are summarized in Table 23.

TABLE 23

| vaccination group | n | day −35 | day −23 | day −21 | day −14 | day 0 |
|---|---|---|---|---|---|---|
| 1 | $10^5$ B16 10 μg IL-2 (4x) 1x dose/ 1 location | 6 | s.c. B16 IL-2 | s.c. B16 IL-2 | s.c. B16 IL-2 | s.c. B16 IL-2 | s.c. challenge |
| 2 | $10^5$ B16 10 μg IL-2 (4x) 1x dose/ 4 locations | 6 | s.c. B16 IL-2 | s.c. B16 IL-2 | s.c. B16 IL-2 | s.c. B16 IL-2 | s.c. challenge |
| 3 | $10^5$ B16 40 μg IL-2 (4x) 1x dose/ 4 locations | 6 | s.c. B16 IL-2 | s.c. B16 IL-2 | s.c. B16 IL-2 | s.c. B16 IL-2 | s.c. challenge |
| 4 | $10^5$ B16 (4x) | 6 | s.c. B16 | s.c. B16 | s.c. B16 | s.c. B16 | s.c. challenge |
| 5 | Medium (4x) | 6 | s.c. Medium | s.c. Medium | s.c. Medium | s.c. Medium | s.c. challenge |

Figure 30:
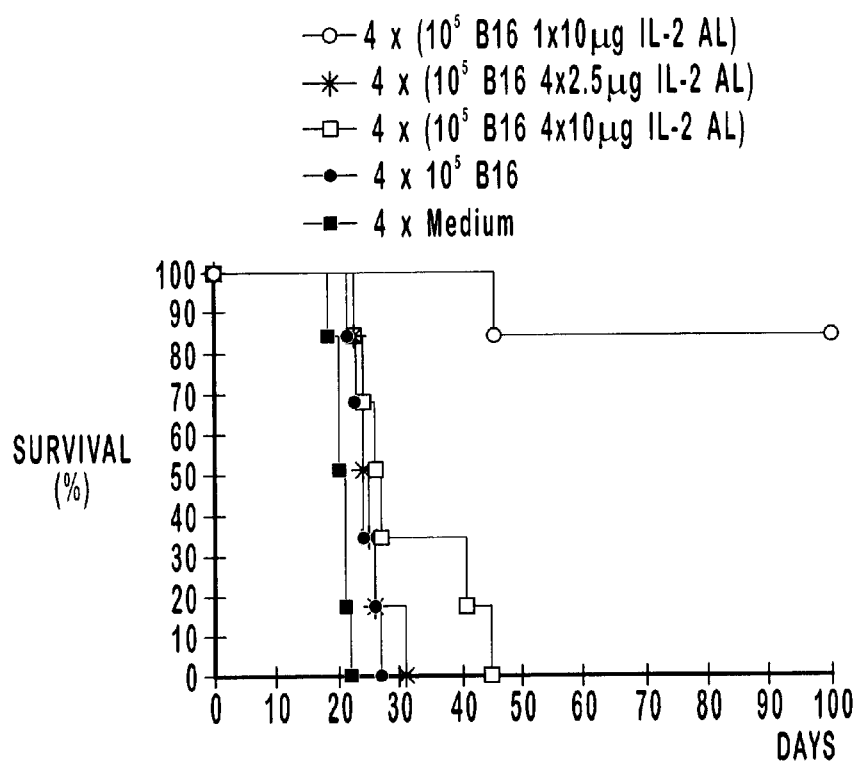
FIG. 30 is a survival plot for a B16 prophylactic study with a spatial distribution of vaccines with different dosages of AL-adsorbed IL-2.

FIG. 30 shows that no mouse in vaccination groups 2–5 survived for fifty days after challenge day, but the survival rate observed in group 1 was over 80% on day 100 after challenge day. Therefore, the more Positive effects on survival rates were achieved by the administration at only one locus of the vaccination preparation $10^5$ B16 10 μg IL-2 AL once every vaccination day. On the one hand, the administration at four different loci of the vaccination preparation $10^5$ B16 2.5 μg IL-2 AL each may have provided a local concentration of cytokine that was too low for having more Positive effects on survival rates. On the other hand, the administration of the vaccination preparation $10^5$ B16 10 μg IL-2 AL each at four different inoculation sites provided a total dose of cytokine that may have been to high, although the local dose in each of the four inoculation sites was exactly in the optimal range. In this latter case, the total amount of cytokjie may have been comparable to the amount that is delivered by systemic administration, and the absence of more Positive effects on survival rates could be due to the known suppression effects that are induced by some systemic administration of cytokines. As previously discussed, FIG. 12 shows the effects on survival rates of the administration at one locus of vaccination preparations with doses of IL-2 that are higher than and lower than about 10 μg IL-2. The survival rates observed in vaccination groups 1–3 in FIG. 12 show that the IL-2 dose that had better effects on survival rates was about 10 μg. These data support the observation that the optimal effects on survival rates are preferably achieved by the administration only at one locus of the vaccination preparation that has showed the best effects on survival rates in experiments performed with different cytokine doses, different amounts of tumor cells, and different depot formulations.

EXAMPLE 28

Cytokine Release From Depot

Release of IL-2 from the IL-2-AL adsorbate strongly depends on the ratio of IL-2 to adsorbent used for loading. When 10 μg IL-2 are mixed with 10 μg AL, about 90% of the IL-2 is adsorbed; when 10 μg IL-2 are mixed with 10 μg AL, about 98% of the IL-2 is adsorbed, and when 10 μg IL-2 are mixed with 100 μg AL, about 100% of the IL-2 is adsorbed. Upon incubation at room temperature for two hours and mixing, the following in vitro release levels are observed: 11.4% for the 10 μg IL-2/10 μg AL, 3.2% for the 10 μg IL-2/30 μg AL, and 2.1% for the 10 μg IL-2/100 μg AL. The results of this experiment indicate that, by choosing the proper IL-2/AL ratio, the release rate can be set as required.

The temporal in vivo release patterns of the following subcutaneous administrations have been investigated: 100 μg IL-2 in free form; 100 μg IL-2/100 μg AL; 10 μg IL-2/10,000 μg CP, and 100 μg IL-2 adsorbed to 1,000,000 tumor cells. The cytokine concentration was determined in peripheral blood during the follow-up period. It is to be understood that the cytokine concentrations determined at different times do not represent the actual release of cytokine at the injection site, but they instead provide readings for the amount of cytokine that is left over after the IL-2 molecules have left the inoculum, diffused through the tissue, penetrated the vascular system, and reached the peripheral blood stream. On route, IL-2 molecules will have bound to and interacted with molecules and cells in tissues and in blood and, consequently, the IL-2 concentration will be reduced considerably.

Figure 31:
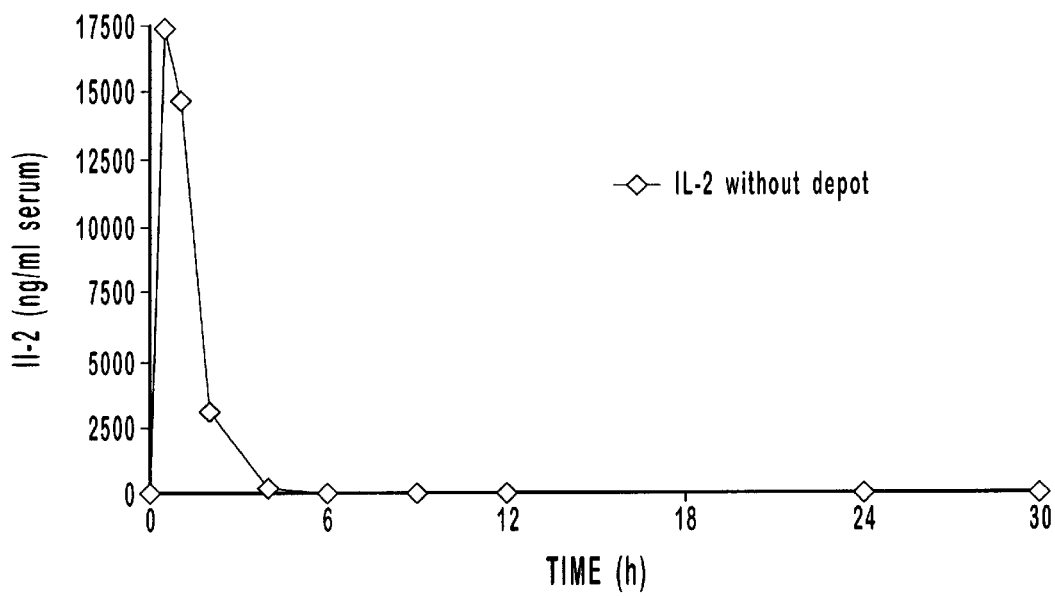
FIG. 31 is a graph showing IL-2 concentrations in peripheral blood as a function of time after subcutaneous administration of free IL-2.

The results obtained in these experiments show that:

(a) A very high IL-2 concentration peak (about 17 μg/ml) is determined in the peripheral blood of the mice within 30 minutes of the injection of 100 μg IL-2 in free form. Assuming a total blood volume of 3.0 ml per mouse, this peaked release contains about 50% of the injected IL-2. Within hours after injection, the IL-2 concentration in peripheral blood comes down to normal values. These results are graphically shown in FIG. 31.

Figure 32:
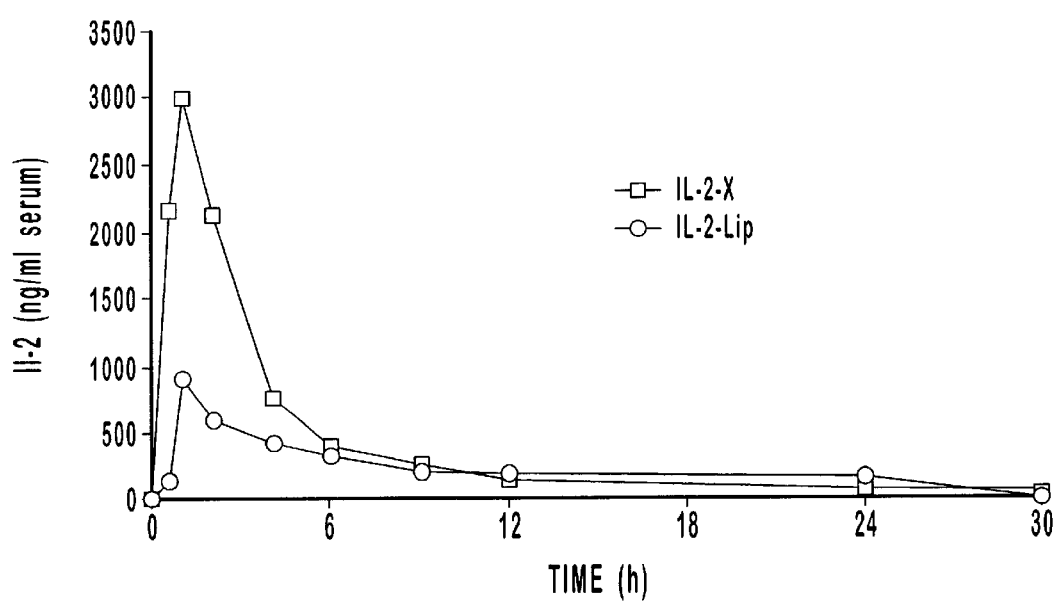
FIG. 32 is a graph showing IL-2 concentrations in peripheral blood as a function of time after subcutaneous administration of IL-2/depot combinations.

(b) An IL-2 concentration peak of 3 μg/ml is reached at about one hour after the injection of 100 μg IL-2/100 μg AL. This peaked release contains about 10% of the injected IL-2. The presence of IL-2 in low concentration in the peripheral blood of the mice is extended over a long time, and only after 48 hours is the concentration below the normal level. These results are graphically shown in FIG. 32.

(c) An IL-2 concentration peak of 4 μg/ml is reached at about one hour after the injection of 100 μg IL-2/10,000 μg CP. This peaked release contains about 12% of the injected IL-2. IL-2 at low concentration is detectable in the peripheral blood of the mice for up to 48 hours. The release pattern of IL-2 in CP adsorbed form looks very much like the release pattern of IL-2 in AL adsorbed form.

(d) An IL-2 concentration peak of 5.7 μg/ml is reached about 30 minutes after the injection of 100 μg IL-2 adsorbed to 1,000,000 tumor cells. This peaked release contains about 17% of the injected IL-2. The IL-2 concentration in peripheral blood comes down to normal values within 24 hours after injection of the IL-2 adsorbed on tumor cells.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A composition comprising tumor cells, aluminum hydroxide, and interleukin-2.

2. The composition of claim 1, wherein the tumor cells have been inactivated by irradiation with one or more X-ray doses of about 100–200 Gray.

3. The composition of claim 1, wherein the composition comprises about $10^5$ to about $10^8$ tumor cells.

4. The composition of claim 1, wherein the tumor cells are selected from the group consisting of melanoma cells, renal carcinoma cells, prostate carcinoma cells, colon carcinoma cells, pancreas carcinoma cells, and lung carcinoma cells.

5. The composition of claim 1, wherein the tumor cells comprise B lymphoma cells.

6. The composition of claim 1, wherein the aluminum hydroxide is present in an amount of at least about 10 μg.

7. The composition of claim 1, wherein the interleukin-2 is present in an amount of at least about 10 μg.

8. The composition of claim 1, wherein the ratio of interleukin-2 to aluminum hydroxide is from about 0.1 to about 1 μg/μg.

9. The composition of claim 1, wherein the tumor cells include irradiated tumor cells.

* * * * *

UNITED STATES PATENT AND TRADEMARK OFFICE
CERTIFICATE OF CORRECTION

PATENT NO.     : 6,406,689 B1
DATED          : June 18, 2002
INVENTOR(S)    : Frank W. Falkenberg and Oliver C. Krup It is certified that error appears in the above-identified patent and that said Letters Patent is hereby corrected as shown below:

Title page,
After U.S. PATENT DOCUMENTS, insert -- FOREIGN PATENT DOCUMENTS (DE) 4411425   Germany --

Column 3,
Line 10, after "up to" change "1" to -- 5 --
Line 41, before "Vaccine" change "Implicationsfor" to -- Implications for --

Column 5,
Line 6, before "and background" change "105-499" to -- 105-489 --
Line 32, after "Immunomodulators," change "of ten" to -- often --

Column 7,
Line 9, after "X-rays" change "of fers" to -- offers --

Column 8,
Line 4, after "tumors" change "of ten" to -- often --

Column 10,
Line 15, after "patients is" change "of ten" to -- often --

Column 11,
Line 5, after "Host" change "Immunoreaetivity:" to -- Immunoreactivity --

Column 13,
Line 19, after "transfected" change "Btumor" to -- B16 tumor --

Column 14,
Line 3, after "tedious and" change "of ten" to -- often --
Line 12, before "generates" change "colony-stimulatingfactor" to -- colony-stimulating factor --
Line 39, before "Mouse" change "Cene-Transduced" to -- Gene-Transduced --
Line 52, before "diminished." change "of ten" to -- often --
Line 56, after "P.," change "Fomy," to -- Forny, --

Column 15,
Line 10, after "injected" change "106" to -- $10^6$ --

UNITED STATES PATENT AND TRADEMARK OFFICE
CERTIFICATE OF CORRECTION

PATENT NO. : 6,406,689 B1
DATED : June 18, 2002
INVENTOR(S) : Frank W. Falkenberg and Oliver C. Krup It is certified that error appears in the above-identified patent and that said Letters Patent is hereby corrected as shown below:

Column 26,
Line 39, before "several" change "adiministered" to -- administered --

Column 27,
Line 39, after "success can" change "of ten" to -- often --
Line 66, after "every" insert -- 3 --

Column 30,
Line 38, before "used instead" change "of ten" to -- often --
Line 45, after "p>0.05," change "0.01<p<0.05, 0.001<p<0.01" to -- $0.01 < p \leq 0.05$, $0.001 < p \leq 0.01$ --

Column 32,
Line 26, after "Five" delete "105"
Line 28, after "100" change "µof" to -- µg of --

Column 33,
Line 53, before "named" delete "is"

Column 35,
Line 22, after "comprised" insert -- 5 --
Line 31, after "group" insert -- 7 --
Line 60, before "together" change "104" to -- $10^4$ --

Column 38,
Line 55, after "inactivated" change "B116" to -- B16 --

Column 40,
Line 14, after "group" change "5" to -- 7 --
Line 15, after "comprised" insert -- 4 --
Line 24, after "ratios of" change "10 µg" to -- 3 µg --
Line 24, before "of aluminum" change "10 µg to -- 3 µg --
Line 25, before "IL-2" change "10 µg" to -- 3 µg --
Line 25, before "of aluminum" change "10 µg" to -- 3 µg --
Line 50, after "group" insert -- 5 --

Column 41,
Line 65, before "adsorbed" change "10 µg" to -- 3 µg --

UNITED STATES PATENT AND TRADEMARK OFFICE
CERTIFICATE OF CORRECTION

PATENT NO. : 6,406,689 B1
DATED : June 18, 2002
INVENTOR(S) : Frank W. Falkenberg and Oliver C. Krup It is certified that error appears in the above-identified patent and that said Letters Patent is hereby corrected as shown below:

Column 41 (cont'd),
Line 65, after " to about" change "10 μg" to -- 3 μg --

Column 42,
Line 26, after "group" change "1" to -- 4 --
Line 26 after "near" change "55" to -- 25 --
Line 27, after "over" change "10" to -- 3 --
Line 28, before "of aluminum" change "10 μg" to -- 3 μg --
Line 55, after "indicates" insert -- that the --

Column 43,
Line 11, after "about" change "10 μg" to -- 3 μg --
Line 12, before "of aluminum" change "10 μg" to -- 3 μg --
Line 13, after "about" change "10 μg" to -- 1 μg --

Column 44,
Line 2, after "RenCa" change "10 μg" to -- 1 μg --
Line 26, after "comprised" insert -- 6 --

Column 45,
Line 12, after "about" change "10 μg." to -- 3 μg. --

Column 46,
Line 34, after "10 μg of" change "IL-2" to -- IL-4 --
Line 48, before "AL" change "IL-2" to -- IL-4 --

Column 47,
Line 4, after "10 μg" change "IL-2" to -- IL-4 --

Column 48,
Line 4, after "statistical" change "Significance" to -- significance --
Line 36, after "from the" change "supematant" to -- supernatant --
Line 40, after "murine" change "IL-2" to -- IL-4 --

Column 49,
Line 26, after "about" change "10 μg" to -- 3 μg --
Line 53, before "together" change "IL-2" to -- IL-4 --

UNITED STATES PATENT AND TRADEMARK OFFICE
CERTIFICATE OF CORRECTION

PATENT NO. : 6,406,689 B1
DATED : June 18, 2002
INVENTOR(S) : Frank W. Falkenberg and Oliver C. Krup It is certified that error appears in the above-identified patent and that said Letters Patent is hereby corrected as shown below:

<u>Column 49 (cont'd),</u>
Line 57, after "indicate that" change "IL-2" to -- IL-4 --
Line 61, after "combination of" change "IL-2" to -- IL-4 --

<u>Column 50,</u>
Line 13, before "Membrane" change "ultracentrifiigation." to -- ultracentrifugation. --

<u>Column 55,</u>
Line 51, after "Table" insert -- 20 --

<u>Column 57,</u>
Line 51, after "irradiated" change "38C26" to -- 38C13 --
Line 54, before "B lymphoma" change "38C26" to -- 38C13 --

<u>Column 58,</u>
Line 53, after "group" insert -- 4 --

<u>Column 59,</u>
Line 17, before "comprised" change "2" to -- 3 --
Line 18, after "comprised" insert -- 9 --

<u>Column 62,</u>
Line 58, after "amount of" change "cytokjie" to -- cytokine --

<u>Column 63,</u>
Line 16, after "mixed with" change "10 µg" to -- 30 µg --

UNITED STATES PATENT AND TRADEMARK OFFICE
CERTIFICATE OF CORRECTION

PATENT NO.   : 6,406,689 B1
DATED        : June 18, 2002
INVENTOR(S)  : Frank W. Falkenberg and Oliver C. Krup It is certified that error appears in the above-identified patent and that said Letters Patent is hereby corrected as shown below:

<u>Column 63 (cont'd)</u>,
Line 28, after "AL;" change "10 µg" to -- 100 µg --
Line 48, after "Within" insert -- 9 --

Signed and Sealed this

Twenty-ninth Day of July, 2003

JAMES E. ROGAN
*Director of the United States Patent and Trademark Office*